US010266807B2

(12) United States Patent
Rajesh et al.

(10) Patent No.: US 10,266,807 B2
(45) Date of Patent: Apr. 23, 2019

(54) METHODS AND COMPOSITIONS FOR CULTURING ENDODERM PROGENITOR CELLS IN SUSPENSION

(71) Applicant: FUJIFILM Cellular Dynamics, Inc., Madison, WI (US)

(72) Inventors: Deepika Rajesh, Madison, WI (US); Sarah Alice Burton, Madison, WI (US)

(73) Assignee: FUJIFILM Cellular Dynamics, Inc., Madison, WI (US)

( * ) Notice: Subject to any disclaimer, the term of this patent is extended or adjusted under 35 U.S.C. 154(b) by 235 days.

(21) Appl. No.: 14/244,396

(22) Filed: Apr. 3, 2014

(65) Prior Publication Data

US 2014/0329321 A1 Nov. 6, 2014

Related U.S. Application Data

(60) Provisional application No. 61/808,003, filed on Apr. 3, 2013.

(51) Int. Cl.
*C12N 5/071* (2010.01)
*C12N 5/074* (2010.01)

(52) U.S. Cl.
CPC ......... *C12N 5/0676* (2013.01); *C12N 5/0607* (2013.01); *C12N 5/0696* (2013.01); *C12N 2500/02* (2013.01); *C12N 2500/90* (2013.01); *C12N 2500/92* (2013.01); *C12N 2500/98* (2013.01); *C12N 2501/10* (2013.01); *C12N 2501/11* (2013.01); *C12N 2501/115* (2013.01); *C12N 2501/119* (2013.01); *C12N 2501/15* (2013.01); *C12N 2501/155* (2013.01); *C12N 2501/16* (2013.01); *C12N 2501/165* (2013.01); *C12N 2501/33* (2013.01); *C12N 2501/415* (2013.01); *C12N 2501/999* (2013.01); *C12N 2506/45* (2013.01)

(58) Field of Classification Search
CPC .................................................. C12N 5/0676
See application file for complete search history.

(56) References Cited

U.S. PATENT DOCUMENTS

| 5,942,435 | A | * | 8/1999 | Wheeler | ............ | A01K 67/0271 |
|---|---|---|---|---|---|---|
| | | | | | | 435/325 |
| 7,510,876 | B2 | | 3/2009 | D'Amour et al. | | |
| 8,129,182 | B2 | | 3/2012 | D'Amour et al. | | |
| 2006/0148081 | A1 | * | 7/2006 | Kelly | ................ | C12N 5/0603 |
| | | | | | | 435/366 |
| 2009/0269845 | A1 | * | 10/2009 | Rezania | ............... | C12N 5/0606 |
| | | | | | | 435/366 |
| 2011/0212061 | A1 | | 9/2011 | Keller et al. | | |
| 2012/0264209 | A1 | | 10/2012 | Odorico et al. | | |
| 2014/0037600 | A1 | | 2/2014 | Yu | | |

FOREIGN PATENT DOCUMENTS

| EP | 2 233 566 | 9/2010 |
|---|---|---|
| WO | WO 2007/051038 | 5/2007 |
| WO | WO 2007/103282 | 9/2007 |
| WO | WO 2007/143193 | 12/2007 |
| WO | WO 2008/094597 | 8/2008 |
| WO | WO 2009/027654 | 3/2009 |
| WO | WO 2010/011352 | 1/2010 |
| WO | WO 2011/139628 | 11/2011 |
| WO | WO 2012/025725 | 3/2012 |
| WO | WO 2012/178215 | 12/2012 |
| WO | WO 2013/163739 | 11/2013 |

OTHER PUBLICATIONS

Brevini et al., 2010, Theriogenology, vol. 74, pp. 544-550.*
Paris et al., 2010, Theriogenology, vol. 74, pp. 516-524.*
Munoz et al., 2008, Theriogenology, vol. 69, pp. 1159-1164.*
Lock et al. (2009, Tissue Engineering, vol. 15(8), pp. 2051-2063).*
Williams et al. (2012, Cell, vol. 149, Snapshot: Directed Differentiation of ESCs and iPSCs).*
Xu et al. (2011, Mechanisms of Development, vol. 128, pp. 412-427).*
Cheng et al. (2012, Cell Stem Cell, vol. 10(4), pp. 371-384, public on Feb. 1, 2012).*
NCBI GEO Report, 2 pages.*
Morrison et al. (2008, Cell Stem Cell, vol. 3, pp. 402-415) (Year: 2008).*
Holewa et al., 1997, Molecular and Cellular Biology, vol. 17(2), pp. 687-694 (Year: 1997).*
Levenstein et al., (2006, Stem Cells, vol. 24, pp. 568-574) (Year: 2006).*
Qi et al., 2004, PNAS, vol. 101(16), pp. 6027-6032 (Year: 2004).*
Morikawa et al. (2016, Stem Cell Reports, vol. 6, pp. 64-73) (Year: 2016).*
Green et al., "Generation of anterior foregut endoderm from human embryonic and induced pluripotent stem cells," *Nature Biotechnology*, 29(3):267-272, 2011.
Irion et al., "Directed differentiation of pluripotent stem cells: from developmental biology to therapeutic applications," *Cold Spring Harb. Symp. Quant. Biol.*, 73:101-110, 2008.
Livigni et al., "Differentiation of embryonic stem cells into anterior definitive endoderm," *Current Protocols in Stem Cell Biology*, 1G.3.1-1G.3.10, 2009.
PCT International Search Report and Written Opinion issued in International Application No. PCT/US2014/032804, dated Aug. 4, 2014.
Salvagiotto et al., "A defined, feeder-free, serum-free system to generate in vitro hematopoietic progenitors and differentiated blood cells from hESCs and hiPSCs," *PLoS ONE*, 6(3):e17829, 2011.

(Continued)

*Primary Examiner* — Thaian N Ton
*Assistant Examiner* — David A. Montanari
(74) *Attorney, Agent, or Firm* — Parker Highlander PLLC

(57) ABSTRACT

Provided herein are methods for the in vitro differentiation of induced pluripotent stem cells, which have been expanded and/or maintained under defined conditions, into endodermal precursor cells (EPCs) that are capable of producing mono-hormonal beta cells.

32 Claims, 36 Drawing Sheets

(56) References Cited

OTHER PUBLICATIONS

Semb, "Definitive endoderm: a key step in coaxing human embryonic stem cells into transplantable β-cells," *Biochemical Society Transactions*, 36(3):272, 2008.
Sui et al., "Signaling pathways during maintenance and definitive endoderm differentiation of embryonic stem cells," *The International Journal of Developmental Biology*, 57(1):1-12, 2013.
Ungrin et al., "Rational bioprocess design for human pluripotent stem cell expansion and endoderm differentiation based on cellular dynamics," *Biotechnology and Bioengineering*, 109(4):853-866, 2012.
Baetge et al., "Production of β-cells from human embryonic stem cells," *Diabetes, Obesity and Metabolism*, 10(Suppl. 4):186-194, 2008.
Bragdon et al., "Bone morphogenetic proteins: a critical review," *Cellular Signaling*, 23:609-620, 2011.
Brunton et al., "Potent inhibitors of the hedgehog signaling pathway," *J. Med. Chem.*, 51:1108-1110, 2008.
Chen et al., "Functional evaluation of ES cell-derived endodermal populations reveals differences between nodal and activin A-guided differentiation," *Development*, 140(3):675-686, 2013.
Cheng et al., "Endodermal stem cell populations derived from pluripotent stem cells," *Curr. Opin. Cell. Biol.*, 25(2):265-271, 2013.
Cheng et al., "Hypoxia-inducible factor-1α regulates β cell function in mouse and human islets," *The Journal of Clinical Investigation*, 120(6):2171-2183, 2010.
Cheng et al., "Monolayer endoderm differentiation from human ESCs," *StemBook*, Cambridge (MA):Harvard Stem Cell Institute, 2012. Internet.
Cheng et al., "Self-renewing endodermal progenitor lines generated from human pluripotent stem cells," *Cell Stem Cell*, 10:371-384, 2012.
D'Amour et al., "Production of pancreatic hormone expressing endocrine cells from human embryonic stem cells," *Nat. Biotechnol.*, 24:1392-1401, 2006.
Duvillié, "Vascularization of the pancreas: an evolving role from embryogenesis to adulthood," *Diabetes*, 62:4004-4005, 2013.
Gouon-Evans et al., "BMP-4 is required for hepatic specification of mouse embryonic stem cell-derived definitive endoderm," *Nat. Biotechnol.*, 24:1402-1411, 2006.
Grapin-Botton and Constam, "Evolution of the mechanisms and molecular control of endoderm formation," *Mechanisms of Development*, 124:253-278, 2007.
Hong and Yu, "Applications of small molecule BMP inhibitors in physiology and disease," *Cytokine Growth Factor Rev.*, 20(5-6):409-418, 2009.
King, "The use of animal models in diabetes research," *British Journal of Pharmacology*, 166:877-894, 2012.
Kobberup et al., "ETS-family genes in pancreatic development," *Developmental Dynamics*, 236:3100-3110, 2007.
Lengner et al., "Derivation of pre-X inactivation human embryonic stem cells under physiological oxygen concentrations," *Cell*, 141:872-883, 2010.
Mohyeldin et al., "Oxygen in stem cell biology: a critical component of the stem cell niche," *Cell Stem Cell*, 7:150-161, 2010.
Morrison et al., "Anterior definitive endoderm from ESCs reveals a role for FGF signaling," *Cell Stem Cell*, 3(4):402-415, 2008.
Nostro et al., "Stage-specific signaling through TGFβ family members and WNT regulates patterning and pancreatic specification of human pluripotent stem cells," *Development*, 138:861-871, 2011.
Roth et al., "Design, synthesis, and evaluation of indolinones as inhibitors of the transforming growth factor β receptor I (TGFβRI)," *J. Med. Chem.*, 53:7287-7295, 2010.
Sarkar et al., "Targeted proteomics of the secretory pathway reveals the secretome of mouse embryonic fibroblasts and human embryonic stem cells," *Mol. Cell. Proteomics*, 11(12):1829-1839, 2012.
Shroyer et al., "Gfi 1 functions downstream of Math1 to control intestinal secretory cell subtype allocation and differentiation," *Genes and Development*, 19:2412-2417, 2005.
Solinas et al., "Acyltiourea, acylurea, and acylguanidine derivatives with potent hedgehog inhibiting activity," *Journal of Medicinal Chemistry*, 55:1559-1571, 2012.
Srinivasan and Ramarao, "Animal models in type 2 diabetes research: an overview," *Indian J. Med. Res.*, 125:451-472, 2007.
Stottmann et al., "The BMP antagonists chordin and noggin have essential but redundant roles in mouse mandibular outgrowth," *Developmental Biology*, 240:457-473, 2001.
Willert and Nusse, "Wnt proteins", *Cold Spring Harb. Perspect. Biol.*, 4(9):a007864, 2012.
Winkler et al., "Design and synthesis of inhibitors of hedgehog signaling based on the alkaloid cyclopamine," *Organic Letters*, 11(13):2824-2827, 2009.
Tada et al., "Characterization of mesendoderm: a diverging point of the definitive endoderm and mesoderm in embryonic stem cell differentiation culture," *Development*, 132:4363-4374, 2005.

\* cited by examiner

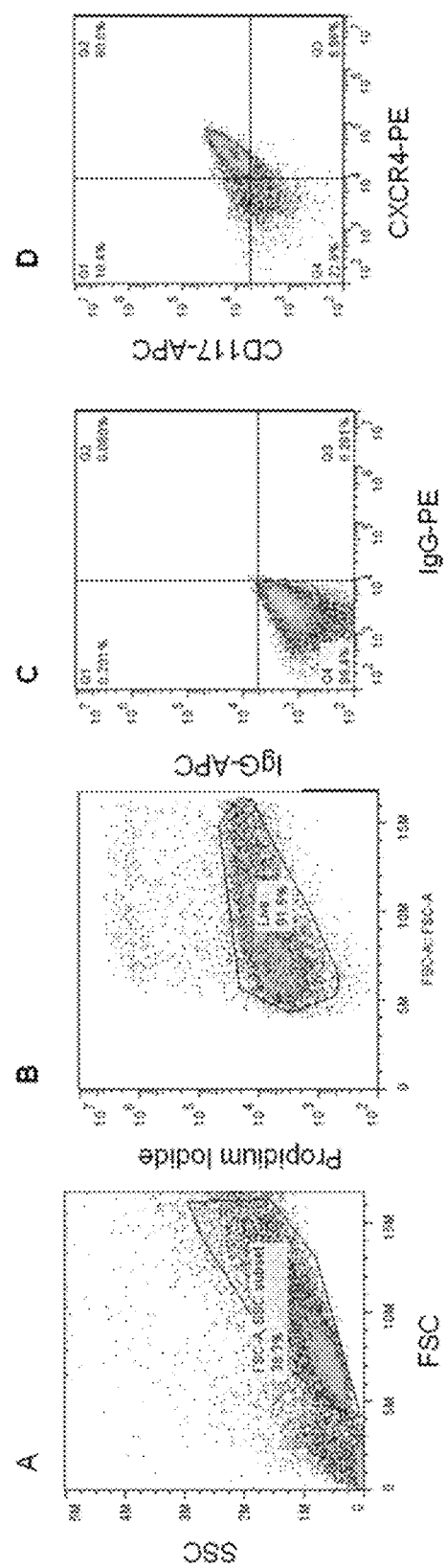
FIGs. 1A-D

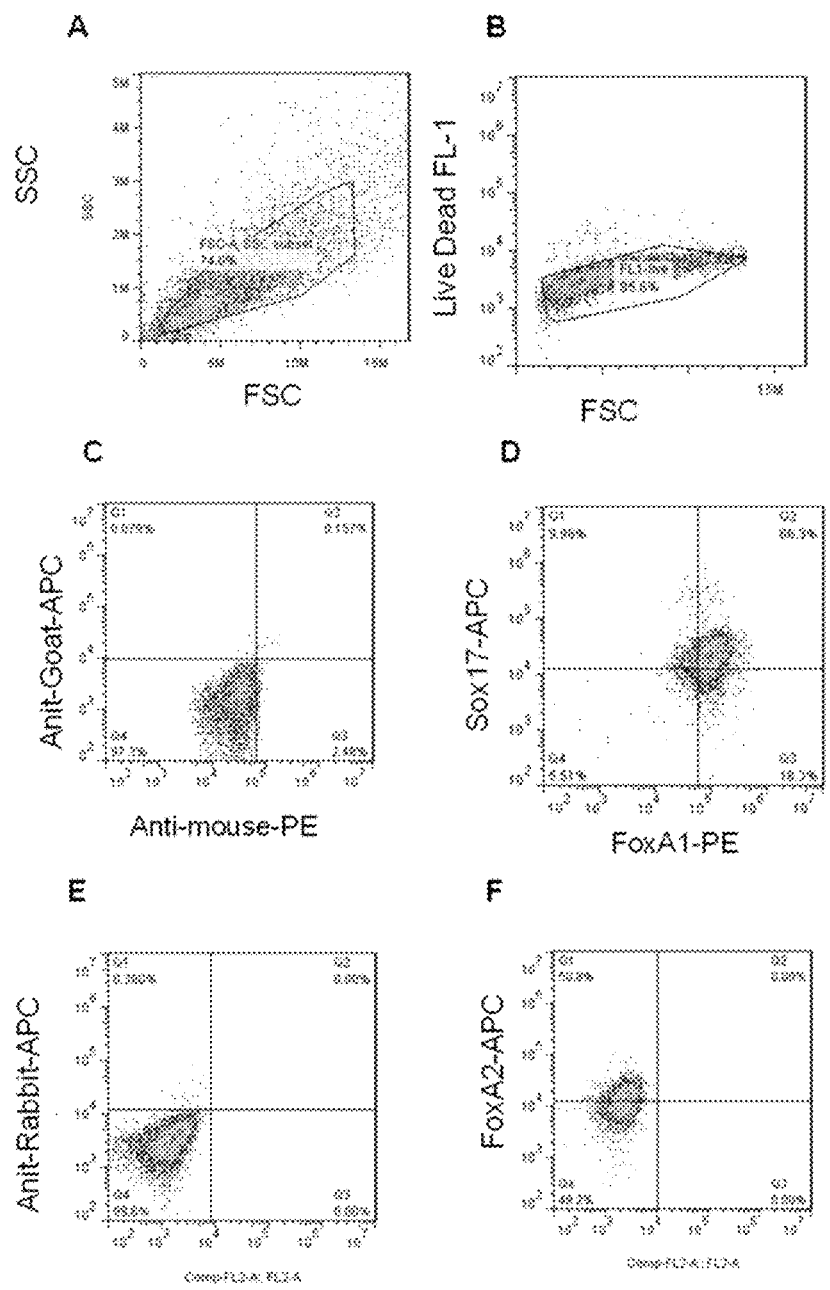
FIGs. 2A-F

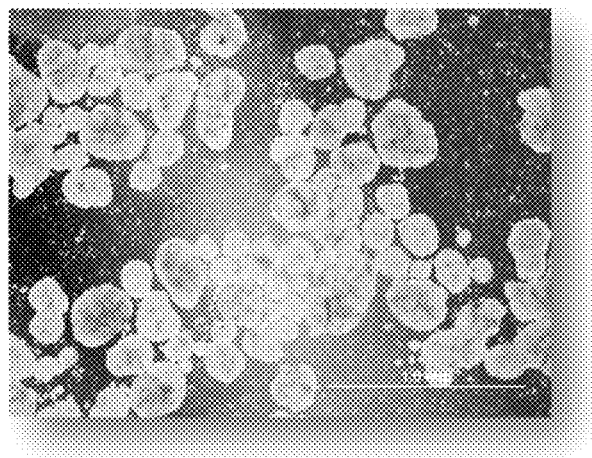
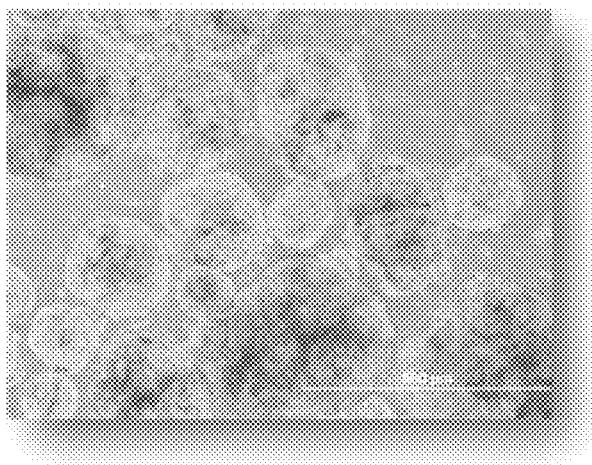
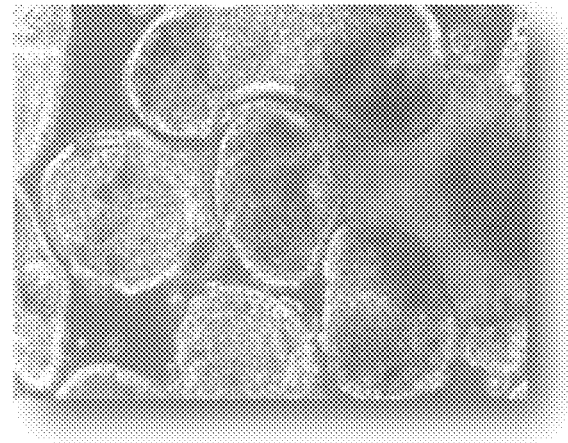
FIG. 8

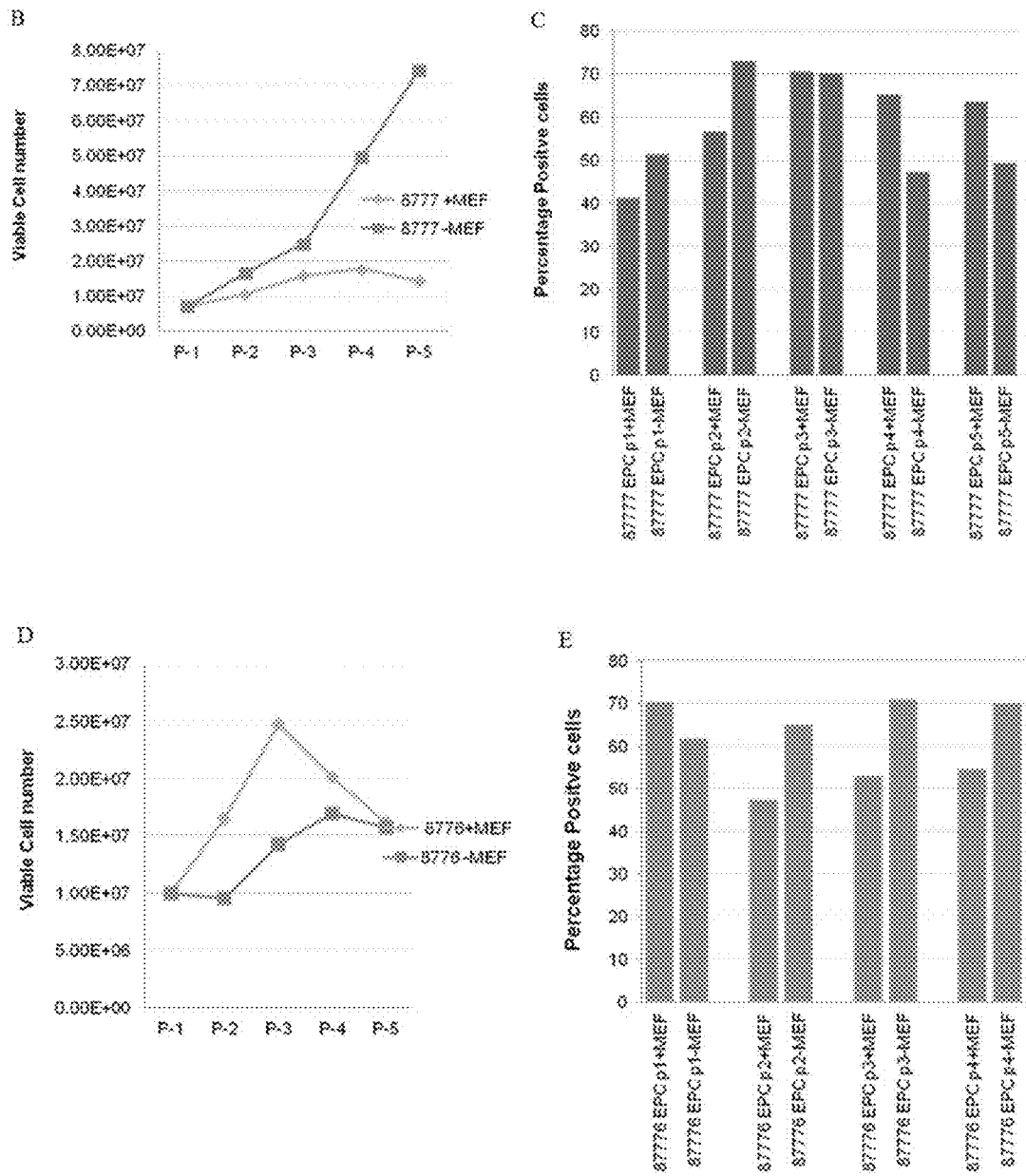
FIGs. 18B-E

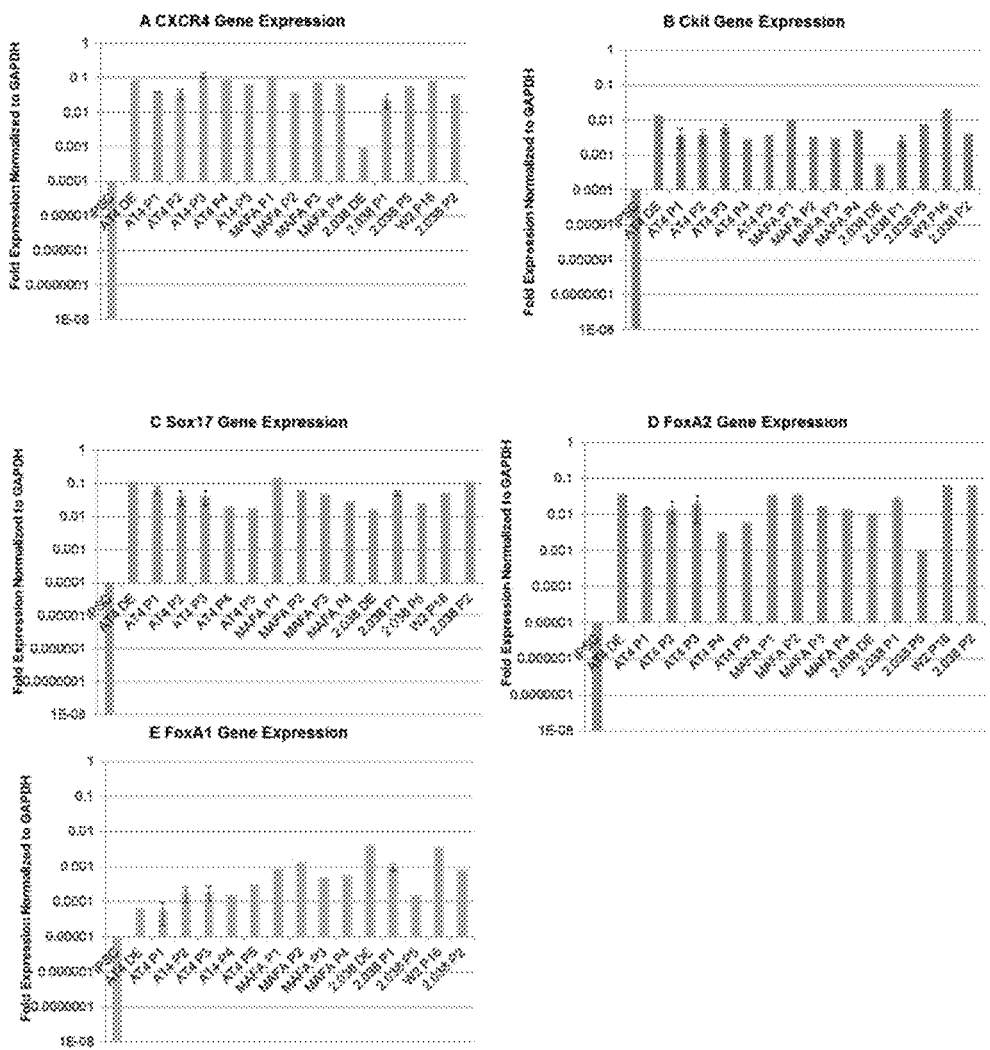
FIGs. 20A-E

FIGs. 24A-B

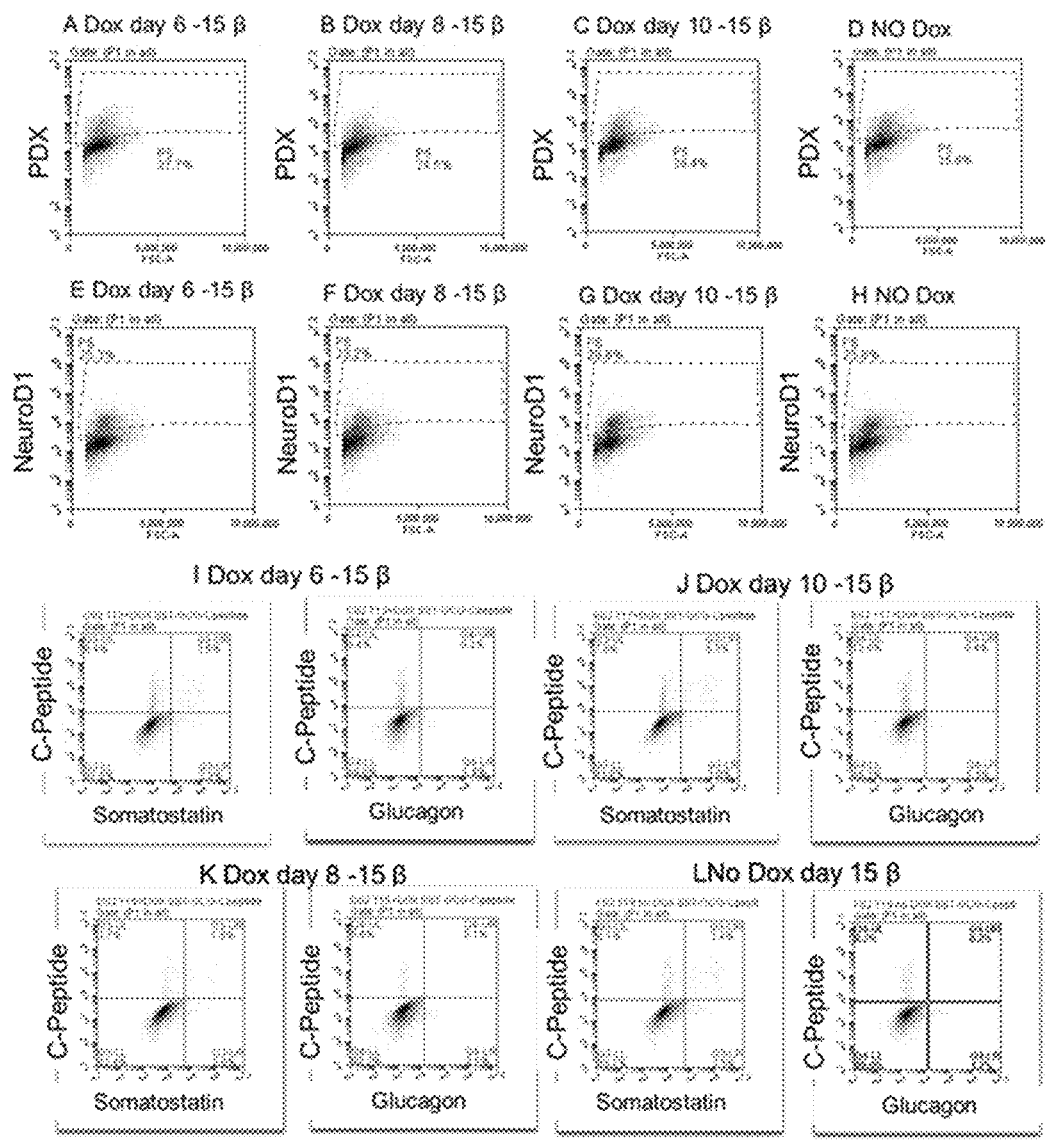
FIGs. 27A-L

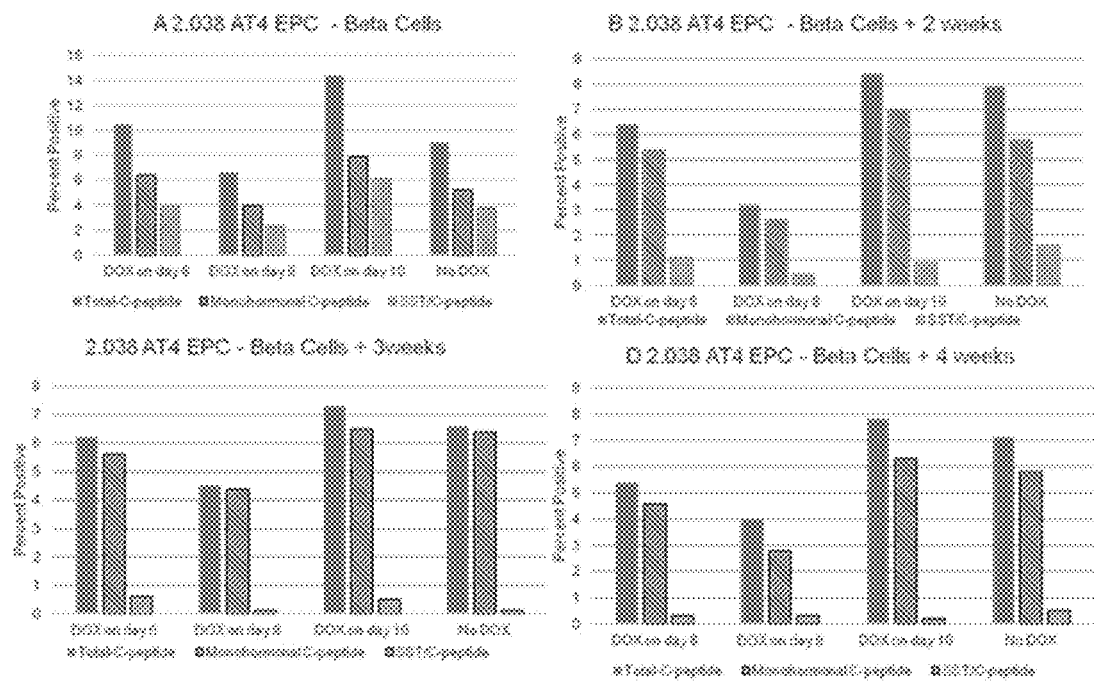
FIGs. 29A-D

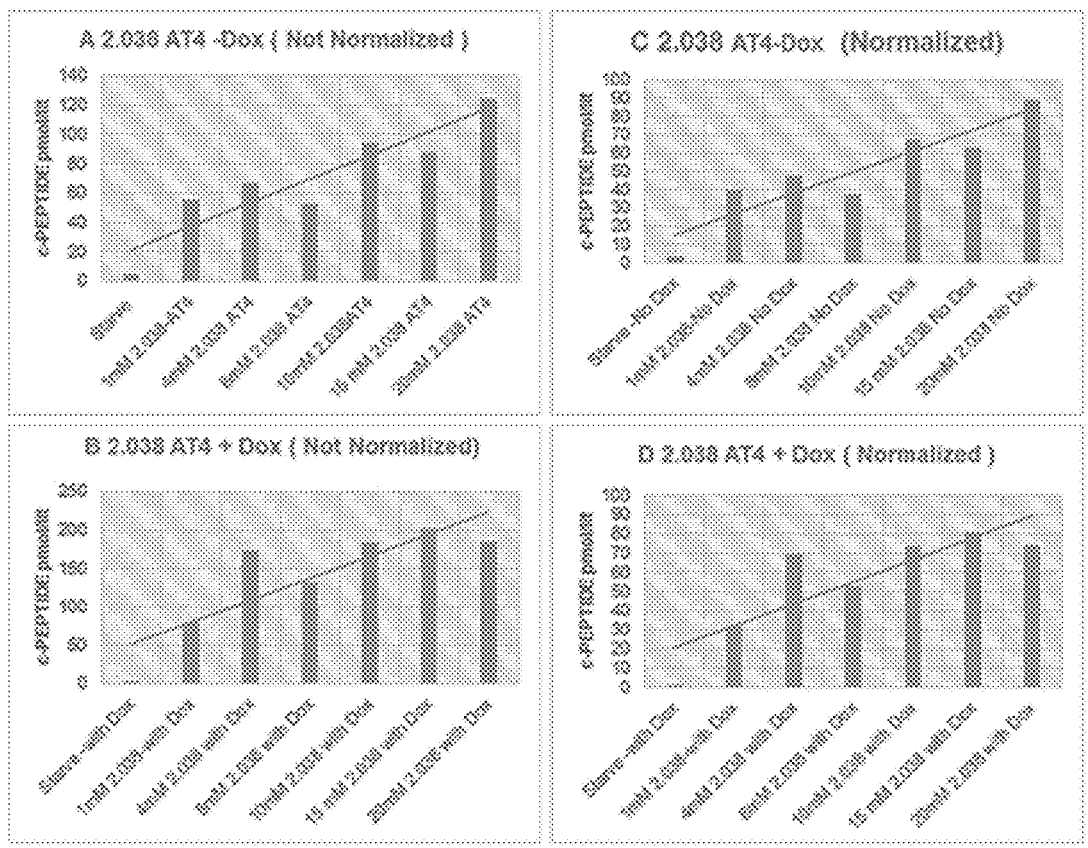
FIGs. 30A-D

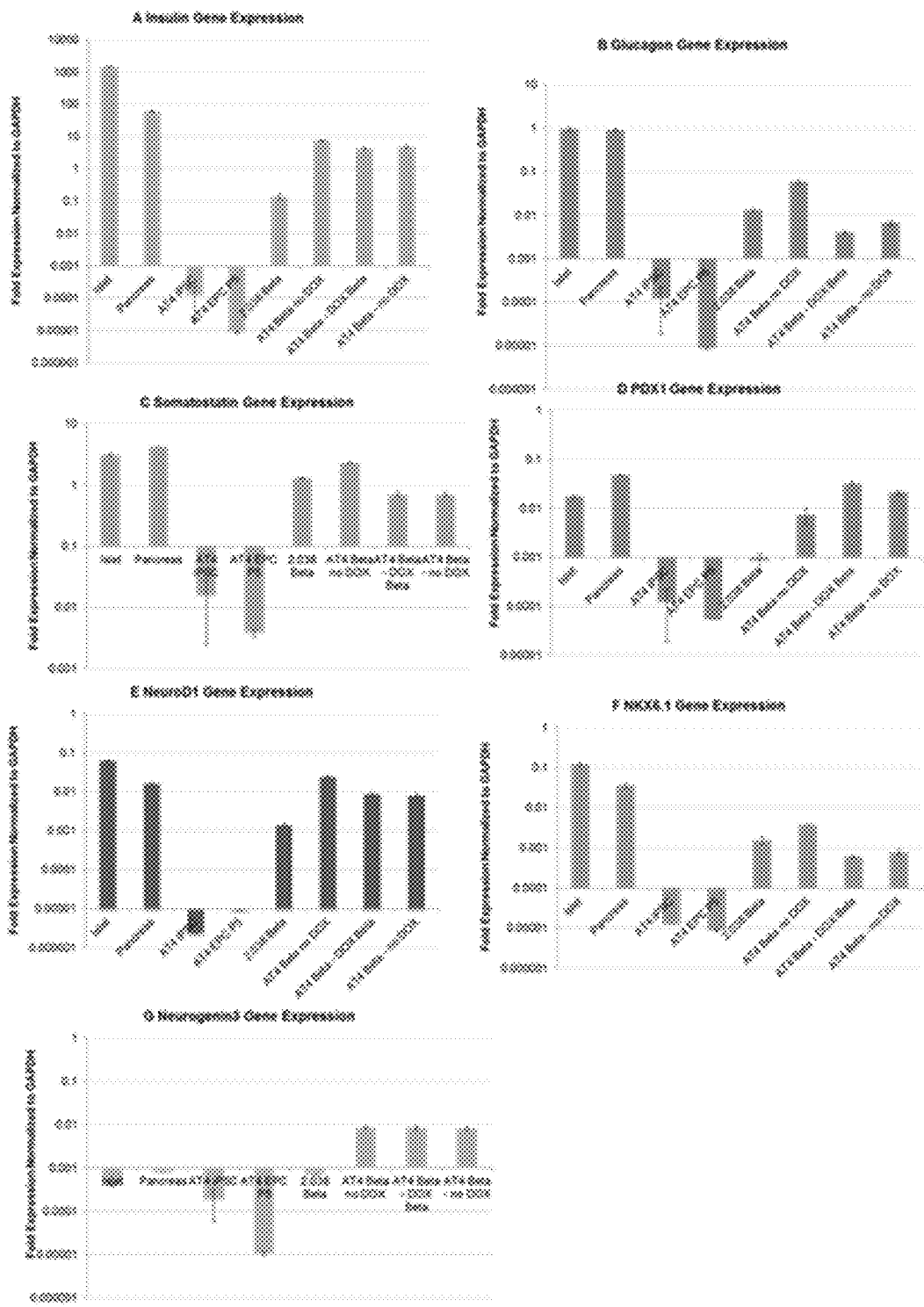
FIGs. 31A-G

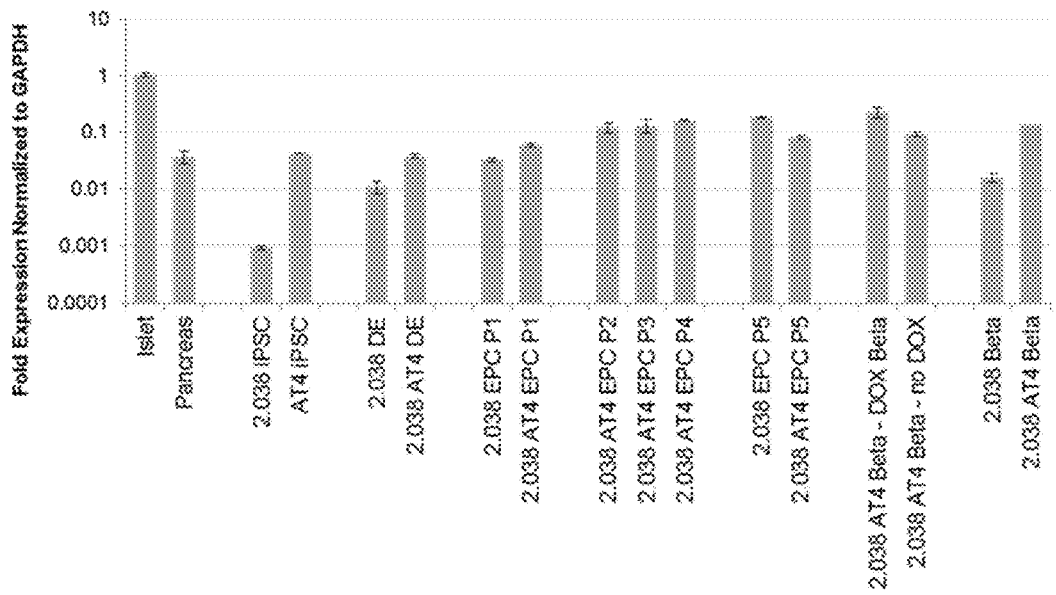
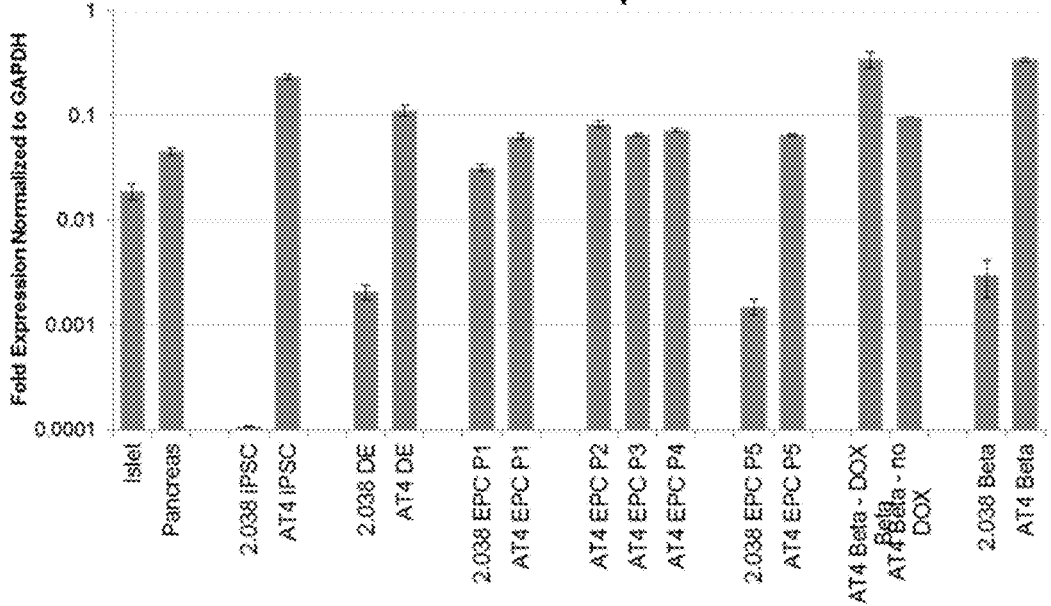
FIGs. 32A-B

METHODS AND COMPOSITIONS FOR CULTURING ENDODERM PROGENITOR CELLS IN SUSPENSION

The present application claims the priority benefit of U.S. provisional application No. 61/808,003, filed Apr. 3, 2013, the entire contents of which are incorporated herein by reference.

BACKGROUND OF THE INVENTION

1. Field of the Invention

The present invention relates generally to the fields of endocrinology, stem cells, and differentiated cells. More particularly, it concerns the production of self-renewing endoderm progenitor cells from undifferentiated cells in a suspension culture.

2. Description of Related Art

Endoderm-derived tissues, including pancreas, are potentially useful for cell replacement therapies. It is possible to generate definitive endoderm, which forms the primitive gut tube during development, and its derivative lineages from pluripotent stem cells (PSCs) in vitro through sequential exposure to cytokines that mimic embryonic morphogenesis. In this fashion, pancreatic cells can be produced from embryonic stem cells (ESCs) and induced pluripotent stem cells (iPSCs) (D'Amour et al., 2006; Gouon-Evans et al., 2006). While these studies highlight the promise of PSC-derived endodermal tissues for transplantation therapies, several obstacles remain. Endodermal cells generated from PSCs tend to display immature phenotypes and in many instances are not fully functional. For example, most pancreatic beta cells currently generated in vitro from human ESCs are poly-hormonal and not glucose responsive (D'Amour et al., 2006; Nostro et al., 2011). An additional obstacle in the production of endodermal cells for use in transplantation is the ability to scale the production to produce the required number of cells, which for pancreatic cells is currently limited by the necessity for production on a solid surface. It is an objective of the present invention to provide culture and isolation methods that avoid these limitations.

SUMMARY OF THE INVENTION

The present invention overcomes a major deficiency in the art by providing efficient methods for producing self-renewing endoderm progenitor cells (hereinafter, "EPCs," "EPs," or "EP cells"). In a first embodiment, a method for producing self-renewing endoderm progenitor cells is provided comprising a) culturing pluripotent stem cells in serum-free medium comprising Activin A or Nodal to effect the induction of endoderm cells and b) culturing the endoderm cells in a suspension culture with BMP4, VEGF, FGF2, and EGF, or homologs thereof, in serum-free medium to selectively promote the growth of self-renewing endoderm progenitor cells. In one embodiment, a method for producing self-renewing endoderm progenitor cells is provided comprising a) culturing pluripotent stem cells in serum-free medium comprising Activin A to effect the induction of endoderm cells and b) culturing the endoderm cells in a suspension culture with Activin A, BMP4, VEGF, FGF2, and EGF, or homologs thereof, in serum-free medium to selectively promote the growth of self-renewing endoderm progenitor cells. In some aspects, the suspension culture of step b) may further comprise TGFβ. In certain aspects, the endoderm cells comprise a population of definitive endoderm cells and endoderm progenitor cells. In some aspects, the endoderm cells in step b) are cultured in suspension at an initial concentration of about $10^4$, $10^5$, $10^6$, $10^7$, $10^8$ cells/ml, or any range derivable therein. Preferably the endoderm cells are cultured in suspension at an initial concentration of about 250,000-2,000,000 cells/ml and more preferably 250,000-500,000 cells/ml.

In some aspects, the serum-free medium in step a) may further comprise Wnt3A or a GSK3 inhibitor. In other aspects, the serum-free medium in step a) may not contain Wnt3A or a GSK3 inhibitor. A preferred example of a GSK3 inhibitor is CHIR 99021. In some aspects, the culturing in step a) may be carried out for at least or about 1, 2, 3, 4, 6, 7, 8, 9, 10, 11, 12, 13, 14, 15, 16, 17, 18, 19, 20 days, or any range derivable therein. Preferably, said culturing is carried out for about 4-12 days, more preferably for about 5-8 days. In some aspects, the culturing in step a) may be carried out as an adherent culture.

In some aspects, the endoderm progenitor promoting growth factors used in step b) may further comprise TGF-β, latent TGF-β binding proteins, Nodal, a GSK3 inhibitor, Follistatin-related protein (FSRP), Dickkopf-related protein 1, IndolactamV, and/or insulin-like growth factor. A preferred example of a GSK3 inhibitor is CHIR 99021. In some aspects, the culturing in step b) may be carried out for at least or about 1, 2, 3, 4, 6, 7, 8, 9, 10, 11, 12, 13, 14, 15, 16, 17, 18, 19, 20, 21, 22, 23, 24, 25 days, or any range derivable therein. In some aspects, said culturing in step b) may be carried out for at least 1, 2, 3, 4, 5, 6 months, or any range derivable therein. Preferably, said culturing is carried out for at least about 5 to about 40 days, more preferably for about 10 to about 15 days. In some aspects, the culturing in step b) may occur in the presence of a ROCK inhibitor. The ROCK inhibitor may be Y-27632, H1152, or HA-100. In some aspects, the ROCK inhibitor may be removed after the first about 12 hours of culture.

In some aspects, the suspension culture in step b) may further comprise matrix components, such as basement membrane preparations, to support culture of the cell population. Non-limiting examples of the matrix components include collagen, gelatin, poly-L-lysine, poly-D-lysine, vitronectin, laminin, PLO laminin, fibrin clot, fibronectin and mixtures thereof, for example, Matrigel™ and lysed cell membrane preparations. The basement membrane preparation may be present at a final concentration of about 0.06-0.6 mg/ml, preferably about 0.3-0.6 mg/ml.

In some aspects, the suspension cultures in step b) may be dissociated and reaggregated about every 1, 2, 3, 4, 6, 7, 8, 9, 10, 11, 12, 13, 14, 15, or any range derivable therein. Preferably, the suspension cultures may be dissociated and reaggregated about every 4-5 days. In some aspects, the suspensions cultures in step b) may be maintained in spinner flasks. The spinner flasks may be operated at about 40-70 rpm. In some aspects, the suspension cultures in step b) may be maintained as static suspension cultures.

In some aspects, the endoderm progenitor cells may express CXCR4, CD117 (c-KIT), and CD34. In some aspects, the endoderm progenitor cells may further express Sox17, FOXA1, FOXA2, and CD31. Said expression may be detected by protein expression analysis, for example ELISA or FACS analysis, or RNA expression analysis, for example qRT-PCR. In some aspects, the formation of self-renewing endoderm progenitor cells does not require the presence of MEF feeder layers or MEF-conditioned medium. In some aspects, the culturing occurs under normoxic conditions. In some aspects, the culturing occurs under hypoxic conditions. In some aspects, the pluripotent stem cells may be maintained under hypoxic conditions prior to step a).

In some aspects, the pluripotent stem cells may be embryonic stem cells or induced pluripotent stem cells. The stem cells may also include multipotent stem cells, oligopotent stem cells, or unipotent stem cells. The stem cells may also include fetal stem cells or adult stem cells, such as hematopoietic stem cells, mesenchymal stem cells, neural stem cells, epithelial stem cells, and skin stem cells. In certain aspects, the stem cells may be isolated from umbilical, placenta, amniotic fluid, chorion villi, blastocysts, bone marrow, adipose tissue, brain, peripheral blood, cord blood, menstrual blood, blood vessels, skeletal muscle, skin, and liver.

In certain aspects, the method further comprises culturing the endoderm progenitor cells with islet beta cell promoting growth factors to effect the formation of mono-hormonal pancreatic islet beta cells. In some aspects, the endoderm progenitor cells may be purified prior to culturing. Said purification may be based on expression of markers, such as CD34, CD117, and CXCR4. In certain aspects, the culturing may be performed as a suspension culture. In some aspects, the culturing may be performed as an adherent culture. The islet beta cell promoting growth factors may comprise a potent inhibitor of AMP-activated protein kinase (AMPK), a BMP antagonist, a hedgehog inhibitor, a gamma-secretase inhibitor, an ALK5 inhibitor, retinoic acid, FGF10, B27, and Wnt3A or a GSK3 inhibitor. A preferred example of a GSK3 inhibitor is CHIR 99021. In some aspects, said further culturing may occur in the presence of a ROCK inhibitor. The ROCK inhibitor may be Y-27632, H1152, or HA-100.

In certain aspects, the method of effecting the formation of mono-hormonal pancreatic islet beta cells further comprises i) culturing the endoderm progenitor cells with a BMP antagonist, Wnt3A, and FGF10 to effect the formation of foregut endoderm cells; ii) culturing the foregut endoderm cells with B27, a BMP antagonist, a Hedgehog inhibitor, retinoic acid, and FGF10 to effect the formation of pancreatic endoderm cells; iii) culturing the pancreatic endoderm cells with B27, a BMP antagonist, a gamma-secretase inhibitor, and an ALK5 inhibitor to effect the formation of endocrine precursor cells; and iv) culturing said endocrine precursor cells with a BMP antagonist, an ALK5 inhibitor, insulin, glucose, and nicotinamide to effect the formation of mono-hormonal pancreatic islet beta cells.

The BMP antagonist used in step i) may be dorsomorphin or LDN-193189. Preferably, the BMP antagonist is dorsomorphin. The BMP antagonist used in steps ii), iii), and iv) may be Noggin, Gremlin, USAG-1, Follistatin, PRDC, Cerberus, Coco, Sclerostin, or Chordin. Preferably, the BMP antagonist is Noggin. The gamma-secretase inhibitor used in step iii) may be DAPT, R04929097, BMS-708163, Semagacestat, MK-0752, YO-01027, LY-411575, or (R)-flurbiprofen. Preferably, the gamma-secretase inhibitor is DAPT. The ALK5 inhibitor used in steps iii) and iv) may be SB431542, ALX-270-448, A 83-01, EW-7195, K126894, LY2109761, LY-364947, SB-525334, SB-505124, SD-208, IN-1233, or SK12162. Preferably, the ALK5 inhibitor is SB431542. The Hedgehog inhibitor used in step ii) may be KAAD-cyclopamine, vismodegib, LY2940680, MRT-10, MRT-83, or GDC-0449. Preferably, the Hedgehog inhibitor is KAAD-cyclopamine.

In some aspects, the cells may comprise an inducible expression cassette encoding Erg1. In certain aspects, step iv) of the method of effecting the formation of mono-hormonal pancreatic islet beta cells may further comprise inducing the cells to express Erg1. In some aspects, the cells may comprise an inducible expression cassette encoding Gfi1. In certain aspects, step iv) of the method of effecting the formation of mono-hormonal pancreatic islet beta cells may further comprise inducing the cells to express Gfi1. In some aspects, the cells may comprise inducible expression cassettes encoding both Erg1 and Gfi1. In certain aspects, step iv) of the method of effecting the formation of mono-hormonal pancreatic islet beta cells may further comprise inducing the cells to express both Erg1 and Gfi1. In various aspects, the inducible expression cassette may be integrated into the genome of the cells. In various aspects, the inducible expression cassette may be comprised in a transposon (e.g. piggyBac). In various aspects, the inducible expression cassette may be comprised in an episomal vector.

In some aspects, the culturing in steps i), ii), and iii) may be carried out for at least or about 1, 2, 3, 4, 6, 7, 8, 9, 10, 11, 12, 13, 14, 15, 16, 17, 18, 19, 20 days, or any range derivable therein. Preferably, said culturing is carried out for about 3-5 days. In some aspects, the culturing in step iv) may be carried out for at least or about 1, 2, 3, 4, 6, 7, 8, 9, 10, 11, 12, 13, 14, 15, 16, 17, 18, 19, 20 days, or any range derivable therein. Preferably, said culturing is carried out for about 3-40 days.

In some aspects, the culture may comprise a basement membrane preparation. In some aspects, the culture may occur under hypoxic conditions. In some aspects, the culture may be devoid of MEF feeder cells and MEF-conditioned medium.

In some aspects, the mono-hormonal pancreatic islet beta cells may express PDX, insulin, C-peptide, and NeuroD1, low levels of somatostatin and Nkx6.1, and no glucagon. Said expression may be detected by protein expression analysis, such as ELISA or FACS analysis, or RNA expression analysis, such as qRT-PCR. In some aspects, the mono-hormonal pancreatic islet beta cells are at least 1%, 5%, 10%, 15%, 20%, 25%, 30%, 35%, 40%, 45%, 50%, 60%, 70%, 80%, 85%, 90%, 91%, 92%, 93%, 94%, 95%, 96%, 97%, 98%, 99%, 99.9% (or any intermediate ranges) of the cell population, or any range derivable therein. Preferably, the mono-hormonal pancreatic islet beta cells are about 12% pure or about 20% pure. Additional characteristic of mono-hormonal pancreatic islet beta cells include, but are not limited to, glucose-responsive C-peptide release and the ability to revert diabetes in animal models thereof by pancreatic engraftment.

In some aspects, the mono-hormonal pancreatic islet beta cells may be cultured for one to four weeks. In certain aspects, said culturing may comprise a suspension culture.

In another embodiment, the present disclosure provides a method of producing self-renewing endoderm progenitor cell aggregates comprising a) culturing pluripotent stem cells in serum-free medium comprising Activin A or Nodal to effect the induction of endoderm cells and b) culturing the endoderm cells in a suspension culture with BMP4, VEGF, FGF2, and EGF or homologs thereof in serum-free medium to effect the formation of self-renewing endoderm progenitor cell aggregates.

In yet another embodiment, the present disclosure provides a method of producing self-renewing endoderm progenitor cell aggregates comprising a) culturing pluripotent stem cells in serum-free medium comprising Activin A to effect the induction of endoderm cells and b) culturing the endoderm cells in a suspension culture with Activin A, BMP4, VEGF, FGF2, EGF, and TGFβ or homologs thereof in serum-free medium to effect the formation of self-renewing endoderm progenitor cell aggregates.

In various aspects, the cells of the embodiments may be contacted with differentiation factors in an amount sufficient to cause differentiation of the stem cells to endoderm progenitor cells. The differentiation factors may comprise gene products of the differentiation factor genes. The gene products may be polypeptides or RNA transcripts of the differentiation factor genes. In a further aspect, the differentiation factors may comprise one or more protein transduction domains to facilitate their intracellular entry and/or nuclear entry. Such protein transduction domains are well known in the art, such as an HIV TAT protein transduction domain, HSV VP22 protein transduction domain, *Drosophila* Antennapedia homeodomain, or variants thereof.

In certain aspects, starting cells for the present methods may comprise at least or about $10^4$, $10^5$, $10^6$, $10^7$, $10^8$, $10^9$, $10^{10}$, $10^{11}$, $10^{12}$, $10^{13}$ cells or any range derivable therein. The starting cell population may have a seeding density of at least or about 10, $10^1$, $10^2$, $10^3$, $10^4$, $10^5$, $10^6$, $10^7$, $10^8$ cells/ml, or any range derivable therein.

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-D. Characterization of iPSC-derived cells that were cultured in medium comprising Activin A or Nodal. The plots represent surface staining of CXCR-4 and CD117 expression and the relevant isotype control staining FIG. 1A represents Forward and Side Scatter of the harvested cells. FIG. 1B depicts the live cells present in the population. FIG. 1C represents the staining profile of isotype control antibodies. FIG. 1D depicts cell surface staining of CXCR-4 and CD117 expression.

FIGS. 2A-G. Characterization of cells, including endoderm progenitor populations, derived from iPSCs maintained on E8 media. The plots represent intracellular staining of Sox17, FoxA1, and FoxA2 expression and the relevant isotype control staining FIG. 2A represents Forward and Side Scatter of the harvested cells. FIG. 2B depicts the live cells present in the population. FIGS. 2C and 2E represent the staining profile of isotype control antibodies. FIG. 2D depicts intracellular staining of FoxA1 and Sox17 expression. FIG. 2F depicts intracellular staining of FoxA2 expression. FIG. 2G depicts immunostaining of endoderm progenitor cells derived from iPSCs.

FIG. 8. Phase contrast images of 3D EPC aggregates placed in pancreatic differentiation media. Photographs were taken at 10× and 20× magnification.

FIG. 16A. Total viable cell yield at each time point. FIG. 16B. Efficiency of DE generation determined as a ratio of absolute number of DE cells/total cell number at each time point. FIG. 16C. The percentage of FoxA1-Sox17 expressing cells at each time point as quantified by intracellular flow cytometry. FIG. 16D. The percentage of CXCR4-CD117 expressing cells at each time point as quantified by surface staining.

FIGS. 18A-E. Matrigel preserves EPC while MEFs are not essential. FIG. 18A. The percentage of DE markers (i.e. CXCR4, CD117, FoxA2, and FoxA1) on cells from EPC cultures cultured with or without Matrigel was quantified by flow cytometry. Efficiency was determined as a ratio of absolute number of viable DE expressing cells/total viable cell number. FIG. 18B. Viable cell count for 2.038 clone 8777 cultured with or without MEFs. FIG. 18C. Purity of EPC for 2.038 clone 8777 cultured with or without MEFs. FIG. 18D. Viable cell count for 2.038 clone 8776 cultured with or without MEFs FIG. 18E. Purify of EPC for 2.038 clone 8776 cultured with or without MEFs.

FIG. 19A. Proliferation of EPCs during feeder free cycling. FIG. 19B. Average EPC purity during cycling. At each time point, the purity of EPC cultures were determined by flow cytometry. The average expression of CXCR4/CD117/FoxA1/FoxA2/Sox17 was quantified. Purities of EPCs from various experimental runs of the same iPSC clone were averaged and the standard error calculated.

FIGS. 20A-E. qPCR analysis of EPC cultures under defined feeder free hypoxic conditions. FIG. 20A. CXCR4 gene expression. FIG. 20B. CD117 gene expression. FIG. 20C. Sox17 gene expression. FIG. 20D. FoxA2 gene expression. FIG. 20E. FoxA1 gene expression.

FIG. 26A. Beta cells harvested on day 15 of differentiation were quantified for expression of PDX/NeuroD1/C-peptide/Glucagon/Somatostatin by intracellular flow cytometry. FIG. 26B. Non-normalized and normalized C-peptide release assay. Data were normalized to total viable cell number.

FIGS. 27A-L. Glucose responsiveness of end-stage beta cells generated from 2.038 AT4 cells. Dox was added at different stages of the beta cell differentiation process. Dox (1.5 ug/ml) induction performed during days 6-15 of beta cell differentiation, between days 8-15 of beta cell differentiation, or between days 10-15 of beta cell differentiation. The cells were harvested on day 15 of beta cell differentiation fixed and stained for quantification of PDX/NeuroD1/C-peptide/Glucagon/Somatostatin by intracellular flow cytometry. Analysis of emerging beta cells on day 15 revealed the presence of PDX (FIGS. 27A-D), NeuroD1 (FIGS. 27E-H), Somatostatin/Glucagaon/C-peptide (FIGS. 27I-L).

FIGS. 29A-D. Glucose responsiveness of end-stage beta cells generated from 2.038 AT4 cells. Dox was added at different stages of the beta cell differentiation process. The cells were harvested on day 15 of beta cell differentiation for quantification of PDX/NeuroD1/C-Peptide/Glucagon/Somatostatin by intracellular flow cytometry. The beta cells were placed in end stage media for an extended analysis of end stage beta cell cultures. The cultures revealed the presence of mono-hormonal cells for up to 4 weeks in culture.

FIGS. 30A-D. Glucose responsiveness of end-stage beta cells generated from 2.038 AT4 cells. Dox was added at different stages of the beta cell differentiation process. FIG. 30A. Non-normalized C-peptide release assay without Dox induction. FIG. 30B. Normalized C-peptide release assay without Dox induction. FIG. 30C. Non-normalized C-peptide release assay with Dox induction. FIG. 30D. Normalized C-peptide release assay with Dox induction. Normalization was based on the total viable cell number taken for each sample.

FIGS. 31A-G. qPCR analysis of end-stage beta cells generated from 2.038 AT4 cells. Dox was added at different stages of the beta cell differentiation process. FIG. 31A. Insulin gene expression. FIG. 31B. Glucagon gene expression. FIG. 31C. Somatostatin gene expression. FIG. 31D. PDX1 gene expression. FIG. 31E. NeuroD1 gene expression. FIG. 31F. Nkx6.1 gene expression. FIG. 31G. Neurogenin3 gene expression.

FIGS. 32A-B. qPCR analysis of iPSC/DE/EPC/beta cells from 2.038 parental and 2.038AT4 cells for ERG and GFI expression. FIG. 32A. ERG gene expression. FIG. 32B. GFI1 gene expression.

DESCRIPTION OF ILLUSTRATIVE EMBODIMENTS

Human embryonic stem cells (ESCs) and induced pluripotent stem cells (iPSCs) offer tremendous potential for both basic biology and cell-based therapies for a wide variety of diseases due to their ability to be expanded in vitro along with their potential to differentiate into any cell type in the body. Differentiation of ES/iPS cells appears to mimic the process of development that occurs during embryogenesis. These stem cell populations proceed down developmental intermediaries with successively restricted potential until mature cell types are generated. First, the primary germ layers, mesoderm, endoderm, and ectoderm, are formed that then further mature into derivative cell types. One endodermal-derived tissue type that is especially appealing for stem cell replacement therapy is beta cells of the pancreatic islet to treat type I diabetes. Currently, there is a critical shortage of islets for use in transplant settings. The ability to generate mature, functional tissue types for transplant is currently limited due to the necessity to differentiate pluripotent stem cells through all stages of development.

Figure 14:
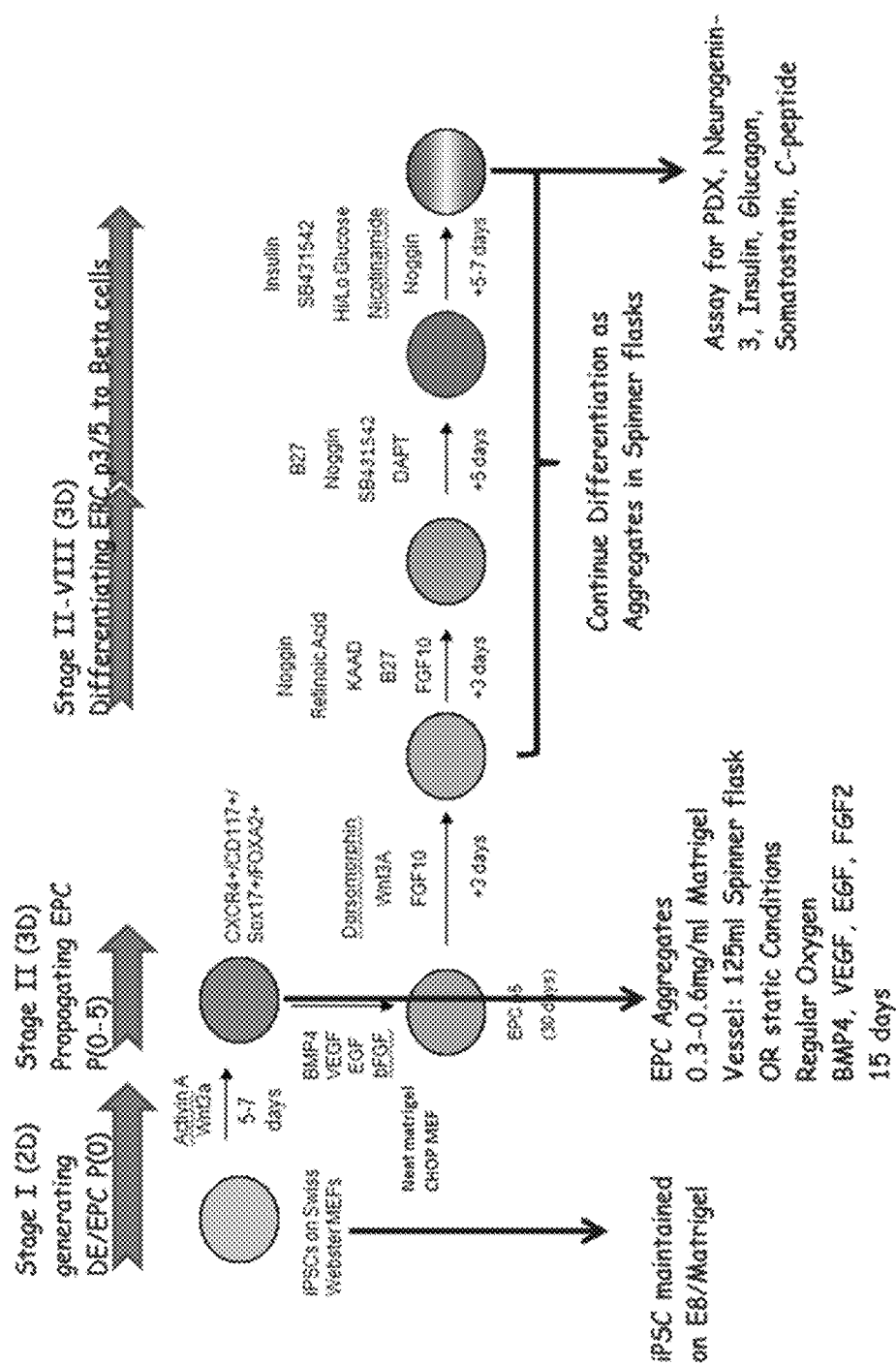
FIG. 14. Schematic representation of pancreatic differentiation process.
Figure 15:
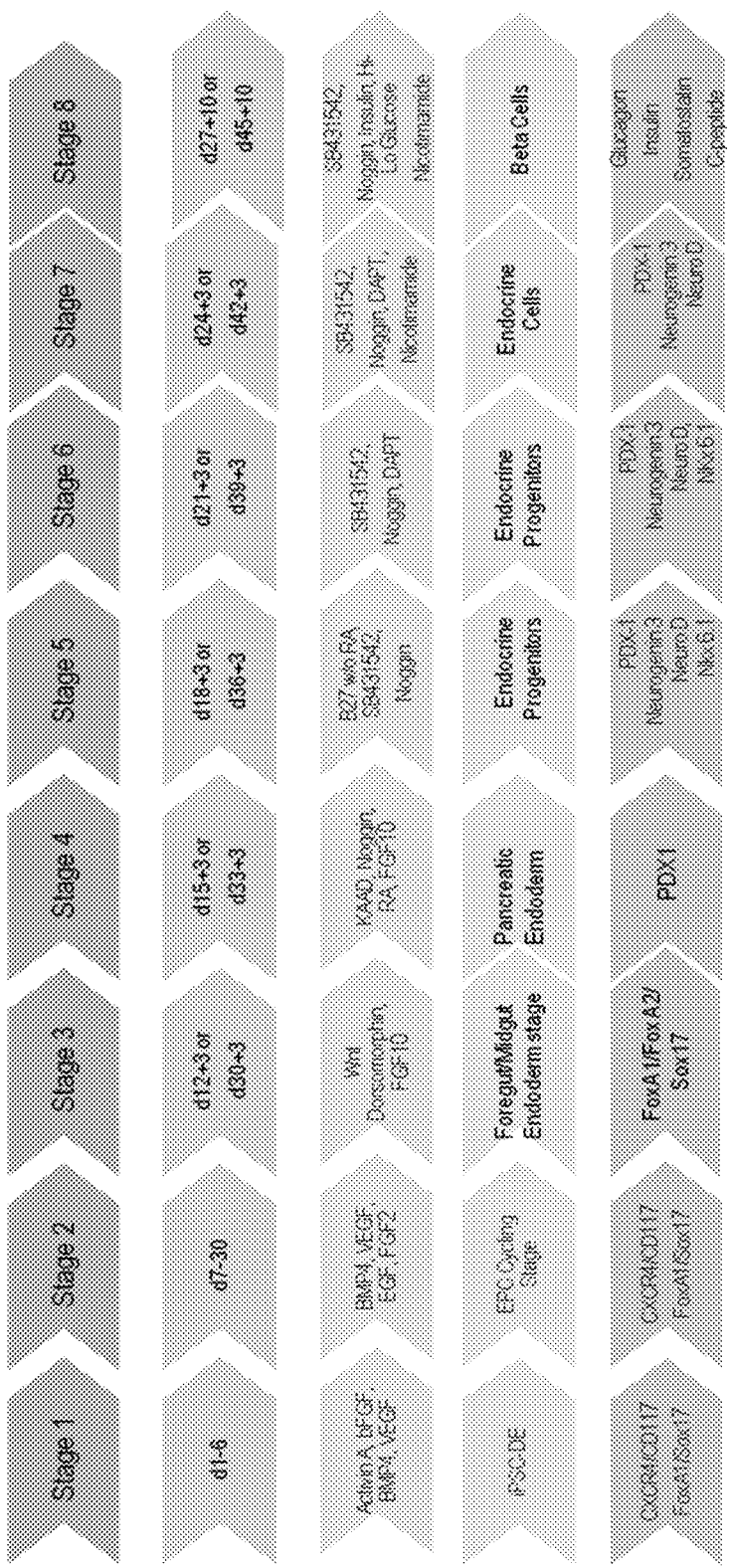
FIG. 15. General overview of the different stages of the pancreatic differentiation process. The rows, from top to bottom, represent the stage, the days during the process at which the stage occurs, the factors used in the differentiation process during the stage, the type of cell produced, and the markers of the type of cell produced.

Herein, a method is provided for the production of endoderm progenitor cells (EPCs) derived from induced pluripotent stem cells maintained under feeder-free conditions. The EP cells derived by this method are capable of generating mono-hormonal beta cells. A schematic representation of the process is provided in FIG. 14. The stages of the process are provided in FIG. 15.

Definitive endoderm (DE) is a transient state that quickly differentiates, cannot be proliferated, does not have a distinct morphology, and may not be fully committed to an endoderm fate. On the other hand, endoderm progenitor (EP) cells (or EPCs) are not transient, have a distinct morphology, and may be cultured indefinitely (Cheng et al., 2013). Endoderm progenitor cells are also characterized as expressing CXCR4, CD117, FOXA1, FOXA2, CD31, CD34, and SOX17. Endoderm progenitor cells can generate cells in the endoderm lineage, such as liver, pancreas, and intestine, but cannot generate mesoderm or ectoderm either in vitro or in vivo. Likewise, EP cells do not form teratomas in immune-deficient mice. Therefore, DE and EP cells may represent distinct developmental intermediaries and may have different development potentials.

iPSC-derived EP cells express CXCR-4, CD117, SOX17, FOXA1, FOXA2, CD34, CD31, and HNF4A and can be maintained in suspension cultures for 5-40 days. EPs expand and maintain the phenotypic expression of markers as 3D aggregates in spinner or static conditions in the presence of Matrigel, BMP4, VEGF, FGF, EGF2, Activin, and optionally TGFβ. EP cultures, when placed in culture conditions for generating cells of the pancreatic lineage, generate mono-hormonal beta cells functionally responsive to stimulation with D-glucose.

In summary, a culture procedure for efficiently generating EP cells from human iPSCs maintained in serum-free media is provided. EP cells retain their phenotypic characteristics and expand as 3D cultures for at least 30 days. EP cells placed in pancreatic differentiation media generate mono-hormonal beta cells. These cells will serve as an ideal cell type for high-throughput screening applications and hold potential for use in therapeutic applications.

I. Definitions

"Differentiation" is a process by which a less specialized cell becomes a more specialized cell to form progeny of at least one new cell type, either in culture or in vivo, than it would have under the same conditions without differentiation. "Dedifferentiation" is a cellular process in which a partially or terminally differentiated cell reverts to an earlier developmental stage, such as pluripotency or multipotency. "Transdifferentiation" is a process of transforming one differentiated cell type into another differentiated cell type. Under certain conditions, the proportion of progeny with characteristics of the new cell type may be at least about 1%, 5%, 25% or more in order of increasing preference.

"Multipotent" implies that a cell is capable, through its progeny, of giving rise to several different cell types found in an adult animal.

"Pluripotent" implies that a cell is capable, through its progeny, of giving rise to all the cell types that comprise the adult animal, including the germ cells. Embryonic stem cells, induced pluripotent stem cells, and embryonic germ cells are pluripotent cells under this definition.

The term "autologous cells" as used herein refers to donor cells that are genetically compatible with the recipient.

The term "totipotent" as used herein can refer to a cell that gives rise to a live born animal. The term "totipotent" can also refer to a cell that gives rise to all of the cells in a particular animal. A totipotent cell can give rise to all of the cells of an animal when it is utilized in a procedure for developing an embryo from one or more nuclear transfer steps.

Totipotent cells may also be used to generate incomplete animals, such as those useful for organ harvesting, e.g., having genetic modifications to eliminate growth of an organ or appendage by manipulation of a homeotic gene. Additionally, genetic modification rendering oocytes, such as those derived from ES cells, incapable of development in utero would ensure that human-derived ES cells could not be used to derive human oocytes for reproduction and only for applications such as therapeutic cloning.

The term "embryonic stem cell" as used herein can refer to pluripotent cells isolated from an embryo that are maintained in in vitro cell culture. Such cells are rapidly dividing cultured cells isolated from cultured embryos that retain in culture the ability to give rise, in vivo, to all the cell types that comprise the adult animal, including the germ cells. Embryonic stem cells may be cultured with or without feeder cells. Embryonic stem cells can be established from embryonic cells isolated from embryos at any stage of development, including blastocyst stage embryos and pre-blastocyst stage embryos. Embryonic stem cells may have a rounded cell morphology and may grow in rounded cell clumps on feeder layers. Embryonic stem cells are well known to a person of ordinary skill in the art. See, e.g., WO 97/37009; Yang & Anderson (1992); Piedrahita et al. (1998);

Wianny et al. (1997); Moore & Piedrahita (1997); Moore & Piedrahita (1996); Wheeler (1994); Hochereau-de Reviers & Perreau (1993); Strojek et al. (1990); Piedrahita et al. (1990); and Evans et al. (1990).

The term "reprogramming" or "reprogrammed" as used herein may refer to materials and methods that can convert a more specialized cell into a pluripotent cell.

The term "isolated" as used herein can refer to a cell that is mechanically separated from another group of cells. Examples of a group of cells are a developing cell mass, a cell culture, a cell line, and an animal.

The term "differentiated cell" as used herein can refer to a precursor cell that has developed from an unspecialized phenotype to a specialized phenotype. For example, embryonic cells can differentiate into an epithelial cell lining of the intestine. Differentiated cells can be isolated from a fetus or a live born animal, for example.

The term "undifferentiated cell" as used herein can refer to a precursor cell that has an unspecialized phenotype and is capable of differentiating. An example of an undifferentiated cell is a stem cell.

II. Cells Involved in Endoderm Progenitor Cell Formation

In certain embodiments of the invention, there are disclosed methods and compositions for providing endoderm progenitor cells from pluripotent cells. In some embodiments, the cells may be stem cells, including but not limited to, embryonic stem cells, fetal stem cells, adult stem cells, or induced pluripotent stem cells.

A. Stem Cells

Stem cells are cells found in most, if not all, multi-cellular organisms. They are characterized by the ability to self-renew through mitotic cell division and the ability to differentiate into a diverse range of specialized cell types. The two broad types of mammalian stem cells are embryonic stem cells that are found in blastocysts and adult stem cells that are found in adult tissues. In a developing embryo, stem cells can differentiate into all of the specialized embryonic tissues. In adult organisms, stem cells and progenitor cells act as a repair system for the body, replenishing specialized cells, and also maintain the normal turnover of regenerative organs, such as blood, skin, or intestinal tissues.

Human embryonic stem cells (ESCs) and induced pluripotent stem cells (iPSCs) are capable of long-term proliferation in vitro, while retaining the potential to differentiate into all cell types of the body, including endoderm progenitor cells and pancreatic islet beta cells. Endoderm progenitor cells could potentially provide an unlimited supply of patient-specific functional pancreatic islet beta cells for both drug development and therapeutic uses. The differentiation of human ESCs/iPSCs to pancreatic islet beta cells through endoderm progenitor cells in vitro recapitulates normal in vivo development, i.e. they undergo the normal sequential developmental stages including endoderm differentiation and endocrine specification. That sequential developmental process requires the addition of different growth factors at different stages of differentiation. Certain aspects of the invention provide fully functional pancreatic islet beta cells by differentiating human ESCs/iPSCs. This approach generates pancreatic islet beta cells with functions highly similar, if not identical, to human primary adult beta cells. In addition, the endoderm progenitor cells of the invention, with their unlimited proliferation ability, have unique advantages as the starting cell population for beta cell differentiation.

1. Embryonic Stem Cells

Embryonic stem cells (ES cells) are pluripotent stem cells derived from the epiblast tissue of the inner cell mass of a blastocyst or earlier morula stage embryo. ES cells are distinguished by two distinctive properties: their pluripotency and their capability to self-renew indefinitely. ES cells are pluripotent, that is, they are able to differentiate into all derivatives of the three primary germ layers: ectoderm, endoderm, and mesoderm. Additionally, under defined conditions, embryonic stem cells are capable of propagating themselves indefinitely. This allows embryonic stem cells to be employed as useful tools for both research and regenerative medicine, because they can produce limitless numbers of themselves for continued research or clinical use. ES cells can develop into each of the more than 200 cell types of the adult body when given sufficient and necessary stimulation for a specific cell type. They do not, however, contribute to the extra-embryonic membranes or the placenta.

Nearly all research to date has taken place using mouse embryonic stem cells (mES) or human embryonic stem cells (hES). Both have the essential stem cell characteristics, yet they require very different environments in order to maintain an undifferentiated state. Mouse ES cells may be grown on a layer of gelatin and require the presence of Leukemia Inhibitory Factor (LIF). Human ES cells could be grown on a feeder layer of mouse embryonic fibroblasts (MEFs) and often require the presence of basic Fibroblast Growth Factor (bFGF or FGF-2). Without optimal culture conditions or genetic manipulation (Chambers et al., 2003), embryonic stem cells will rapidly differentiate.

A human embryonic stem cell may also be defined by the presence of several transcription factors and cell surface proteins. The transcription factors Oct-4, Nanog, and Sox-2 form the core regulatory network that ensures the suppression of genes that lead to differentiation and the maintenance of pluripotency (Boyer et al., 2005). The cell surface antigens most commonly used to identify hES cells include the glycolipids SSEA3 and SSEA4 and the keratan sulfate antigens Tra-1-60 and Tra-1-81.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al., 2000). In one method, day-5 human blastocysts are exposed to rabbit anti-human spleen cell antiserum, and then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having an undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel™ or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson and Marshall, 1998; Thomson et al., 1995; Thomson and Odorico, 2000).

Another source of ES cells is established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13, and H14 were established by Thompson et al. (1995). In addition, subclones H9.1 and H9.2 of the H9 line have been developed. It is anticipated that virtually any ES or stem cell line known in the art may be used with the present invention, such as, e.g., those described in Yu and Thompson (2008), which is incorporated herein by reference.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

2. Induced Pluripotent Stem Cells

Induced pluripotent stem cells, commonly abbreviated as iPS cells or iPSCs, are a type of pluripotent stem cell artificially derived from a non-pluripotent cell, typically an adult somatic cell. Induced pluripotent stem cells are believed to be similar if not identical to natural pluripotent stem cells, such as embryonic stem cells in many respects, such as in terms of the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed.

iPS cells are obtained by reprogramming of differentiated somatic cells. Generation of induced pluripotent cells derived from human tissue other than of embryonic origin is desired to alleviate ethical concerns regarding experimental use of embryos and embryonic tissue. The promise of therapeutic applications from induced pluripotent cells has been touted. Medical applications include treatments for Alzheimer's disease, diabetes and spinal cord injuries to name a few. Other applications include disease modeling and pharmaceutical drug screening.

Induced pluripotent stem cells have been obtained by various methods. Human fetal or newborn fibroblasts are transfected with four genes, Oct4, Sox2, Nanog and Lin28 using lentiviral transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage, and gut epithelium after injection into mice.

In another method, adult human dermal fibroblasts are transfected with transcription factors Oct4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF.

iPS cells were first produced in 2006 (Takahashi et al., 2006) from mouse cells and in 2007 from human cells (Takahashi et al., 2007; Yu et al, 2007). This has been cited as an important advancement in stem cell research, as it may allow researchers to obtain pluripotent stem cells, which are important in research and potentially have therapeutic uses, without the controversial use of embryos. The first successful demonstration of generating induced pluripotent cells (iPS cells) from mouse or human tissue involved the use of retroviral vectors expressing a specific set of transcription factors. Research in the laboratories of James Thomson and Shinya Yamanaka has demonstrated that introduction of specific transcription factors by retroviral vectors into mouse or human fibroblasts is sufficient to reprogram those cells to undifferentiated pluripotent stems cells. The factors used by Thomson include Oct4, Sox2, Nanog and Lin28. The factors used by Yamanaka include Oct4, Sox2, Klf4 and c-Myc. Reprogramming via either gene set is accomplished by integration into the host cell genome and expression of the transcription factors or expression from episomal plasmids that can then be lost from the reprogrammed cell resulting in a scarless iPS cell.

Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having endoderm progenitor cell or pancreatic islet beta cell structures and markers. It is anticipated that virtually any iPS cells or cell lines may be used with the present invention, including, e.g., those described in Yu and Thompson, 2008.

Methods of preparing induced pluripotent stem cells from mouse are also known (Takahashi and Yamanaka, 2006). Induction of iPS cells typically requires the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog, and optionally, Lin-28; or comprising Sox-2, Oct4, Klf, and optionally, c-Myc.

iPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of iPS cells can be confirmed by injecting approximately $0.5$-$10 \times 10^6$ cells into the rear leg muscles of 8-12 week old male SCID mice. Teratomas develop that demonstrate at least one cell type of each of the three germ layers.

In certain aspects of the present invention, iPS cells are made from reprogramming somatic cells using reprogramming factors comprising an Oct family member and a Sox family member, such as Oct4 and Sox2 in combination with Klf and/or Nanog as described above and as described in WO2009/149233. The somatic cell for reprogramming may be any somatic cell that can be induced to pluripotency, such as a fibroblast, a keratinocyte, a hematopoietic cell, a mesenchymal cell, a liver cell, a stomach cell, or a β cell. In a certain aspect, T cells may also be used as source of somatic cells for reprogramming (see WO2010/141801, incorporated herein by reference).

Reprogramming factors may be expressed from expression cassettes comprised in one or more vectors, such as an integrating vector or an episomal vector, e.g., an EBV element-based system (see UWO2009/149233, incorporated herein by reference; Yu et al., 2009). In a further aspect, reprogramming proteins could be introduced directly into somatic cells by protein transduction.

2.038 AT4 cells are human iPSCs designed to induce hematopoiesis. They are engineered to constitutively express rtTET protein for inducible gene expression. The human Rosa26 locus on chromosome 3 was selected to allow the expression of rtTET. The LoxP recombination sites (LOX71 and LOX2272) were introduced into the first intron of the human ROSA26 gene via homologous recombination. A splicing acceptor signal from the human BCL2 gene (SA) was placed in front of the LOX71 site to allow the expression of selection markers from the endogenous human ROSA26 promoter. The neomycin phosphotransferase (Neo) was used for positive selection. The coding regions of ERG1 and GFI1 were cloned into the PiggyBac transposon-based expression vector under the control of the TET-inducible promoter (Ptight), which is an rtTET-responsive inducible promoter. ERG1 and GFI1 are under the control of the inducible promoter Ptight. To induce transgene expression, cells are treated with Doxycycline (DOX; 0.2 µg/ml). The correctly recombined inducible cells are resistant to puromycin (Puro+) and neomycin (Neo+).

2.038 MAFA cells are human iPSCs designed to overexpress the transcription factor MaFA. The plasmid contained the coding regions of MaFA fused to neomycin was electroporated in iPSCs. The emerging clones were selected using Neomycin selection. Exogenous MaFA is under the control of the TET-inducible promoter (Ptight), which is an rtTET-responsive inducible promoter present in the MaFa_Neomycin vector. To induce transgene expression, cells are treated with Doxycycline (DOX; 0.1-10 µg/ml). The correctly recombined inducible cells are resistant to neomycin (Neo+). The polyclonal population was subcloned further to derive 2.038Mafa cells.

III. Endoderm Progenitor (EP) Cell Characteristics

Cells can be characterized according to a number of phenotypic criteria. The criteria include but are not limited to the detection or quantitation of expressed cell markers, enzymatic activity, and the characterization of morphological features and intercellular signaling.

Endodermal cells embodied in certain aspects of this invention have morphological features characteristic of endoderm cells in nature. The features are readily appreciated by those skilled in evaluating such things, and include a doughnut-like morphology when grown in 2D cultures. One or more such features present in a single cell are consistent with the cell being a member of the endodermal cell lineage. Unbiased determination of whether cells have morphologic features characteristic of endodermal cells can be made by coding micrographs of differentiated progeny cells, adult or fetal endodermal cells, and one or more negative control cells, such as a fibroblast, or RPE (Retinal pigment epithelial) cells and then evaluating the micrographs in a blinded fashion, and breaking the code to determine if the endodermal cells from differentiation are accurately identified.

Definitive endoderm is a transient state that quickly differentiates, cannot be proliferated, does not have a distinct morphology, and may not be fully committed to an endoderm fate. On the other hand, endoderm progenitors are not transient, have a distinct morphology, and may be cultured indefinitely (Cheng et al., 2013). Endoderm progenitor cells can generate cells in the endoderm lineage, such as liver, pancreas, and intestine, but cannot generate mesoderm or ectoderm either in vitro or in vivo. Likewise, EP cells do not form teratomas in immune-deficient mice. Therefore, DE and EP cells may represent distinct developmental intermediaries and may have different development potentials.

The pancreas, an organ about the size of a hand, is located behind the lower part of the stomach. It comprises two structures that are both morphologically and physiologically different: the exocrine pancreas, which produces the enzymes involved in digestion (amylase, lipase, etc.) and sodium bicarbonate, and the endocrine pancreas, which produces the hormones involved in the control of blood glucose (insulin, glucagon, somatostatin, and pancreatic polypeptide). The cells of the endocrine pancreas are organized as micro-organs dispersed in the pancreas in the form of islets (islets of Langerhans or pancreatic islets). Each pancreatic islet is made up of four cell types: alpha cells, beta cells, delta cells and PP (gamma) cells and epsilon cells. The beta cells are found at the center of the islet and are the only cells capable of secreting insulin in response to glucose.

Cells of this invention can also be characterized according to whether they express phenotypic markers characteristic of the pancreatic endodermal lineage. Endoderm progenitor cells are also characterized as expressing CXCR4, CD117, FOXA1, FOXA2, CD31, CD34, and SOX17. Non-limiting examples of cell markers useful in distinguishing pancreatic islet beta cells include PDX-1, neurogenin3, neuroD1, insulin, glucagon, somatostatin, and C-peptide. Mature pancreatic islet beta cell markers include, but are not limited to, PDX1, C-peptide, and insulin. Immature pancreatic islet beta cells, which are akin to immature cells of the fetal pancreas, are poly-hormonal, while mature pancreatic islet beta cells are mono-hormonal and glucose-responsive.

Endoderm progenitor protein determinants listed in this disclosure can be detected using any suitable immunological technique—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be "antibody-detectable" if a significantly detectable amount of antibody will bind to the antigen in a standard immunocytochemistry or flow cytometry assay, optionally after fixation of the cells, and optionally using a labeled secondary antibody or other conjugate (such as a biotin-avidin conjugate) to amplify labeling.

The expression of specific markers can also be detected at the mRNA level by Northern blot analysis, dot-blot hybridization analysis, or by real-time polymerase chain reaction (PCR) using sequence-specific primers in standard amplification methods (U.S. Pat. No. 5,843,780). Sequence data for the particular markers listed in this disclosure can be obtained from public databases, such as GenBank. Expression at the mRNA level is said to be "detectable" according to one of the assays described in this disclosure if the performance of the assay on cell samples according to standard procedures in a typical controlled experiment results in clearly discernable hybridization or amplification product within a standard time window. Unless otherwise required, expression of a particular marker is indicated if the corresponding mRNA is detectable by RT-PCR. Expression of endoderm progenitor or beta cell-specific markers as detected at the protein or mRNA level is considered positive if the level is at least 2-fold, and preferably more than 10- or 50-fold above that of a control cell, such as an undifferentiated pluripotent stem cell, a fibroblast, or other unrelated cell type.

Cells can also be characterized according to whether they display enzymatic activity that is characteristic of cells of the pancreatic islet beta cell lineage. For example, the Glucose-Stimulated Insulin Secretion (GSIS) assay measures the C-peptide released in response to exposure to glucose stimulation. This assay gives a glucose stimulation index for each islet batch. The index is the ratio of insulin released at high glucose vs. low glucose concentrations.

In another aspect, the biological function of a beta cell provided by differentiation is evaluated, for example, by determining the level of insulin produced in response to glucose stimulation and in vivo rescue of diabetic mouse models upon transplantation of differentiated cells. In yet another aspect, beta cells may be identified by their high zinc content (Shiroi et al., 2002).

Endoderm progenitor cells may be testing using functional assays. For example, the cells may be transplanted into the endoderm compartment of a mouse embryo to test their ability to identify and interact with endogenous endoderm.

The skilled reader will readily appreciate that an advantage of culturing endoderm progenitor cells is that the cells can be grown in a homogenous undifferentiated cell population. As such, their use to generate downstream lineages may result in the increased efficiency of differentiation of more specialized cell types. This also reduces the potential of unwanted effects from contaminating cell types, such as those from other germ layers. EP cells of the invention can be characterized as essentially free of some or all contaminating cell types if less than 0.1% (preferably less than 100 or 10 ppm) bear markers or other features of the undesired cell type, as determined by immunostaining and fluorescence-activated quantitation, or other appropriate techniques. Moreover, EP cells may be free or essentially free of mesenchymal cells or hematopoietic cells.

Cells provided according to certain aspects of this invention can have a number of the features of cells obtained from primary sources. The more of these features that are present in a particular cell, the more it can be characterized as a cell of the endoderm progenitor cell lineage. Cells having at least 2, 3, 5, 7, or 9 of these features are increasingly more preferred. In reference to a particular cell population as may be present in a culture vessel or a preparation for administration, uniformity between cells in the expression of these features is often advantageous. In this circumstance, populations in which at least about 40%, 60%, 80%, 90%, 95%, or 98% of the cells have the desired features are increasingly more preferred.

IV. Endoderm Progenitor and Beta Cell Differentiation Factors

Certain aspects of the invention provide endoderm progenitor or beta cell differentiation factors. The inventors also contemplate that all the isoforms and variants of the genes listed in this section are included in this invention.

A. Cellular Signaling Inhibitors/Antagonists

In certain aspects of the invention, during at least part of the differentiation process, the cells may be maintained in the presence of one or more signaling inhibitors that inhibit a signal transducer involved in a signaling cascade. It will be understood that in these aspects and embodiments, other signaling inhibitors that inhibit a signaling component of the same signaling pathway may be substituted where desired. This may include inhibition of an upstream stimulus. Likewise, the inhibitor may be substituted where desired for other inhibitors of related signaling pathways.

Such a signaling inhibitor, e.g., a GSK3 inhibitor, an ALK5 inhibitor, a BMP antagonist, may be used at an effective concentration of at least or about 0.02, 0.05, 0.1, 0.2, 0.5, 1, 2, 3, 4, 5, 10, 15, 20, 25, 30, 35, 40, 45, 50, 100, 150, 200, 500 to about 1000 µM, or any range derivable therein.

A number of assays for identifying kinase inhibitors are known. For example, Davies et al. (2000) describes kinase assays in which a kinase is incubated in the presence of a peptide substrate and radiolabeled ATP. Phosphorylation of the substrate by the kinase results in incorporation of the label into the substrate. Aliquots of each reaction are immobilized on phosphocellulose paper and washed in phosphoric acid to remove free ATP. The activity of the substrate following incubation is then measured and provides an indication of kinase activity. The relative kinase activity in the presence and absence of candidate kinase inhibitors can be readily determined using such an assay. Downey et al. (1996) also describes assays for kinase activity which can be used to identify kinase inhibitors.

1. Glycogen Synthase Kinase 3 Inhibitors

Glycogen synthase kinase 3 (GSK3) is a serine/threonine protein kinase that mediates the addition of phosphate molecules on certain serine and threonine amino acids in particular cellular substrates. The phosphorylation of these other proteins by GSK3 usually inhibits the target protein (also called the "substrate"). As mentioned, GSK3 is known for phosphorylating and thus inactivating glycogen synthase. It has also been implicated in the control of cellular response to damaged DNA and Wnt signaling. GSK3 also phosphorylates Ci in the Hedgehog (Hh) pathway, targeting it for proteolysis to an inactive form. In addition to glycogen synthase, GSK3 has many other substrates. However, GSK3 is unusual among the kinases in that it usually requires a "priming kinase" to first phosphorylate a substrate.

The consequence of GSK3 phosphorylation is usually inhibition of the substrate. For example, when GSK3 phosphorylates another of its substrates, the NFAT family of transcription factors, these transcription factors cannot translocate to the nucleus and are therefore inhibited. In addition to its important role in the Wnt signaling pathway, which is required for establishing tissue patterning during development, GSK3 is also critical for the protein synthesis that is induced in settings such as skeletal muscle hypertrophy. Its role as an NFAT kinase also places it as a key regulator of both differentiation and cellular proliferation.

GSK3 inhibition may refer to inhibition of one or more GSK3 enzymes. The family of GSK3 enzymes is well-known and a number of variants have been described (see e.g. Schaffer et al., 2003). In specific embodiments GSK3-β is inhibited. GSK3-α inhibitors are also suitable, and in certain aspects inhibitors for use in the invention inhibit both GSK3-α and GSK3-β. GSK3 inhibitors can activate, for example, the Wnt/β-catenin pathway.

Specific examples of GSK3 inhibitors include, but are not limited to, Kenpaullone, 1-Azakenpaullone, CHIR99021, CHIR98014, AR-A014418 (see, e.g., Gould et al., 2004), CT 99021 (see, e.g., Wagman, 2004), CT 20026 (see, e.g., Wagman, 2004), SB415286, SB216763 (see, e.g., Martin et al., 2005), AR-A014418 (see, e.g., Noble et al., 2005), lithium (see, e.g., Gould et al., 2003), SB 415286 (see, e.g., Frame et al., 2001) and TDZD-8 (see, e.g., Chin et al., 2005). Further exemplary GSK3 inhibitors available from Calbiochem (see, e.g., WO2008/094597, herein incorporated by reference) include but are not limited to BIO (2'Z,3'£)-6-Bromomdirubm-3'-oxime (GSK3 Inhibitor IX); BIO-Acetoxime (2'Z,3'E)-6-Bromoindirubin-3'-acetoxime (GSK3 Inhibitor X); (5-Methyl-1H-pyrazol-3-yl)-(2-phenylquinazolin-4-yl)amine (GSK3-Inhibitor XIII); Pyridocarbazole-cyclopenadienylruthenium complex (GSK3 Inhibitor XV); TDZD-8 4-Benzyl-2-methyl-1,2,4-thiadiazolidine-3,5-dione (GSK3beta Inhibitor I); 2-Thio(3-iodobenzyl)-5-(1-pyridyl)-[1,3,4]-oxadiazole (GSK3beta Inhibitor II); OTDZT 2,4-Dibenzyl-5-oxothiadiazolidine-3-thione (GSK3beta Inhibitor III); alpha-4-Dibromoacetophenone (GSK3beta Inhibitor VII); AR-AO 14418 N-(4-Methoxy-benzyl)-N'-(5-nitro-1,3-thiazol-2-yl)urea (GSK-3beta Inhibitor VIII); 3-(1-(3-Hydroxypropyl)-1H-pyrrolo[2,3-b]pyridin-3-yl]-4-pyrazin-2-yl-pyrrole-2,5-dione (GSK-3beta Inhibitor XI); TWS1 19 pyrrolopyrimidine compound (GSK3beta Inhibitor XII); L803 H-KEAPP APPQSpP-NH2 or its Myristoylated form (GSK3beta Inhibitor XIII); 2-Chloro-1-(4,5-dibromo-thiophen-2-yl)-ethanone (GSK3beta Inhibitor VI); AR-AO144-18; SB216763; and SB415286.

The inhibitors used herein are preferably specific for the kinase to be targeted. Good results have been obtained with CHIR99021 which is specific for GSK3. Suitable concentrations for use of CHIR99021 are in the range 0.01 to 100, preferably 0.1 to 20, more preferably 0.3 to 10 micromolar.

2. ALK5 Inhibitors

TGF-β receptor inhibitors may include any inhibitors of TGF signaling in general or inhibitors specific for TGF-β receptor (e.g., ALK5) inhibitors, which can include antibodies to, dominant negative variants of, and siRNA and antisense nucleic acids that suppress expression of, TGF-β receptors. Exemplary TGF-β receptor/ALK5 inhibitors include, but are not limited to, SB431542 (see, e.g., Inman et al., 2002), A-83-01, also known as 3-(6-Methyl-2-pyridinyl)-N-phenyl-4-(4-quinolinyl)-1H-pyrazole-1-carbothioamide (see, e.g., Tojo et al., 2005, and commercially available from, e.g., Tocris Bioscience); 2-(3-(6-Methylpyridin-2-yl)-1H-pyrazol-4-yl)-1,5-naphthyridine, Wnt3a/BIO (see, e.g., WO 2008/094597, herein incorporated by reference), BMP4 (see, e.g., WO 2008/094597), GW788388 (−(4-[3-(pyridin-2-yl)-1H-pyrazol-4-yl]pyridm-2-yl}-N-(tetrahydro-2H-pyran-4-yl)benzamide) (see, e.g., Gellibert et al., 2006), SM16 (see, e.g., Suzuki et al., 2007), IN-1130 (3-((5-(6-methylpyridin-2-yl)-4-(quinoxalin-6-yl)-1H-imidazol-2-yl)methyl)benzamide) (see, e.g., Kim et al., 2008), GW6604 (2-phenyl-4-(3-pyridin-2-yl-1H-pyrazol-4-yl) pyridine) (see, e.g., de Gouville et al., 2006), SB-505124 (2-(5-benzo[1,3]dioxol-5-yl-2-tert-butyl-3H-imidazol-4-yl)-6-methylpyridine hydrochloride) (see, e.g., DaCosta et al., 2004); SU5416; lerdelimumb (CAT-152); metelimumab (CAT-192); GC-1008; ID1 1; AP-12009; AP-11014; LY550410; LY580276; LY364947; LY2109761; SB-431542; SD-208; SM16; NPC-30345; Ki26894; SB-203580; SD-093; ALX-270-448; EW-7195; SB-525334; IN-1233; SKI2162; Gleevec; 3,5,7,2',4'-pentahydroxyflavone (Morin); activin-M108A; P144; soluble TBR2-Fc; pyrimidine derivatives (see, e.g., those listed in WO 2008/006583, herein incorporated by reference); and indolinones reported in Roth et al. (2010).

Further, while an "ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman et al., 2002).

It is believed that inhibition of the TGF-β/activin pathway will have similar effects. Thus, any inhibitor (e.g., upstream or downstream) of the TGF-β/activin pathway can be used in combination with, or instead of, TGF-β/ALK5 inhibitors as described herein. Exemplary TGF-β/activin pathway inhibitors include but are not limited to: TGF-β receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described herein are merely for organizational purposes and one of skill in the art would know that compounds can affect one or more points within a pathway, and thus compounds may function in more than one of the defined categories.

3. ROCK Inhibitors

Pluripotent stem cells, especially human ES cells and iPS cells, are vulnerable to apoptosis upon cellular detachment and dissociation, which are important for clonal isolation or expansion and differentiation induction. Recently, a small class of molecules has been found to increase clonal efficiency and survival of dissociated pluripotent stem cells, such as Rho-associated kinase (ROCK) inhibitors, which are inhibitors for ROCK-related signaling pathways, for example, Rho-specific inhibitors, ROCK-specific inhibitors or myosin II-specific inhibitors. In certain aspects of the invention, ROCK inhibitors may be used for culturing and passaging of pluripotent stem cells and/or differentiation of the stem cells. Therefore, ROCK inhibitors could be present in any cell culture medium in which pluripotent stem cells grow, dissociate, form aggregates, or undergo differentiation, such as an adherent culture or suspension culture. Unless otherwise stated herein, myosin II inhibitors, such as blebbistatin, can substitute for the experimental use of ROCK inhibitors.

ROCK signaling pathways may include Rho family GTPases; ROCK, a major effector kinase downstream of Rho; Myosin II, the predominant effector downstream of ROCK (Harb et al., 2008); and any intermediate, upstream, or downstream signal processors. ROCK may phosphorylate and inactivate myosin phosphatase target subunit 1 (MYPT1), one of the major downstream targets of ROCK that negatively regulates myosin function through dephosphorylation of myosin regulatory light chain (MRLC).

ROCKs are serine/threonine kinases that serve as target proteins for Rho (of which three isoforms exist—RhoA, RhoB and RhoC). Theses kinases were initially characterized as mediators of the formation of RhoA-induced stress fibers and focal adhesions. The two ROCK isoforms—ROCK1 (p160ROCK, also called ROKβ) and ROCK2 (ROKα)—are comprised of an N-terminal kinase domain, followed by a coiled-coil domain containing a Rho-binding domain and a pleckstrin-homology domain (PH). Both ROCKs are cytoskeletal regulators, mediating RhoA effects on stress fiber formation, smooth muscle contraction, cell adhesion, membrane ruffling and cell motility. ROCKs may exert their biological activity by targeting downstream molecules, such as myosin II, myosin light chain (MLC), MLC phosphatase (MLCP) and the phosphatase and tensin homolog (PTEN).

Non-limiting examples of ROCK inhibitors include HA-100, Y-27632, H-1152, Fasudil (also referred to as HA1077), Y-30141 (described in U.S. Pat. No. 5,478,838), Wf-536, HA-1077, hydroxyl-HA-1077, GSK269962A, SB-772077-B, and derivatives thereof. Further, since other low molecular compounds are known as ROCK inhibitors, such compounds or derivatives thereof can be also used in embodiments (for example, refer to U.S. Patent Publication Nos. 2005/0209261, 2005/0192304, 2004/0014755, 2004/0002508, 2004/0002507, 2003/0125344 and 2003/0087919, and International Patent Publication Nos. 2003/062227, 2003/059913, 2003/062225, 2002/076976 and 2004/039796, which are hereby incorporated by reference). In certain aspects of the present invention, a combination of one or two or more of the ROCK inhibitors can also be used. Rho-specific inhibitors, such as Clostridium botulinum C3 exoenzyme, and/or Myosin II-specific inhibitors may also be used as a ROCK inhibitor in certain aspects of the invention.

4. BMP Pathway Antagonists

In one embodiment, the antagonist of the BMP signaling pathway (i.e. BMP signaling antagonist or BMP antagonist) inhibits or down regulates a constitutively active BMP signaling pathway. In one embodiment, the BMP signal pathway is a BMP2 or BMP4-mediated signaling pathway. In one embodiment, the antagonist of BMP signaling inhibits type I BMP receptor signal transduction. In one embodiment, the antagonist of the BMP signaling pathway inhibits the type I BMP receptor signal transduction by binding to the type I BMP receptor. In one embodiment, the type I BMP receptor includes ALK2, ALK3 or ALK6. In one embodiment, the antagonist of the BMP signaling pathway inhibits phosphorylation of SMAD 1, 5 or 8. In yet another embodiment, the antagonist of the BMP signaling pathway inhibits binding of BMP2 or 4 to a BMP receptor or interaction of a type II BMP receptor with a type I BMP receptor. The antagonist of the BMP signaling pathway is a chemical agent. Chemical agents may include, but are not limited to, dorsomorphin, LDN1 93189 and an analogue thereof. Polypeptide-derived BMP pathway antagonists include, but are not limited to, noggin, gremlin, chordin, follistatin, cerberus, PRDC, USAG-1, Coco, and sclerostin.

5. Hedgehog Inhibitors

Hedgehog inhibitors include, but are not limited to, KAAD-cyclopamine; GDC-0449; acylthiourea, acylurea, and acylguanidine derivates reported in (Solinas et al., 2012); phenyl quinazolinone ureas reported in (Brunton et al., 2008); cyclopamine analogues reported in (Winkler et al., 2009); AY9944, LY2940680, MRT-10, MRT-83, GDC-0449, triparanol, jervine, itraconzaole, sulfisomadine, podophyllum resin, colchicine. The term "hedgehog inhibitor" is meant to refer to an agent that will reduce the activity of smoothened, and reduce the activity of Hh pathway targets, patched and Gli 1. The term "hedgehog inhibitor" as used herein refers not only to any agent that may act by directly inhibiting the normal function of the hedgehog protein, but also to any agent that inhibits hedgehog pathway activity, and thus recapitulates the function of ptc.

6. Gamma Secretase Inhibitors

Active γ-secretase is a complex of four proteins, of which presenilin (PS) is thought to provide the active site through two highly-conserved aspartates, D257 and D385, located within transmembrane domains of the protein. To become active, immature PS must be processed and incorporated into a complex with other proteins to become stabilized. This includes a proteolytic cleavage by an enzyme termed "presenilinase" that produces N-terminal fragment and C-terminal fragments that remain associated with one another in the mature protease, with each fragment containing one of the two essential aspartates. Even this mature PS, however, is insufficient to cleave APP in the absence of the other members of the complex. These proteins, identified as nicastrin, Aph-1, and Pen-2, regulate maturation, stabilization and trafficking of the complex. Pen-2, for example, is required for the presenilinase cleavage of immature PS once it is incorporated into a complex with Aph-1 and nicastrin. Together, the complex of four proteins can reconstitute the γ-secretase activity, with PS alone sometimes itself referred to as "γ-secretase" based on its proposed role as the active core of the complex.

Among the most specific and effective γ-secretase inhibitors described so far is N-tN-fS.S-Difluorophenacetyl-L-alanyll-S-phenylglycine-f-butyl ester (DAPT), which inhibits both PS-1 and PS-2. DAPT is a cell-permeable dipeptide non-transition state analog that can compete moderately for the γ-secretase active site in a displacement assay, suggesting some overlap between the binding site of DAPT and the active site.

Peptidomimetic inhibitors include L-685,458 ((5S)-(t-Butoxycarbonylamino)-6-phenyl-(4R)hydroxy-(2R)benzyl-hexanoyl)-L-leu-L-phe-amide), described by Shearmen et al. (2000). ALX-260-127 is a reversible difluoro ketone peptidomimetic inhibitor of γ-secretase, described by Wolfe et al. (1998). Photoactivated gamma-secretase inhibitors directed to the active site of γ-secretase are described by Li et al. (2000). Sulindac sulfide (SSide) directly acts on gamma-secretase and preferentially inhibits the gamma-secretase activity in an in vitro gamma-secretase assay using recombinant amyloid beta precursor protein C100 as a substrate, Takahashi et al. (2003). Further examples of known gamma-secretase inhibitors include, but are not limited to, RO4929097, BMS-708163, Semagacestat, MK-0752, YO-01027, LY-411575, LY2811376, and (R)-flurbiprofen.

Various assays have also been described for screening γ-secretase inhibitors, for example by Takahashi et al., (2003), an assay based on detection of the putative C-terminal fragment-gamma of APP by Pinnix et al. (2000); cell free assays for γ-secretase activity by McLendon et al. (2000).

B. Differentiation Factors

Endoderm progenitor promoting growth factors illustrated in this disclosure may include soluble growth factors (peptide hormones, cytokines, ligand-receptor complexes, and other compounds) that are capable of promoting the growth of cells that can be further differentiated into monohormonal pancreatic beta cells. Non-limiting examples of such agents include, but are not limited to, growth factors, such as basic FGF (bFGF), BMP-4, EGF, Activin A, TGF-beta, and VEGF, or isoforms or variants thereof.

In certain embodiments, the one or more differentiation factor is BMP-4, which is important for the modulation of the proliferative and differentiation potential of hematopoietic progenitor cells (Bhardwaj et al., 2001; Bhatia et al., 1999; Chadwick 2003). BMP-4 can also promote the self-renewal of endoderm progenitor cells.

In further embodiments, the one or more differentiation factor is vascular endothelial growth factor (VEGF), which is an important signaling protein that is involved in formation of the embryonic circulatory system and angiogenesis. VEGF can affect a variety of cell types, including vascular endothelium and other cell types (e.g., neurons, cancer cells, kidney epithelial cells). VEGF function has also been shown to be important in a variety of disease states including cancer, diabetes, autoimmune diseases, and ocular vascular diseases.

Differentiation to provide endoderm progenitor and pancreatic islet beta cells may be accomplished by contacting cells with any one or more of the factors described in this section, including, but not limited to, Activin A, Nodal, Wnt3A, BMP4, VEGF, FGF2/bFGF, EGF, FGF10, B27, TGFbeta, nicotinamide, and retinoic acid. Also, Ets transcription factors, such as Erg-1, as well as GFI are known to be directly and/or indirectly involved in beta cell differentiation (Kobberup et al., 2007; Shroyer et al., 2005). Furthermore, without being bound by theory, HIF-1α, of which expression is induced by hypoxia, is known to be regulated beta cell function (Cheng et al., 2010).

V. Cell Culture

The term "cultured" as used herein in reference to cells can refer to one or more cells that are undergoing cell division or not undergoing cell division in an in vitro environment. An in vitro environment can be any medium known in the art that is suitable for maintaining cells in vitro, such as suitable liquid media or agar, for example. Specific examples of suitable in vitro environments for cell cultures are described in Culture of Animal Cells: a manual of basic techniques (1994); Cells: a laboratory manual (1998); and Animal Cells: culture and media (1994).

The term "cell line" as used herein can refer to cultured cells that can be passaged at least one time without terminating. The invention relates to cell lines that can be passaged indefinitely. Cell passaging is defined hereafter.

The term "suspension" as used herein can refer to cell culture conditions in which cells are not attached to a solid support. Cells proliferating in suspension can be stirred while proliferating using apparatus well known to those skilled in the art.

The term "monolayer" as used herein can refer to cells that are attached to a solid support while proliferating in suitable culture conditions. A small portion of cells proliferating in a monolayer under suitable growth conditions may be attached to cells in the monolayer but not to the solid support.

The term "plated" or "plating" as used herein in reference to cells can refer to establishing cell cultures in vitro. For example, cells can be diluted in cell culture media and then added to a cell culture plate, dish, or flask. Cell culture plates are commonly known to a person of ordinary skill in the art. Cells may be plated at a variety of concentrations and/or cell densities.

The term "cell plating" can also extend to the term "cell passaging." Cells of the invention can be passaged using cell culture techniques well known to those skilled in the art. The term "cell passaging" can refer to a technique that involves the steps of (1) releasing cells from a solid support or substrate and disassociation of these cells, and (2) diluting the cells in media suitable for further cell proliferation. Cell passaging may also refer to removing a portion of liquid medium containing cultured cells and adding liquid medium to the original culture vessel to dilute the cells and allow further cell proliferation. In addition, cells may also be added to a new culture vessel that has been supplemented with medium suitable for further cell proliferation.

The term "hypoxia" and "hypoxic conditions" as used herein can refer to conditions characterized by a lower oxygen concentration as compared to the oxygen concentration of ambient air (approximately 15%-20% oxygen). In one aspect, hypoxic conditions are characterized by an oxygen concentration less than about 10%. In another aspect hypoxic conditions are characterized by an oxygen concentration of about 1% to 10%, 1% to 9%, 1% to 8%, 1% to 7%, 1% to 6%, 1% to 5%, 1% to 4%, 1% to 3%, or 1% to 2%, or any range derivable therein.

The term "proliferation" as used herein in reference to cells can refer to a group of cells that can increase in number over a period of time.

The term "permanent" or "immortalized" as used herein in reference to cells can refer to cells that may undergo cell division and double in cell numbers while cultured in an in vitro environment a multiple number of times until the cells terminate. A permanent cell line may double over 10 times before a significant number of cells terminate in culture. Preferably, a permanent cell line may double over 20 times or over 30 times before a significant number of cells terminate in culture. More preferably, a permanent cell line may double over 40 times or 50 times before a significant number of cells terminate in culture. Most preferably, a permanent cell line may double over 60 times before a significant number of cells die in culture.

The starting cell and the differentiated cell generally have differing requirements for culture medium and conditions. It is usual to carry out at least an initial stage of culture, after introduction of the differentiation factors, in the presence of medium and under culture conditions known to be suitable for growth of the starting cell. This is followed by a subsequent period of culture in the presence of a differentiation medium and under conditions known to be suitable for the differentiated cell. After a sufficient time for differentiation, the differentiated cells may be further cultured for expansion of the differentiated cells in an expansion medium. Such an expansion medium may comprise one or more signaling inhibitors as described above or comprise a culture medium essentially free of these inhibitors.

The initial stage of culture is preferably for a period of up to 6 days, more preferably up to 4 days and in particular embodiments, described below for not more than 3 days, and more particularly up to or about one day. The subsequent stage of culture in differentiation medium comprising one or more signaling inhibitors is suitably for a period of at least or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 days, or any range derivable therein, and can be for a period of up to 120 days, preferably up to 10 days. In a specific embodiment described below used to generate endoderm progenitor or beta cells, the initial stage of culture was for a period of about 5 days and the subsequent stages were for about 26 to 44 days by culture in the presence of various differentiation media. The differentiation conditions may be essentially free of feeder cells. In further aspects, the differentiation medium may be chemically defined. To improve differentiation, the differentiation medium may further comprise high concentration of FGF and may be essentially free of TGF-β. In some instances, the medium may comprise TGF-β.

A. General Conditions

The culturing conditions according to the present invention will be appropriately defined depending on the medium and stem cells used. The medium according to certain aspects of the present invention can be prepared using a medium used for culturing animal cells as its basal medium, such as any of TeSR, Essential 8 medium, BME, BGJb, CMRL 1066, Glasgow MEM, Improved MEM Zinc Option, IMDM, Medium 199, Eagle MEM, αMEM, DMEM, Ham, RPMI 1640, and Fischer's media, as well as any combinations thereof, but the medium is not particularly limited thereto as far as it can be used for culturing animal cells.

The medium according to the present invention can be a serum-containing or serum-free medium. The serum-free medium refers to media with no unprocessed or unpurified serum, and accordingly can include media with purified blood-derived components or animal tissue-derived components (such as growth factors). From the aspect of preventing contamination with heterogeneous animal-derived components, serum can be derived from the same animal as that of the stem cell(s).

The medium according to the present invention may contain or may not contain any alternatives to serum. The alternatives to serum can include materials that appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolglycerol, or equivalents thereto. The alternatives to serum can be prepared by the method disclosed in International Publication No. 98/30679, for example. Alternatively, any commercially available materials can be used for more convenience. The commercially available materials include knockout Serum Replacement (KSR), Chemically-defined Lipid concentrated (Gibco), and Glutamax (Gibco).

The medium of the present invention can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and particularly about 0.1 to 0.5 mM, but the concentration is particularly not limited thereto as long as it is appropriate for culturing the stem cell(s).

A culture vessel used for culturing the cell(s) of the present invention can include, but is particularly not limited to: flask, flask for tissue culture, dish, petri dish, dish for tissue culture, multi dish, micro plate, micro-well plate, multi plate, multi-well plate, micro slide, chamber slide, tube, tray, Cell STACK® Chambers, culture bag, and roller bottle, as long as it is capable of culturing the cells therein. The stem cells may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, or any range derivable therein, depending on the needs of the culture. In a certain embodiment, the culture vessel may be a bioreactor, which may refer to any device or system that supports a biologically active environment. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel can be cellular adhesive or non-adhesive and selected depending on the purpose. The cellular adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, vitronectin, laminin, fibronectin, PLO laminin, fibrin, thrombin, and RetroNectin and mixtures thereof, for example, Matrigel™, and lysed cell membrane preparations (Klimanskaya et al., 2005).

Other culturing conditions can be appropriately defined. For example, the culturing temperature can be about 30-40° C., for example, at least or about 31, 32, 33, 34, 35, 36, 37, 38, 39° C. but particularly not limited to them. The $CO_2$ concentration can be about 1 to 10%, for example, about 2 to 5%, or any range derivable therein. The oxygen tension can be at least or about 1, 5, 8, 10, 20%, or any range derivable therein. The oxygen tension is preferably 20% for normoxic cultures. Normoxic and hypoxic culture conditions are described further below.

The methods of the present invention in certain aspects can be used for adhesion culture of cells, for example. In this case, the cells can be cultured in the presence of feeder cells. In the case where the feeder cells are used in the methods of the present invention, stromal cells such as fetal fibroblasts can be used as feeder cells (for example, refer to; Hogan et al., Manipulating the Mouse Embryo, A Laboratory Manual (1994); Gene Targeting, A Practical Approach (1993); Martin (1981); Evans and Kaufman (1981); Jainchill et al., (1969); Nakano et al. (1996); Kodama et al. (1982); and International Publication Nos. 01/088100 and 2005/080554).

The methods of the present invention in certain aspects can also be used for a suspension culture of cells, including suspension culture on carriers (Fernandes et al., 2004) or gel/biopolymer encapsulation (U.S. Publication 2007/0116680). The term suspension culture of the cells means that the cells are cultured under non-adherent condition with respect to the culture vessel or feeder cells (if used) in a medium. The suspension culture of cells includes a dissociation culture of cells and an aggregate suspension culture of cells. The term dissociation culture of cells means that suspended cells are cultured, and the dissociation culture of cells include those of single cells or those of small cell aggregates composed of a plurality of cells (for example, about 2 to 400 cells). When the aforementioned dissociation culture is continued, the cultured, dissociated cells form a larger aggregate of cells, and thereafter an aggregate suspension culture can be performed. The aggregate suspension culture includes an embryoid culture method (see Keller et al., 1995), and a SFEB method (Watanabe et al., 2005; International Publication No. 2005/123902).

The culture vessel used for culturing cells in suspension according to the method of some embodiments of the invention can be any tissue culture vessel with a suitable purity grade having an internal surface designed such that cells cultured therein are unable to adhere or attach to such a surface (e.g., non-tissue culture treated cells, to prevent attachment or adherence to the surface). Preferably, in order to obtain a scalable culture, culturing according to some embodiments of the invention is effected using a controlled culturing system (preferably a computer-controlled culturing system) in which culture parameters such as temperature, agitation, pH, and $pO_2$ is automatically performed using a suitable device. Once the culture parameters are recorded, the system is set for automatic adjustment of culture parameters as needed for promotion of cell expansion. Cells may be cultured under dynamic conditions (i.e., under conditions in which the cells are subject to constant movement while in the suspension culture) or under non-dynamic conditions (i.e., a static culture) while preserving their proliferative capacity. For non-dynamic culturing of cells, the cells can be cultured in uncoated 58 mm Petri dishes (Greiner, Frickenhausen, Germany). For dynamic culturing of cells, the cells can be cultured in spinner flasks (e.g., of 200 ml to 1000 ml, for example 250 ml; of 100 ml; or in 125 ml Erlenmeyer) which can be connected to a control unit and thus present a controlled culturing system. The culture vessel (e.g., a spinner flask, an Erlenmeyer) is shaken continuously. According to some embodiments of the invention the culture vessels are shaken at 90 rounds per minute (rpm) using a shaker. According to some embodiments of the invention the culture medium is changed daily.

B. Culturing Pluripotent Stem Cells

Cultures of pluripotent stem cells are described as "undifferentiated" when a substantial proportion of stem cells and their derivatives in the population display morphological characteristics of undifferentiated cells, clearly distinguishing them from differentiated cells of embryo or adult origin. Undifferentiated ES or iPS cells are recognized by those skilled in the art, and typically appear in the two dimensions of a microscopic view in colonies of cells with high nuclear/cytoplasmic ratios and prominent nucleoli. It is understood that colonies of undifferentiated cells can have neighboring cells that are differentiated.

ES cells can be maintained in an undifferentiated state by culturing the cells in the presence of serum and a feeder layer, typically mouse embryonic fibroblasts. Other methods for maintaining stem cells in an undifferentiated state are also known. For example, mouse ES cells can be maintained in an undifferentiated state by culturing in the presence of LIF without a feeder layer. However, unlike mouse ES cells, pre-existing human ES cells do not respond to LIF. Human ES cells can be maintained in an undifferentiated state by culturing ES cells on a feeder layer of fibroblasts in the presence of basic fibroblast growth factor (Amit et al., 2000), or by culturing on a protein matrix, such as Matrigel™ or laminin, without a feeder layer and in the presence of fibroblast-conditioned medium plus basic fibroblast growth factor (Xu et al., 2001; U.S. Pat. No. 6,833,269).

Methods for preparing and culturing ES cells can be found in standard textbooks and reviews in cell biology, tissue culture, and embryology, including teratocarcinomas and embryonic stem cells: A practical approach (1987); Guide to Techniques in Mouse Development (1993); Embryonic Stem Cell Differentiation in vitro (1993); Properties and uses of Embryonic Stem Cells: Prospects for Application to Human Biology and Gene Therapy (1998), all incorporated herein by reference. Standard methods used in tissue culture generally are described in Animal Cell Culture (1987); Gene Transfer Vectors for Mammalian Cells (1987); and Current Protocols in Molecular Biology and Short Protocols in Molecular Biology (1987 & 1995).

After somatic cells are introduced or contacted with reprogramming factors, these cells may be cultured in a medium sufficient to maintain the pluripotency and the undifferentiated state. Culturing of induced pluripotent stem (iPS) cells generated in this invention can use various medium and techniques developed to culture primate pluripotent stem cells, more specially, embryonic stem cells, as described in U.S. Pat. Publications 2007/0238170, 2003/0211603, and 2008/0171385, which are hereby incorporated by reference. It is appreciated that additional methods for the culture and maintenance of pluripotent stem cells, as would be known to one of skill, may be used with the present invention.

In certain embodiments, undefined conditions may be used; for example, pluripotent cells may be cultured on fibroblast feeder cells or a medium that has been exposed to fibroblast feeder cells in order to maintain the stem cells in an undifferentiated state.

Alternately, pluripotent cells may be cultured and maintained in an essentially undifferentiated state using defined, feeder-independent culture system, such as a TeSR medium (Ludwig et al., 2006a; Ludwig et al., 2006b) or Essential 8 medium (Chen et al., 2011). Feeder-independent culture systems and media may be used to culture and maintain pluripotent cells. These approaches allow derived human iPS cells as well as human embryonic stem cells to remain in an essentially undifferentiated state without the need for mouse fibroblast "feeder layers." As described herein, various modifications may be made to these methods in order to reduce costs as desired.

Various matrix components may be used in culturing and maintaining human pluripotent stem cells. For example, Matrigel™, collagen IV, fibronectin, laminin, PLO laminin, collagenI, collagenIV, fibrin clot, and vitronectin in combination may be used to coat a culturing surface as a means of providing a solid support for pluripotent cell growth, as described in Ludwig et al. (2006a; 2006b), which are incorporated by reference in their entirety. Particularly, Matrigel™ may be used to provide a substrate for cell culture and maintenance of human pluripotent stem cells. Matrigel™ is a gelatinous protein mixture secreted by mouse tumor cells and is commercially available from BD Biosciences (New Jersey, USA). This mixture resembles the complex extracellular environment found in many tissues and is used by cell biologists as a substrate for cell culture.

C. Cell Passaging

Certain aspects of the present invention can further involve a step of dissociating cells. Cell dissociation can be performed using any known procedures. These procedures include treatments with a chelating agent (such as EDTA), an enzyme (such as trypsin, collagenase), or the like, and operations such as mechanical dissociation (such as pipetting). The cell(s) can be treated with the ROCK inhibitor or myosin II inhibitor before and/or after dissociation. For example, the cell(s) may be treated only after dissociation.

In some further embodiments of cell culturing, once a culture container is full, the colony may be split into aggregated cells or even single cells by any method suitable for dissociation, which cells are then placed into new culture containers for passaging. Cell passaging is a technique that enables one to keep cells alive and growing under cultured conditions for extended periods of time. Cells usually would be passed when they are about 70%-100% confluent.

Single-cell dissociation of cells followed by single cell passaging may be used in the present methods with several advantages, like facilitating cell expansion, cell sorting, and defined seeding for differentiation and enabling automation of culture procedures and clonal expansion. For example, progeny cell clonally derivable from a single cell may be homogenous in genetic structure and/or synchronized in cell cycle, which may increase targeted differentiation. Exemplary methods for single cell passaging may be as described in U.S. Pat. Publication 2008/0171385, which is incorporated herein by reference.

In certain embodiments, cells may be dissociated into single individual cells, or a combination of single individual cells and small cell clusters comprising 2, 3, 4, 5, 6, 7, 8, 9, 10 cells or more. The dissociation may be achieved by mechanical force, or by a cell dissociation agent, such as sodium citrate, or an enzyme, for example, trypsin, trypsin-EDTA, TrypLE Select, or the like.

Based on the source of cells and the need for expansion, the dissociated cells may be transferred individually or in small clusters to new culture containers in a splitting ratio such as at least or about 1:2, 1:4, 1:5, 1:6, 1:8, 1:10, 1:20, 1:40, 1:50, 1:100, 1:150, 1:200, or any range derivable therein. Suspension cell line split ratios may be done on volume of culture cell suspension. The passage interval may be at least or about every 1, 2, 3, 4, 5, 6, 7, 8, 9, 10, 11, 12, 13, 14, 15, 16, 17, 18, 19, 20 days or any range derivable therein. For example, the achievable split ratios for the different enzymatic passaging protocols may be 1:2 every 3-7 days, 1:3 every 4-7 days, and 1:5 to 1:10 approximately every 7 days, 1:50 to 1:100 every 7 days. When high split ratios are used, the passage interval may be extended to at least 12-14 days or any time period without cell loss due to excessive spontaneous differentiation or cell death.

In certain aspects, single cell passaging may be in the presence of a small molecule effective for increasing cloning efficiency and cell survival, such as a ROCK inhibitor as described above. Such a ROCK inhibitor, e.g., Y-27632, HA-1077, H-1152, HA-100, or blebbistatin, may be used at an effective concentration, for example, at least or about 0.02, 0.05, 0.1, 0.2, 0.5, 1, 2, 3, 4, 5, 10, 15, 20, 25, 30, 35, 40, 45, 50 to about 100 µM, or any range derivable therein.

D. Normoxia and Hypoxia

Hypoxic culture can be accomplished with any of a variety of culture chambers known in the art, such as, for example, ProOxC (BioSpherix, Lacona, N.Y.); Hypoxic Glove Box (Coy Laboratory Products, Inc., Grass Lake, Mich.,); HypOxystation (HypOxygen, Frederick Md.); or Hypoxia Chamber (StemCell Technologies, Inc., Vancouver, BC).

Normoxic conditions generally include oxygen levels normative for culturing of cells. Except as otherwise provided herein, culture of cells under normoxic conditions can utilize methods, apparatuses and components known to persons of skill in the art. Such methods can be utilized directly or adapted for use as normoxic culture conditions.

In various aspects of the present teachings, a hypoxic atmosphere in which cells are grown or maintained can be replaced with a normoxic atmosphere. In some embodiments, cells can grow under hypoxic conditions and can differentiate under normoxic conditions. Duration of maintaining a culture under hypoxic conditions can be determined by routine experimentation by a person of skill in the art. Similarly, duration of maintaining a culture under normoxic conditions following hypoxic culture can be determined by routine experimentation by a person of skill in the art.

As used herein, hypoxic conditions are characterized by a lower oxygen concentration as compared to the oxygen concentration of ambient air (approximately 15%-20% oxygen). By way of reference, $O_2$ concentrations in the human body range from 0.5%-7% in the brain; 1%-5% in the eyes; 4%-12% in the liver, heart and kidneys, and 3%-5% in the uterus. In one aspect, hypoxic conditions are characterized by an oxygen concentration less than about 10%. In another aspect hypoxic conditions are characterized by an oxygen concentration of about 1% to 10%, 1% to 9%, 1% to 8%, 1% to 7%, 1% to 6%, 1% to 5%, 1% to 4%, 1% to 3%, or 1% to 2%. In a certain aspect, the system maintains about 1-3% oxygen within the culture vessel. Hypoxic conditions can be created and maintained by using a culture apparatus that allows one to control ambient gas concentrations, for example, an anaerobic chamber.

Incubation of cell cultures is typically performed in normal atmosphere with 15%-20% oxygen and 5% $CO_2$ for expansion and seeding, at which point low oxygen cultures are split to an airtight chamber that is flooded with 95% nitrogen/5% $CO_2$ so that a hypoxic environment is created within the culture medium.

The growth or culture media used in any of the culturing steps of the present invention, whether under normoxic or hypoxic conditions, may include serum, or be serum free. Additionally, the same media can be used for both hypoxic and aerobic cultivation.

Incubation conditions will be under appropriate conditions of pH, temperature, and gas (e.g., $O_2$, $CO_2$, etc.) to maintain hypoxic growth conditions.

VI. Expression of Markers

To determine the amount of a specific cell type in a cell culture or cell population, a method of distinguishing the specific cell type from the other cells in the culture or in the population is desirable. Accordingly, markers whose presence, absence, and/or relative expression levels are specific for certain cell types made according to the present invention are provided as are methods for detecting and determining the expression of such markers.

As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker.

As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein, or a small molecule.

The presence, absence, and/or level of expression of a marker may be determined by quantitative PCR (qPCR). For example, the amount of transcript produced by certain genetic markers, such as CXCR-4, CD117, SOX17, FOXA2, FOXA1, CD31, CD34, and HNF4A, is determined by quantitative qPCR. Additionally, immunohistochemistry or flow cytometry may be used to detect the proteins expressed by the above-mentioned genes. qPCR, flow cytometry, and immunohistochemistry may be used to identify and determine the amount or relative proportions of such markers.

VII. Use of Endoderm Progenitor and Beta Cells

The endoderm progenitor and beta cells provided by methods and compositions of certain aspects of the invention can be used in a variety of applications. These include but are not limited to transplantation or implantation of the beta cells in vivo; screening cytotoxic compounds, carcinogens, mutagens growth/regulatory factors, pharmaceutical compounds, etc., in vitro; elucidating the mechanism of diabetes; studying the mechanism by which drugs and/or growth factors operate; diagnosing and monitoring diabetes in a patient; gene therapy; and the production of biologically active products, to name but a few.

A. Test Compound Screening

Differentiation-derived endoderm progenitor or beta cells of this invention can be used to screen for factors (such as solvents, small molecule drugs, peptides, and polynucleotides) or environmental conditions (such as culture conditions or manipulation) that affect the characteristics of beta cells provided herein.

In some applications, stem cells (differentiated or undifferentiated) are used to screen factors that promote maturation of cells along the pancreatic islet beta cell lineage, or promote proliferation and maintenance of such cells in long-term culture. For example, candidate beta cell maturation factors or growth factors are tested by adding them to endoderm progenitor cells in different wells, and then determining any phenotypic change that results, according to desirable criteria for further culture and use of the cells.

Particular screening applications of this invention relate to the testing of pharmaceutical compounds in drug research. The reader is referred generally to the standard textbook *In vitro Methods in Pharmaceutical Research*, Academic Press, 1997, and U.S. Pat. No. 5,030,015). In certain aspects of this invention, cells differentiated to the endoderm progenitor or beta cell lineage play the role of test cells for standard drug screening and toxicity assays, as have been previously performed on endodermal cell lines or primary endodermal cells in short-term culture. Assessment of the activity of candidate pharmaceutical compounds generally involves combining the endoderm progenitor or beta cells provided in certain aspects of this invention with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on endoderm progenitor cells or beta cells, or because a compound designed to have effects elsewhere may have unintended side effects on beta cells. Two or more drugs can be tested in combination (by combining with the cells either simultaneously or sequentially), to detect possible drug-drug interaction effects. In some applications, compounds are screened for toxicity to beta cells. See, e.g., Kuzuya et al., 2001.

B. Beta Cell Therapy and Transplantation

This invention also provides for the use of beta cells provided herein to restore a degree of pancreatic function to a subject needing such therapy, perhaps due to diabetes. For example, pancreatic islet beta cells and endodermal progenitor cells derived by methods disclosed here may be used to treat diabetes (such as, e.g., by engineering of grafts).

To determine the suitability of beta cells provided herein for therapeutic applications, the cells can first be tested in a suitable animal model. At one level, cells are assessed for their ability to survive and maintain their phenotype in vivo. Beta cells provided herein are administered to immunodeficient animals (such as SCID mice, or animals rendered immunodeficient chemically or by irradiation) at a site amenable for further observation, such as under the kidney capsule, into the spleen, or into a liver lobule. Tissues are harvested after a period of a few days to several weeks or more, and assessed as to whether starting cell types, such as pluripotent stem cells are still present. This can be performed by providing the administered cells with a detectable label (such as green fluorescent protein, or β-galactosidase); or by measuring a constitutive marker specific for the administered cells. Where beta cells provided herein are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided in elsewhere in this disclosure.

Beta cells and endoderm progenitor cells provided by methods of the invention may be tested in various animal models for their ability to treat diabetes. Various such animal models that may find use in certain aspects of the present invention are discussed in, for example, Srinivasan and Ramarao (2007) and King (2012). A preferred animal model is immunocompromised mice treated with streptozotocin to induce experimental diabetes. Differentiated beta cells may be implanted within the kidney capsule, and if the cells are functional then the diabetes will be reversed. This assay is commonly used to test the function of cadaveric islets.

Beta cells and endoderm progenitor cells provided in certain aspects of this invention that demonstrate desirable functional characteristics according to their profile of enzymes, or efficacy in animal models, may also be suitable for direct administration to human subjects in need thereof. Beta cells may also be delivered directly to the pancreas.

The beta cells or endoderm progenitors provided in certain aspects of this invention can be used for therapy of any subject in need thereof. A preferred human condition that may be appropriate for such therapy is diabetes. For human therapy, the dose is generally between about $10^9$ and $10^{12}$ cells, and typically between about $5\times10^9$ and $5\times10^{10}$ cells, making adjustments for the body weight of the subject, nature and severity of the affliction, and the replicative capacity of the administered cells. The ultimate responsibility for determining the mode of treatment and the appropriate dose lies with the managing clinician.

Certain aspects of the invention include beta cells or endoderm progenitor cells provided herein that form part of a bioengineered tissue graft. Such a tissue graft may be a pancreatic tissue graft.

C. Distribution for Commercial, Therapeutic, and Research Purposes

For purposes of manufacture, distribution, and use, the beta cell lineage cells, including endoderm progenitors, of this invention are typically supplied in the form of a cell culture or suspension in an isotonic excipient or culture medium, optionally frozen to facilitate transportation or storage.

This invention also includes different reagent systems, comprising a set or combination of cells that exist at any time during manufacture, distribution, or use. The cell sets comprise any combination of two or more cell populations described in this disclosure, exemplified but not limited to differentiation-derived cells (beta cell lineage cells, their precursors and subtypes), in combination with undifferentiated stem cells or other differentiated cell types. The cell populations in the set sometimes share the same genome or a genetically modified form thereof. Each cell type in the set may be packaged together, or in separate containers in the same facility, or at different locations, at the same or different times, under control of the same entity or different entities sharing a business relationship.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Generation of Definitive Endoderm (DE) Cells

Human iPSCs were maintained under feeder-free conditions in the presence of TeSR or Essential 8 media. For monolayer endoderm progenitor differentiation of iPSCs, PSCs were plated onto Matrigel-coated dishes at 80% confluency. Undifferentiated iPSCs were cultured in the presence of Activin A (100 ng/ml) or Nodal (100 ng/ml) in RPMI medium supplemented with 10% SFD, 1× glutamine, MTG ($4.5 \times 10^{-4}$ M) under serum-free conditions for day zero, followed by two days in the RPMI/10% SFD medium further supplemented with ascorbic acid (50 µg/mL), BMP4 (0.5 ng/ml), bFGF (10 ng/ml), and VEGF (10 ng/ml) under serum-free conditions. This was followed by four days in SFD medium supplemented with MTG ($4.5 \times 10^{-4}$ M), ascorbic acid (50 µg/ml), BMP4 (0.5 ng/ml), bFGF (10 ng/ml), Activin A (100 ng/ml) and VEGF (10 ng/ml) with a media change after two days. SFD medium was made as per Cheng et al. (2012b). For sampling, a portion of the cells were harvested, individualized, and stained for the surface expression of CXCR4 and CD117 and intracellular expression of FoxA1, Sox17, and FoxA2 using specific antibodies and visualized using flow cytometry (FIGS. 1 and 2A-F). This cellular population, as defined by the coexpression of CXCR4, CD117, FoxA2, and FoxA1, was generated between days 5 and 7. Further optimization and additional embodiments of DE generation are provided below.

Example 2—Effects of Seeding Density on the Generation of DE

Figure 16:
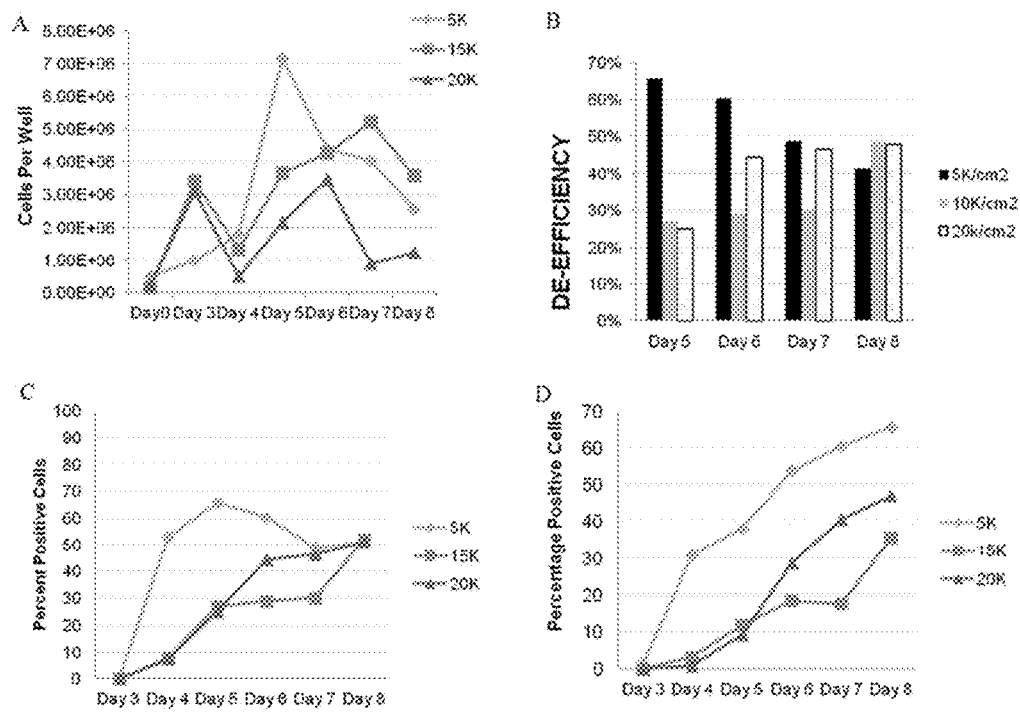
FIGS. 16A-D. Effect of seeding density on the generation of definitive endoderm (DE) from undifferentiated iPSC. DE generation was performed in the absence of CHIR and in the presence of 2.5 ng/ml BMP4.

Undifferentiated iPSCs maintained using Essential 8 on Matrigel were plated at different seeding densities/$cm^2$ (e.g., 5000, 15,000, and 20,000) on Matrigel. Four days-post-plating, the cells seeded at 15,000 and 20,000 cells/$cm^2$ were placed in 90% RPMI/10% SFD media containing 100 ng/mL Activin A (T0) for 24 h. On the next day, the cultures were placed in media containing 100 ng/mL Activin A, 2.5 ng/mL BMP4, 10 ng/mL VEGF, and 10 ng/mL zebrafish FGF2 for 48 h (T1/T2). Finally, the cultures were placed in SFD media supplemented with 100 ng/mL Activin A, 2.5 ng/mL BMP4, 10 ng/mL VEGF, and 10 ng/mL zebrafish FGF2 for the next 4-5 days (T3-T6). At this step, the cells can optionally be incubated for up to 12 days. The cells were harvested from day 3 to day 6 using TrypLE. The total viable cell number post digestion was determined at each time point (FIG. 16A). The percentage of CXCR4, CD117 co-expressing cells was determined by surface staining (FIG. 16D), while the percentage of FoxA2 and FoxA1 (FIG. 16C) expression was quantified by intracellular flow cytometry. The efficiency of the process was determined as a ratio of absolute number of DE expressing cells/Total cell number at each time point.

Example 3—Supplementation with CHIR is not Essential for the Generation of DE

Undifferentiated iPSCs maintained using Essential 8 on Matrigel were plated at a seeding density of 13,000 cells/$cm^2$ on Matrigel. Four days-post-plating, the cells were placed in 90% RPMI/10% SFD media containing 100 ng/mL Activin A for one day followed by incubation with 90% RPMI/10% SFD supplemented with 100 ng/mL Activin A, 2.5 ng/mL BMP4, 10 ng/mL VEGF, and 10 ng/mL zebrafish FGF2 for the next two days. From day 4-12, the cells were placed in SFD media supplemented with 100 ng/mL Activin A, 2.5 ng/mL BMP4, 10 ng/mL VEGF, and 10 ng/mL zebrafish FGF2. Supplementation with 2 µM CHIR was included in one set at day 1 of differentiation while it was omitted in another set. The cells were harvested on day 7 using TrypLE. The total viable cell number post digestion was determined at each time point. The percentage of CXCR4, CD117 co-expressing cells was determined by cell surface staining by flow cytometry (Table 1). The absolute number of CXCR4/CD117 double-positive cells was calculated. The ratio of input iPSC to output DE was also quantified (Table 1). Adding CHIR on day zero of endoderm induction did not result in increased efficiency of DE formation.

TABLE 1

Supplementation with CHIR is not essential for DE formation.

| Cell line | CHIR | Format | CXCR4/CD117 | Input iPSCs ×10⁶ | Output DE Day 7 ×10⁶ | Efficiency iPSC:DE |
|---|---|---|---|---|---|---|
| 2.038 | − | T150 | 40% | 5.85 | 259 | 1:18 |
| 2.038 | + | T150 | 54% | 5.85 | 186 | 1:17 |
| 2.038 (1131) | − | 6 well | 53% | 1.95 | 84 | 1:23 |
| 2.038 (1131) | + | 6 well | 45% | 1.95 | 84 | 1:19 |

Example 4—Effects of Hypoxia on DE Induction

Oxygen concentration in the stem cell niche (usually 2%-9% $O_2$) plays a vital role in maintaining homeostasis, facilitates embryonic development, regulates multiple signaling cascades, and maintains stem cell pluripotency to induce differentiation (Langner et al., 2010). Undifferentiated iPSCs (2.038 AT4EGN) were maintained using Essential 8 on Matrigel under hypoxic conditions (5% $O_2$) in the presence of neomycin (100 µg/mL) and puromycin (600 ng/mL) for at least five passages. The cells were propagated using 0.5 mM EDTA and Essential 8 media. The seeding density of cells varied from 15,000-30,000 cells/$cm^2$ on Matrigel.

Figure 17:
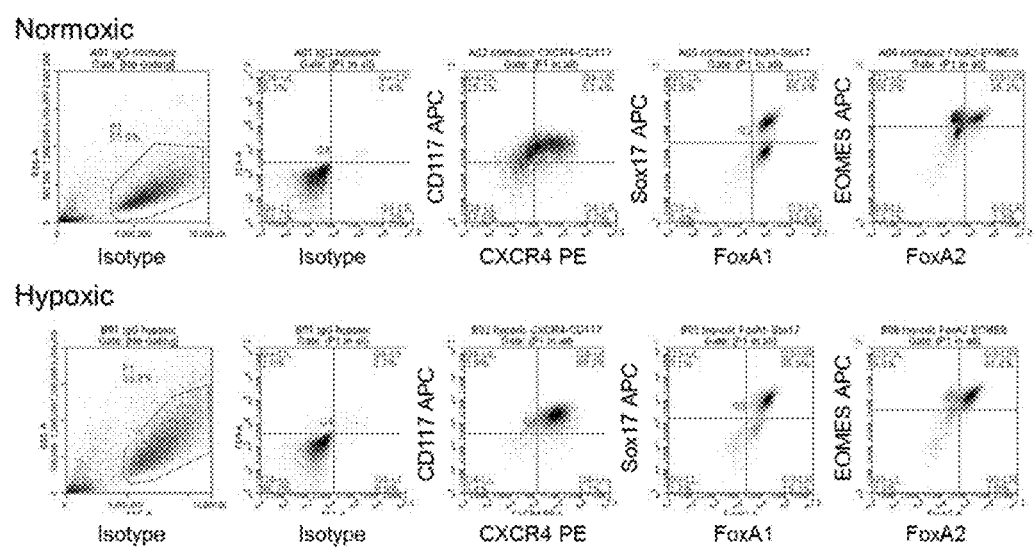
FIG. 17. Hypoxic conditions improve DE generation. The percentage of CXCR4-CD117 co-expressing cells was determined by cell surface staining by flow cytometry. The percentage of FoxA1-FoxA2-Sox17 was quantified using intracellular flow cytometry.

After acclimatizing iPSCs to hypoxic conditions, optimally for at least five passages, the cells were plated at a density of 15,000 cells/$cm^2$ on Matrigel. Four days-post-plating, the cells were placed in SFD media containing 100 ng/mL Activin A, 2.5 ng/mL BMP4, 10 ng/mL VEGF, and 10 ng/mL zebrafish FGF2 for the next eight days. A parallel differentiation was set up using iPSCs maintained on Matrigel using Essential 8 under normoxic conditions. Both sets were harvested on day 8 using TrypLE. The total viable cell number post digestion was determined and the percentage of CXCR4, CD117 co-expressing cells was determined by cell surface staining by flow cytometry. The percentage of FoxA1/FoxA2/Sox17 was quantified using intracellular flow cytometry (FIG. 17).

iPSCs maintained under hypoxic conditions generate DE with higher purity when compared to iPSCs maintained under normoxic conditions. Normoxic cells demonstrated about 50% DE-positive staining while hypoxic cells expressed 80%-90% DE-positive staining Hypoxic conditions offer a process improvement for generating DE, as well as increase the duration of cycling of EPCs, as is discussed below. Efficiency of the process was around 1:20 (iPSC: DE).

Example 5—Generation of Endoderm Progenitor (EP) Cells

DE cells were harvested using TrypLE, and the individualized cells were washed with quench media. The total viable cell count of the cultures was determined. The cells were washed again and the resulting cell pellet was placed on ice. Cold, prechilled neat Matrigel solution was added to the cell pellet at a concentration between 0.3 and 0.6 mg/ml. Prechilled serum-free SFD media containing glutamine (1×), MTG ($4.5 \times 10^{-4}$ M), ascorbic acid (50 µg/ml), 100 ng/ml BMP4, 20 ng/ml EGF, 20 ng/ml FGF2, and 20 ng/ml VEGF and containing a Rock inhibitor, either 1 µM H1152 or 10 µM Y-27632, was added to the mixture of cells and Matrigel on ice using prechilled pipette tips and mixed gently to prevent the formation of bubbles. The final cell density was between 0.25 and 1 million cells/ml. The resulting Matrigel-cell suspension was transferred to a 125 spinner flask. The spinner was placed at regular oxygen (20%) and 5% $CO_2$ and the spinner speed varied between 40 and 70 RPM. The aggregates formed within 12-18 hours. On the next day, the cellular aggregates were allowed to settle and the supernatant media from the spinner was discarded. The cellular aggregates were placed in serum-free SFD media containing glutamine (1×), MTG ($4.5 \times 10^{-4}$ M), ascorbic acid (50 µg/ml), 100 ng/ml BMP4, and 20 ng/ml each of VEGF, EGF and FGF2. The spinner was half fed every day or a complete media change was performed every 48 hrs. In other related experiments, the suspension aggregates were dissociated and reaggregated about every 5 days. The EP aggregates were sampled at various time points throughout the process.

Figure 2G:
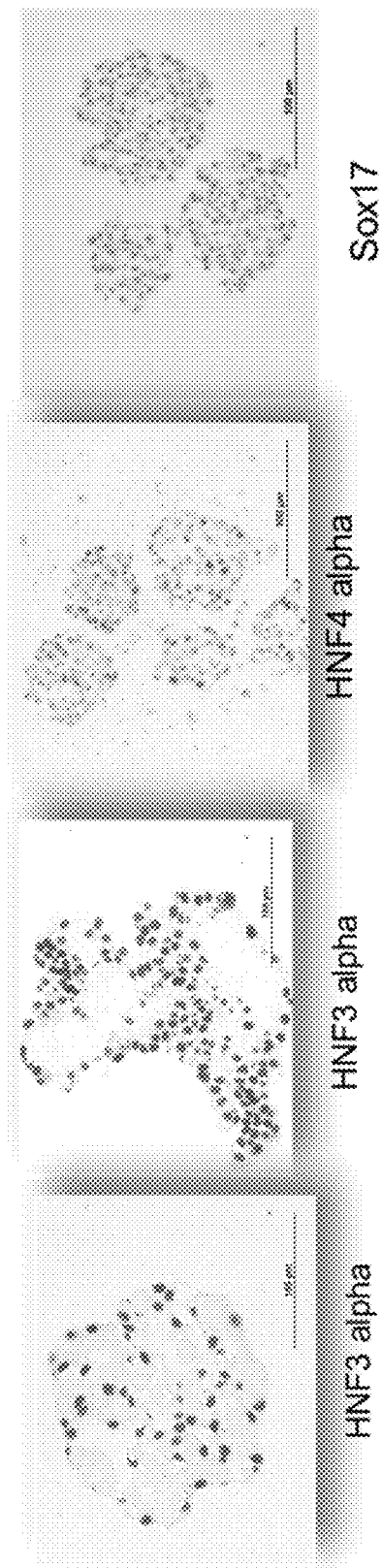
Figure 3:
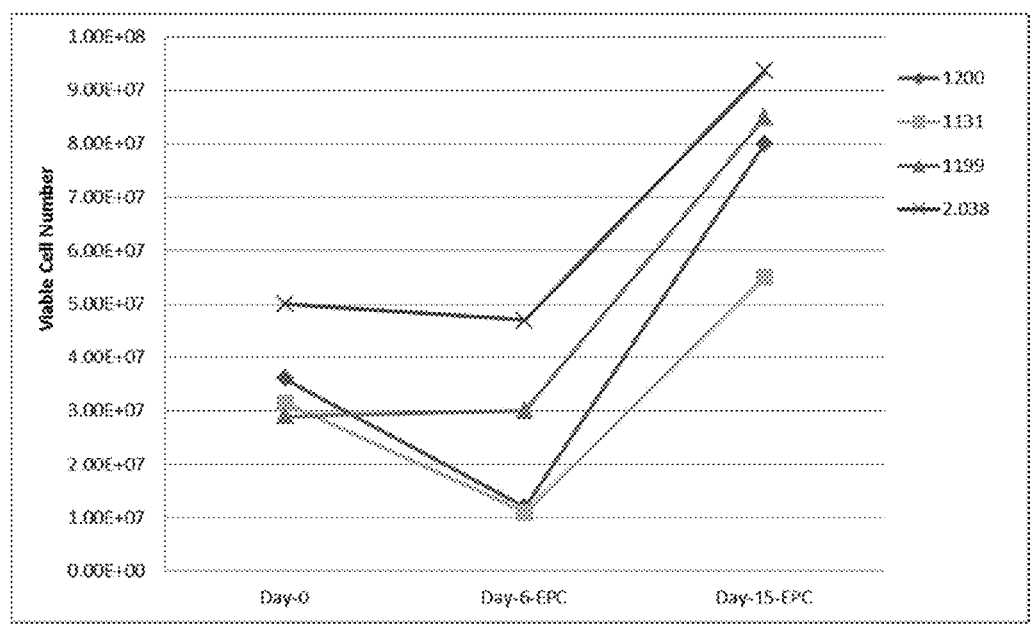
FIG. 3. Cell viability and survival of iPSC-derived EP-cultures in suspension over 15 days. EPs were derived from four different iPSCs lines. The graph represents the number of viable cells present as quantified by flow cytometry. Experiment was performed under normoxic conditions.
Figure 4:
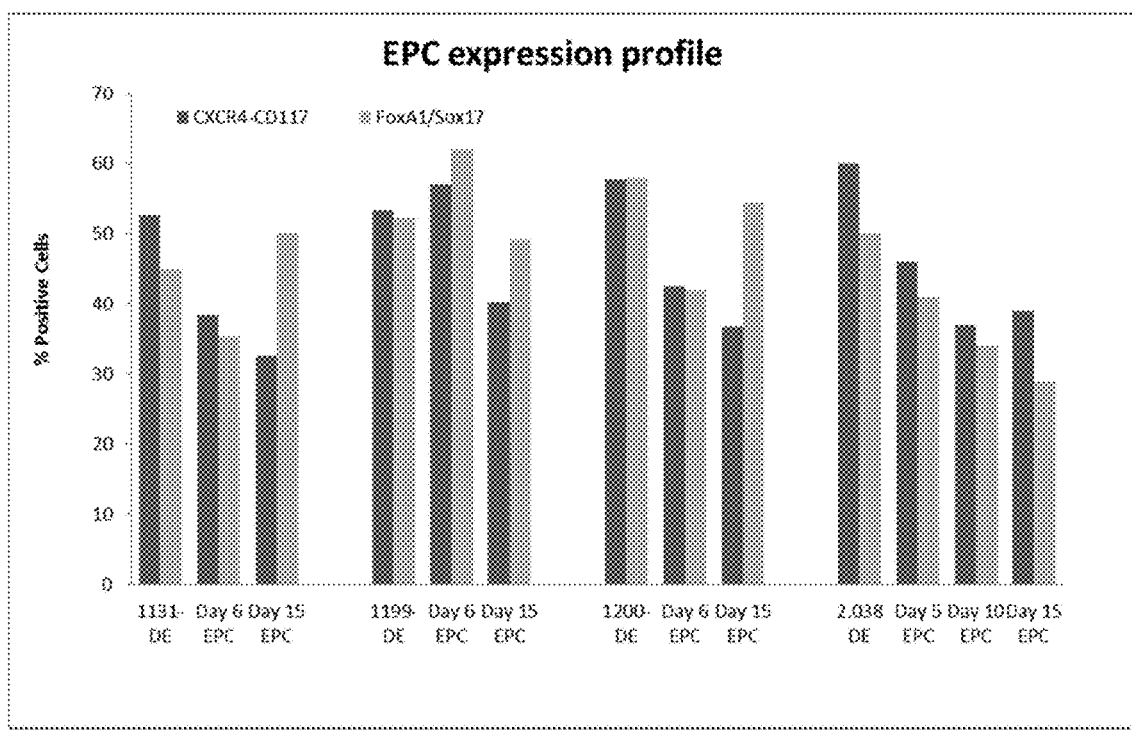
FIG. 4. Cell viability and survival of iPSC-derived EP-cultures in suspension over 15 days. EPs were derived from four different iPSCs lines. Experiment was performed under normoxic conditions. The plot represents the levels of CXCR-4/CD117(c-kit)/FoxA1/Sox17 expression as quantified by flow cytometry.

For sampling, a desired volume of aggregates was removed from the spinner and the aggregates were spun down by centrifugation (1200 rpm, 5 minute). The aggregates were individualized by Trypsin digestion, quenched, washed, and the cells resuspended in appropriate media for cell counts and FACs staining FIG. 2G provides representative images of intact 15 day EPC aggregates in suspension cultures, embedded in histogel, and stained for the presence of HNF3 alpha, HNF4 alpha, and Sox17 expression. The presence of viable cells was quantified as depicted in FIG. 3. The levels of CXCR4/CD117/FoxA1/Sox17 expression were quantified by flow cyotmetry (FIG. 4).

Example 6—Matrigel Preserves DE while MEFs are not Essential for EPC Cycling

Definitive endoderm cells generated from undifferntiatied iPSCs maintained using Matrigel and Essential 8 media were harvested using TrypLE. Post harvest, the individualized cells were washed with quench media. The total viable cell count of the cultures was determined. The cells were washed again and the resulting cell pellet was placed on ice. Cold, prechilled neat Matrigel solution was added to the cell pellet at a concentration of 0.3 mg/ml. Prechilled serum free EPC cycling media (IMDM: Ham's F12 (3:1), 0.5% B27, 0.5% N2, 0.1% BSA, 1% Glutamax, 0.45 µM MTG, 50 µg/mL ascorbic acid, 50 ng/mL BMP4, 10 ng/mL VEGF, 10 ng/mL EGF, 50 ng/mL FGF (either zebrafish FGF2 or heat stable FGF1), 2.5 ng/mL Activin, and 0.1 ng/mL TGFβ) supplemented with a Rock inhibitor, either 1 µM H1152 or 10 µM Y-27632, was added to the mixture of cells and Matrigel on ice with a final density between 0.25-0.5 million cells/mL. The resulting cell suspension was transferred to a 125 spinner flask or placed in an Ultra low attachment vessel under static conditions. The cultures were spun down and placed in fresh EPC cycling media devoid of the Rock inhibitor after 12 hours.

EPC aggregates were spun down and fed fresh EPC cycling media every other day. The cultures were reaggregated on day 4, day 8, and day 12. The aggregates were individualized using TrypLE for 5-10 minutes, quenched, and washed. The cultures were reaggregated in the presence of fresh Matrigel and Rock inhibitor. The media was changed after 12-18 hours at which point the cultures were placed in EPC cycling media devoid of Rock inhibitor.

EPC cultures were maintained for 15 days with or without 0.3 mg/mL Matrigel and with or without 1 MEF per 100 EPCs. At the end of 15 days, the EPC cultures were harvested using TrypLE or 0.5% Trypsin or a combination of dispase (2 mg/ml) and Trypsin. The individualized cell suspensions were quenched and washed, and the total viable cell number post-digestion was determined. The percentage of DE markers, CXCR4, CD117, FoxA2, and FoxA1, was quantified by flow cytometry. The efficiency of the process was determined as a ratio of absolute number of viable DE cells/Total viable cell number obtained at the end of the experiment.

Figure 18A:
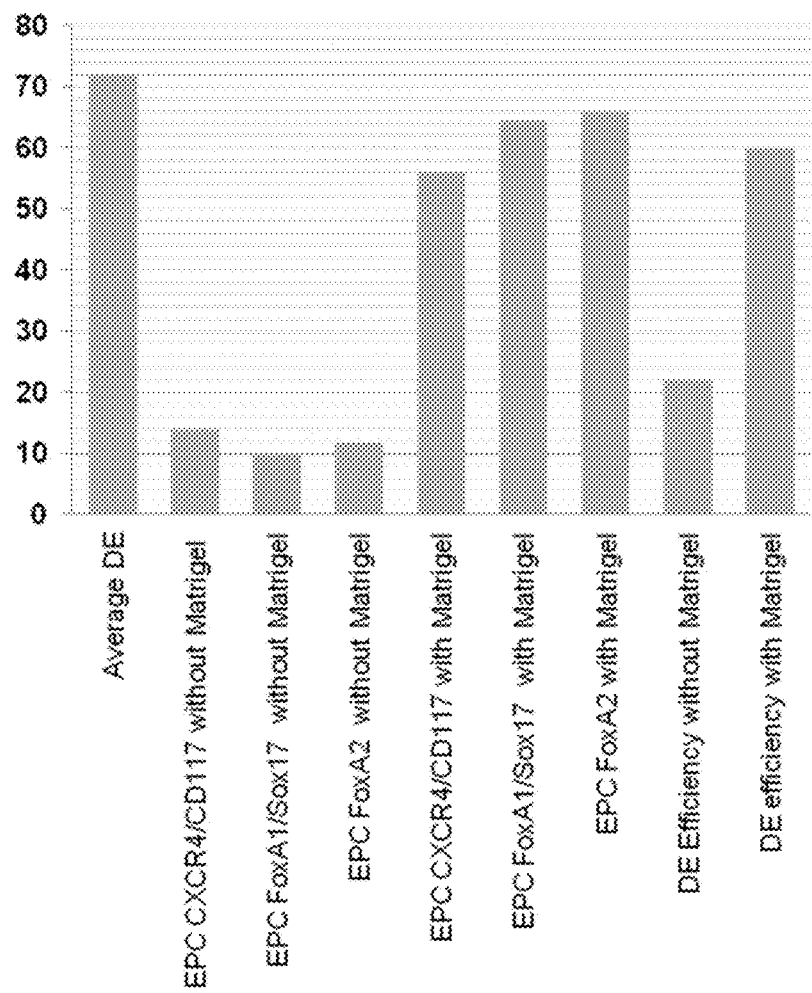

The presence of Matrigel preserved the phenotypic expression of DE expressing cells (FIG. 18A). The purity of EPC cultures declined in the absence of Matrigel (FIG. 18A). The efficiency of DE generation was also enhanced in the presence of Matrigel. Presence of MEFs was not essential during EPC cycling. 3D cultures retained EPC purity (FIGS. 18C and E) and yield (FIGS. 18B and D) in the absence of MEFs.

Example 7—EPC Cycling Under Defined Feeder-Free Hypoxic Conditions

Figure 19A:
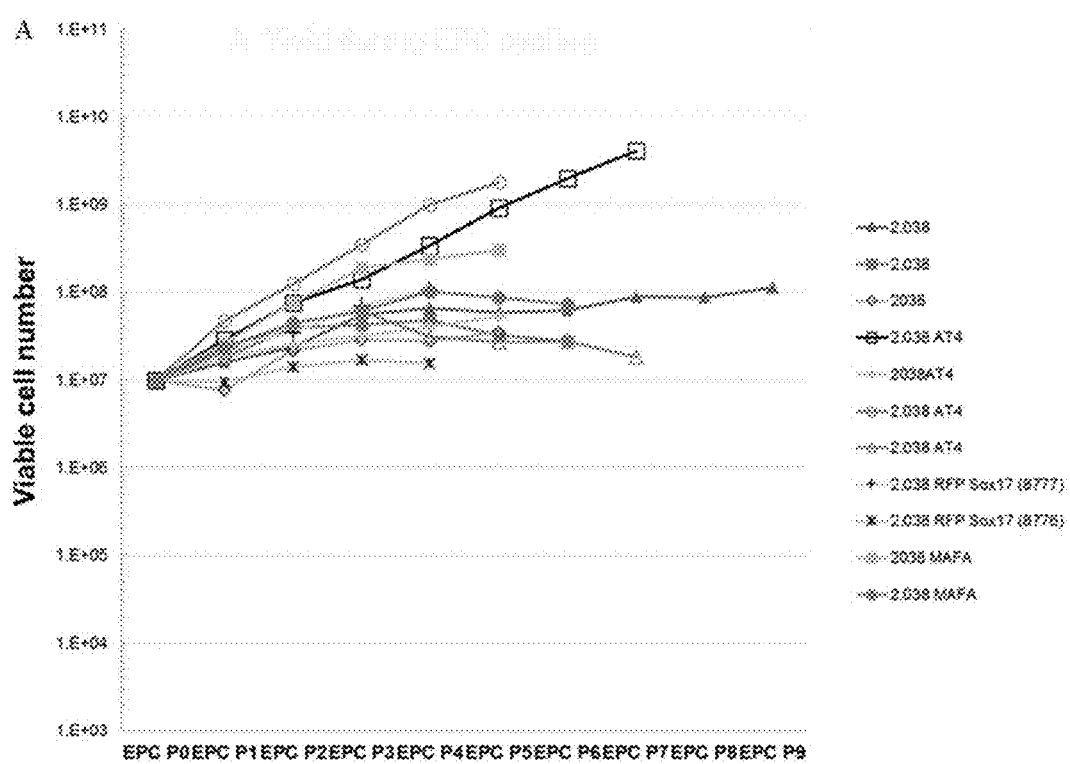
FIGS. 19A-B. EPC cycling of various iPSC clones under defined feeder free hypoxic conditions.
Figure 19B:
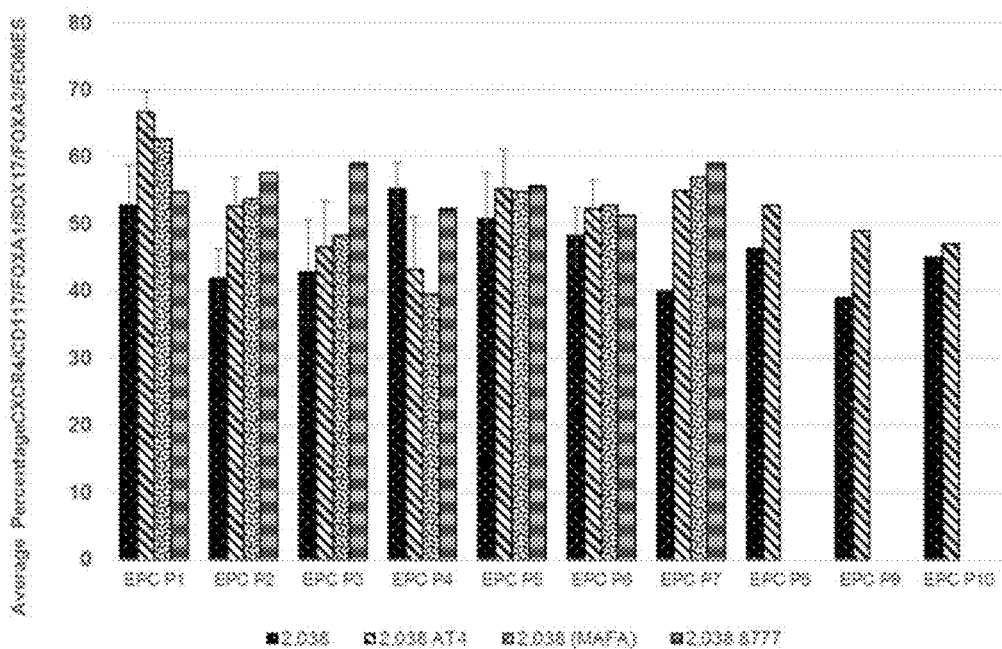

Definitive endoderm cells generated from various undifferentiated iPSCS maintained using Matrigel and Essential 8 media were harvested using TrypLE for 5-10 minutes. Individualized DEs were quenched and washed. The total viable cell count of the cultures was determined. The cells were washed again and the resulting cell pellet was placed on ice. Cold, prechilled neat Matrigel solution was added to the cell pellet at a concentration of 0.3 mg/ml. Pre chilled T3/T6 media (SFD media supplemented with 100 ng/mL Activin A, 2.5 ng/mL BMP4, 10 ng/mL VEGF, and 10 ng/mL zebrafish FGF2) supplemented with a Rock inhibitor (1 µM H1152) was added to the mixture of cells and Matrigel on ice with a final density at between 0.25-0.5 million cells/mL. The resulting cell suspension was transferred to a 125 spinner flask. The spinner speed was set to 70 rpm under hypoxic conditions. The cultures were spun down and placed in fresh media comprising 50% T3/T6 media and 50% serum-free EPC cycling media devoid of the Rock inhibitor after 12-18 hours. EPC aggregates were spun down and fed fresh EPC cycling media every other day thereafter with serum-free EPC cycling media. The cultures were reaggregated on day 4, day 8, and day 12 following TrypLE digestion as described above with 0.3 mg/ml Matrigel. All cell lines, expect 2.038 AT4, were reaggregated in the presence of a Rock inhibitor (H1152). The total viable cell count was estimated at every passage of EPCs. The spinner cultures remained under hypoxic conditions. The results depict the proliferation of EPCs during the feeder-free EPC cycling phase (FIG. 19A). 2.038AT4 (maintained in the presence of 100 µg/mL neomycin and 600 ng/mL puromycin) was the most proliferative compared to parental iPSCs. This cell line comprises Erg and GFI1 expression cassettes, whose expression is controlled by doxycycline induction. 2.038MAFA cells (maintained in the presence of G418 except during EPC cycling) comprise a MAFA expression cassette, whose expression is controlled by doxycycline induction. At each time point during EPC cycling, the purity of EPC cultures were determined by flow cytometry. The average expression of CXCR4/CD117/FoxA1/FoxA2/Sox17 was quantified. The purity of EPCs from various experimental runs of the same iPSC clone were averaged and the standard error was calculated (FIG. 19B). The results reveal average purity of about 50% for various iPSC clones cycled under feeder-free hypoxic conditions.

Example 8—qPCR Analysis of EPC Cultures Under Defined Feeder-Free Hypoxic Conditions The expression of genes associated with definitive endoderm and EPC aggregate cycling was quantified by real time RT-PCR (FIG. 20). EPCs were harvested every 4-5 days using 0.5% Trypsin-EDTA for 10-20 minutes at 37° C. Cells were vigorously pipetted to create a single-cell suspension. RNA was treated with RNase-free DNase and isolated using the Rneasy Plus Mini Kit from Qiagen (Catalog #74136) according to manufacturer's directions. RNA quantification was performed using the Nanodrop 2000.

RNA was reverse transcribed with the ImProm-II RT System from Promega (Catalog # A3800) according to manufacturer's directions. rt-qPCR was performed using TaqMan Gene Expression Master Mix (Catalog #4369016) and TaqMan probes (Catalog #4331182; CXCR4: Hs00237052_m1; Ckit: Hs00174029_m1; Sox17: Hs00751752_s1; FoxA1: Hs00270129_m1; FoxA2: Hs00232764_m1; GAPDH: Hs99999905_m1) with technical triplicates and run on the Roche LightCycler for 40 cycles. Fold induction was calculated by DeltaCp with normalization to GAPDH. No gene expression was seen in undifferentiated iPSC of the same genetic background (negative control). Positive controls, W2 P16 and 2.038 P2, demonstrated similar profiles to unknowns.

Figure 21:
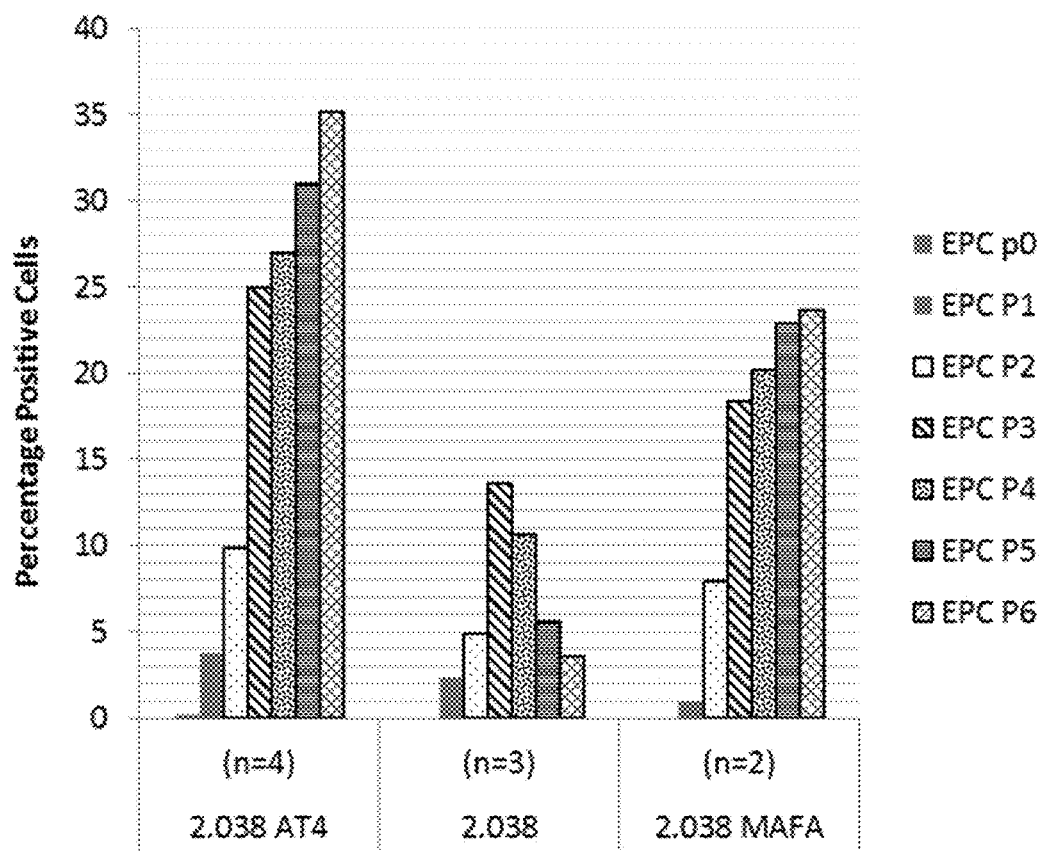
FIG. 21. CD34 is a late marker of EPC. The expression of CD34 was quantified using cell surface staining by flow cytometry.

CD34 was found to be a marker of late EPC cultures. 3D EPC cultures generated from 2.038AT4, 2.038 MAFA, and 2.038 parental cells were harvested at various passages during EPC cycling and stained for the presence of CD34. The EPC aggregates were individualized using Trypsin, quenched, washed, and stained for the presence of CD34 along with CXCR4 and CD117. The percentage of CD34 positive cells at different stages of EPC cycling was quantified using flow cytometry. The extent of CD34 expression varied for different iPSC clones. EPCs derived from 2.038 express 2%-15% CD34, EPCs derived from 2.038 (MAFA) express between 2%-25% CD34 positive cells while 2.038AT4 express between 4%-35% CD34 (FIG. 21). Emerging CD34 cells are CD117/CXCR4 positive.

Example 9—Purification of End-Stage EPC Cultures

Figure 22:
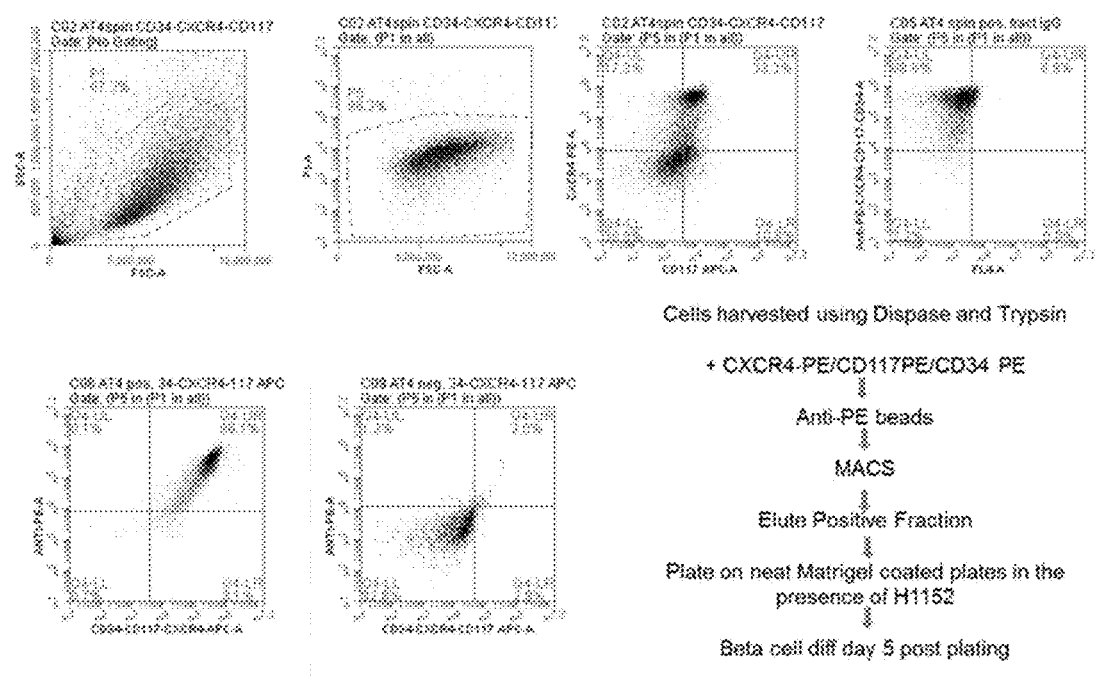
FIG. 22. Purification of end-stage EPC cultures. Individualized cells are incubated with phycoerythrin (PE)-conjugated antibodies to CD34, CD117, and CXCR4 prior to separation by MACS, which yields a positive fraction with about 88% purity.

End stage EPC cultures were harvested and individualized using 0.5% Trypsin solution. The cell suspension was quenched, washed, and incubated with CXCR-4/CD117/CD34 conjugated to PE for 20 minutes at 4° C. The cells were washed and incubated with magnetic anti-PE antibody for 20 minutes at 4° C. The cells were washed and purified using a MACS column according to the manufacturer's instructions. The purity and the cell number of the positive fraction were determined (FIG. 22). The cells were placed on neat Matrigel-coated plates in EPC modified media supplemented with a Rock inhibitor. After 12-18 hrs post-plating, the cells were placed in fresh EPC modified media without a Rock inhibitor. Five days-post plating, beta cell differentiation was initiated.

Example 10—Pancreatic Differentiation of EPC Aggregates

EPCs generated in suspension culture were placed in differentiation medium (FIG. 8) for the generation of pancreatic cell types. For pancreatic differentiation of EP cells, a protocol described by Nostro et al. (2011) further modified by Cheng et al. (2012a) was utilized. The entire process was continued as a 3D culture.

EPC cultures were expanded for 15 days and cultured in SFD media containing Wnt3A (3 ng/ml), FGF-10 (50 ng/ml) and Dorsomorphin (0.75 µM) for three days to generate foregut/midgut endoderm cells. The cells were cultured in high glucose DMEM media containing GlutaMAX (1%), B27 without retinoic acid (1%), ascorbic acid (50 µg/ml), Pen/Strep (1%), KAAD-Cyclopamine (0.25 µM), trans-Retinoic acid (2 µM), Noggin (50 ng/ml), and FGF-10 (50 ng/ml) for three days to generate pancreatic endoderm cells. Following this step the cells were cultured in high glucose DMEM media containing GlutaMAX (1%), B27 without retinoic acid (1%), ascorbic acid (50 µg/ml), Pen/Strep (1%), SB431542 (6 µM), and Noggin (50 ng/ml) for three days. Next, the cells were cultured in the previous high glucose DMEM medium supplemented with a γSecretase inhibitor (DAPT at 2 µM) for one to two days. From this stage the cells were cultured in SFD media containing glucose (40 mM), nicotinamide (10 mM), SB431542 (6 µM), and Noggin (50 ng/ml) for one to two days. Finally, the cells were cultured in SFD medium containing SB431542 (5.4 µM), Noggin (50 ng/ml), insulin (800 µM, 0.47 µl/ml), and nicotinamide (10 mM) that was alternated every day between such medium with additional glucose added (40 mM) and no additional glucose added for the next 10 days.

Figure 5:
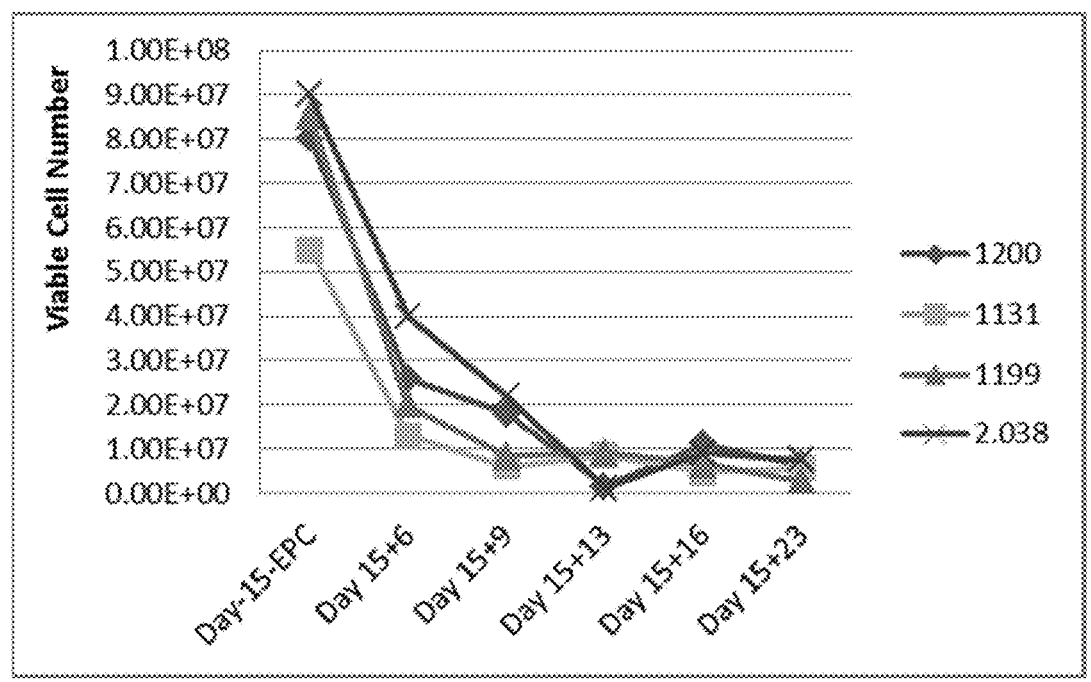
FIG. 5. Cell viability and survival of 15 day EPC-cultures placed in the pancreatic differentiation protocol. Experiment was performed under normoxic conditions. To characterize the emerging populations in EPC aggregates, aggregates were individualized and viable cell counts determined at various days in the process of differentiation.
Figure 6:
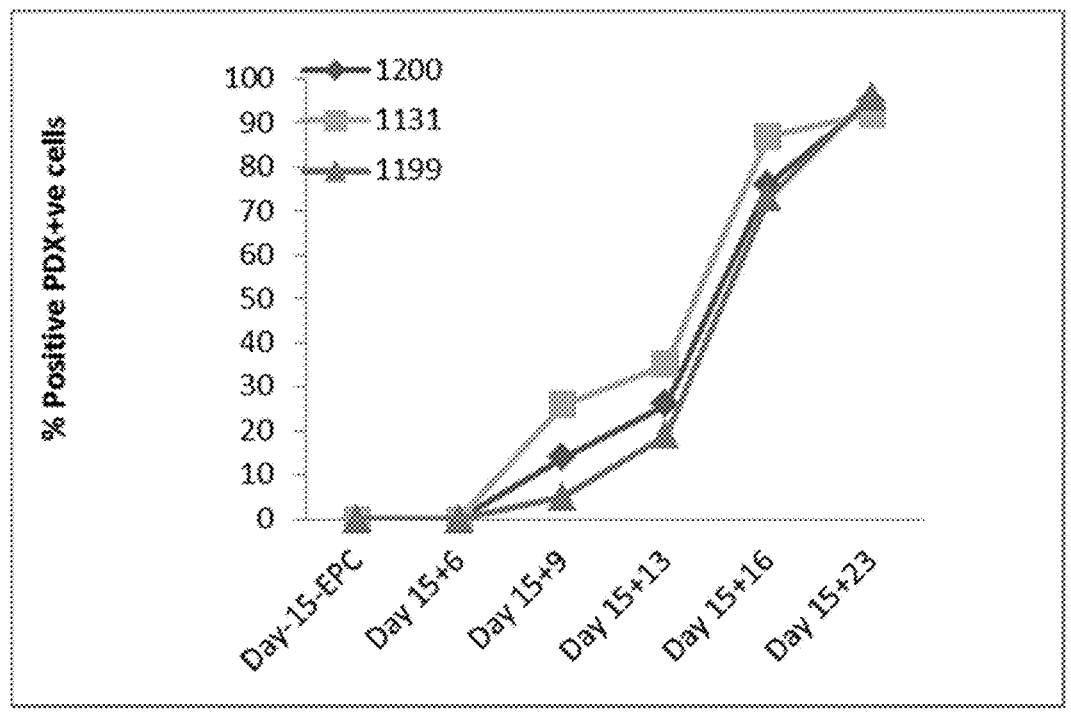
FIG. 6. Emergence of PDX-1 positive cells from 15 day EPC-cultures placed in pancreatic differentiation media. Experiment was performed under normoxic conditions. To characterize the EPC aggregates, individualized cells were stained for the presence of PDX-1 by performing intracellular staining and assessing the percentage of positive cells by flow cytometry.
Figure 7:
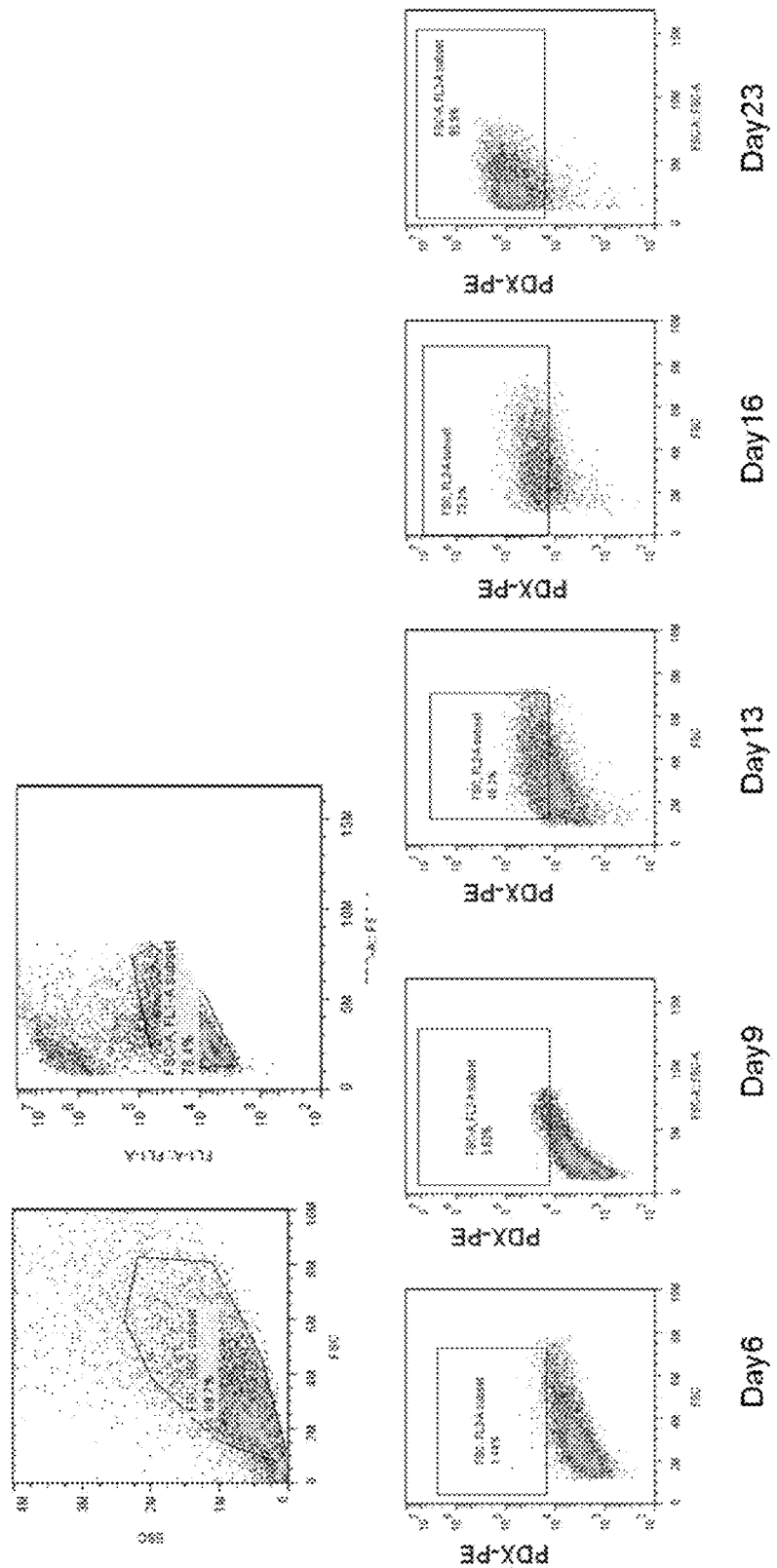
FIG. 7. Representative staining profile of PDX-1 positive cells on different days of the pancreatic differentiation process. Experiment was performed under normoxic conditions.
Figure 9:
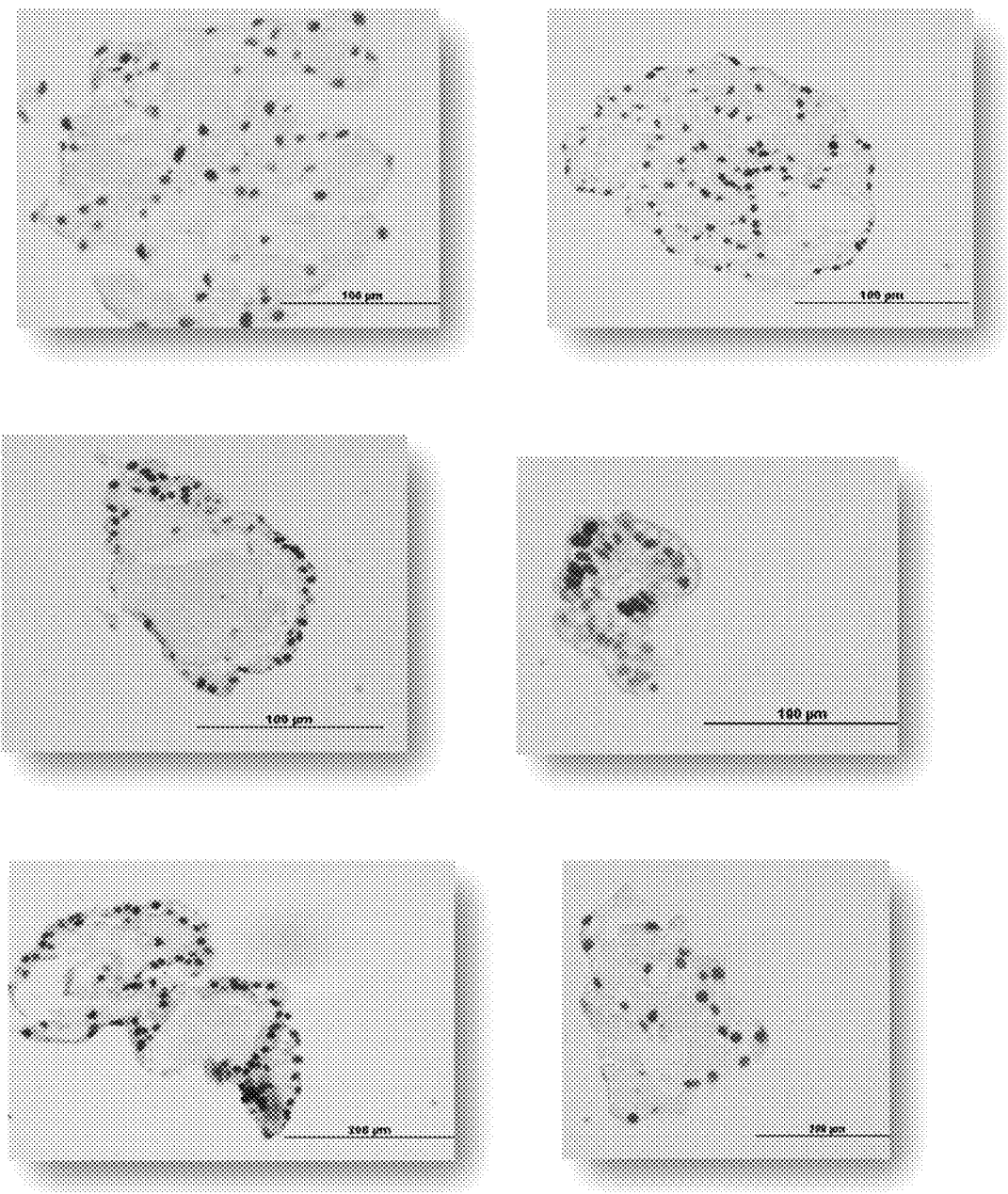
FIG. 9. Immunohistochemical staining for PDX-1 expression in 15-day-old EPC-aggregates on day 15 of the pancreatic differentiation process. Experiment was performed under normoxic conditions. Representative images of intact 15 day EPC-aggregates in suspension cultures placed in pancreatic differentiation media for 15 days, embedded in histogel, and stained for the presence of PDX-1 by immunohistochemical staining Photographs were taken at 10× and 20× magnification.

For sampling, a desired volume of aggregates were removed from the spinner and the aggregates were spun down by centrifugation (1200 rpm, 5 minutes). The aggregates were individualized by Trypsin digestion, quenched, washed, and the viable cell count at various days in the process was determined (FIG. 5). The individualized cells were stained for the presence of PDX-1 by performing intracellular staining and accessing the percentage positive cells by flow cytometry (FIGS. 6 and 7). Intact, 15-day-old EPC aggregates were embedded in histogel on day 15 of the pancreatic differentiation process and stained for the presence of PDX-1 by immunohistochemistry (FIG. 8).

Figure 10:
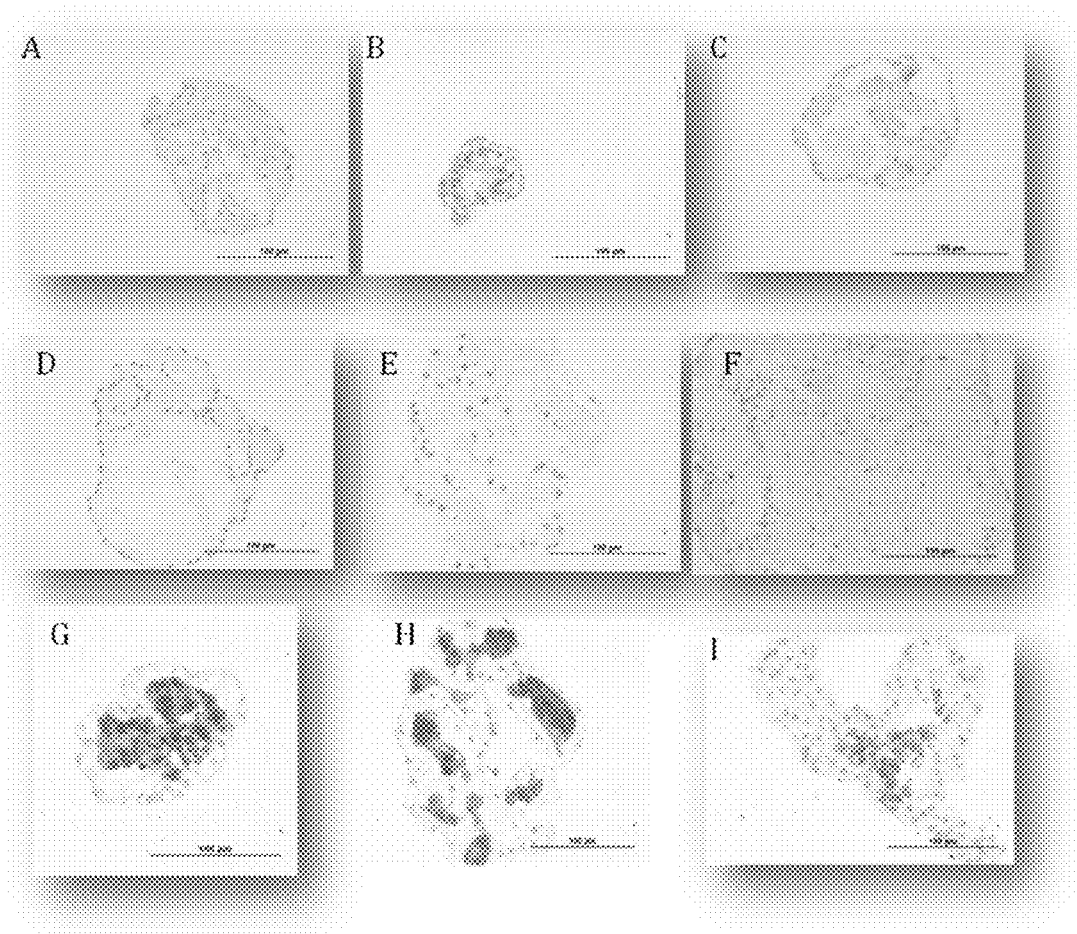
FIGS. 10A-I. Immunohistochemical staining of somatostain, glucagon, and insulin expression in intact 15-day-old EPC-aggregates on day 18 of pancreatic differentiation process. Experiment was performed under normoxic conditions. Representative images of intact 15 day EPC aggregates in suspension cultures placed in pancreatic differentiation media for 18 days, embedded in histogel, and stained for the presence of somatostatin (FIGS. 10A-C), glucagon (FIGS. 10D-F), and insulin (FIGS. 10G-I) by immunohistochemical staining Photographs were taken at 20× magnification.
Figure 11:
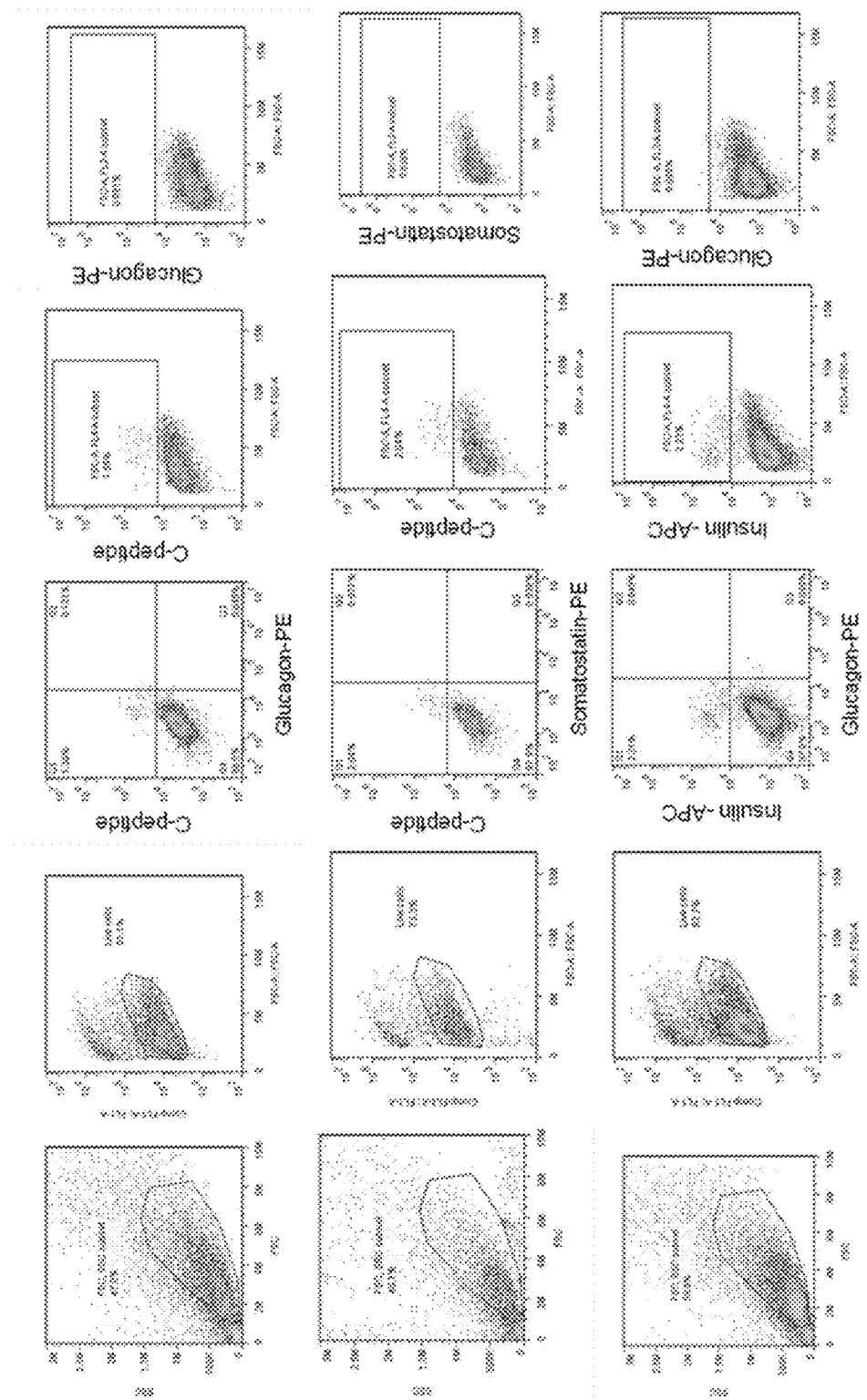
FIG. 11. Intracellular staining of C-peptide, glucagon, and insulin expression in 15-day-old EPC-aggregates on day 18 of pancreatic differentiation process following dissociation of the aggregates. Experiment was performed under normoxic conditions. The scatter plots represent intracellular staining of insulin, glucagon, somatostatin, and C-peptide expression. The plots on the left reveal Forward and Side Scatter of the cells followed by staining for live cells post harvest. The third set of plots reveal dual staining profiles of C-peptide vs. glucagon, C-peptide vs. somatostatin, and insulin vs. glucagon staining on iPSC-1131 cells. The fourth and fifth plots depict the total percentage of insulin, glucagon, C-peptide, and somatostatin expression levels.

To assess the differentiation status of the aggregates, intact, 15-day-old EPC aggregates were embedded in histogel on day 18 of the pancreatic differentiation process and stained for the presence of somatostatin (FIGS. 10A-C), glucagon (FIGS. 10D-F), and insulin (FIGS. 10G-I) by immunohistochemistry. The aggregates were found to be negative for the expression of somatostatin and glucagon but positive for the expression of insulin. Intracellular staining for C-peptide, Glucagon, and Insulin expression in 15-day-old EPC-aggregates on day 18 of pancreatic differentiation was performed following dissociation of the aggregates (FIG. 11). The data for marker expression are summarized in Table 2. The efficiency of the process to generate beta cells from EPCs is 0.3%.

TABLE 2

Summary of Glucagon, C-peptide, Somatostatin and Insulin expression profile in beta cell aggregate cultures.

| Marker | Beta cell (IHC staining) | Beta cell (Flow cytometry) |
| --- | --- | --- |
| Insulin | Present | 1.9% ± 0.2% |
| C-peptide | ND | 1.8% ± 0.3% |
| Glucagon | Absent | Absent |
| Somatostatin | Absent | Absent |
| Pdx | Present | 40%-95% |

Figure 12:
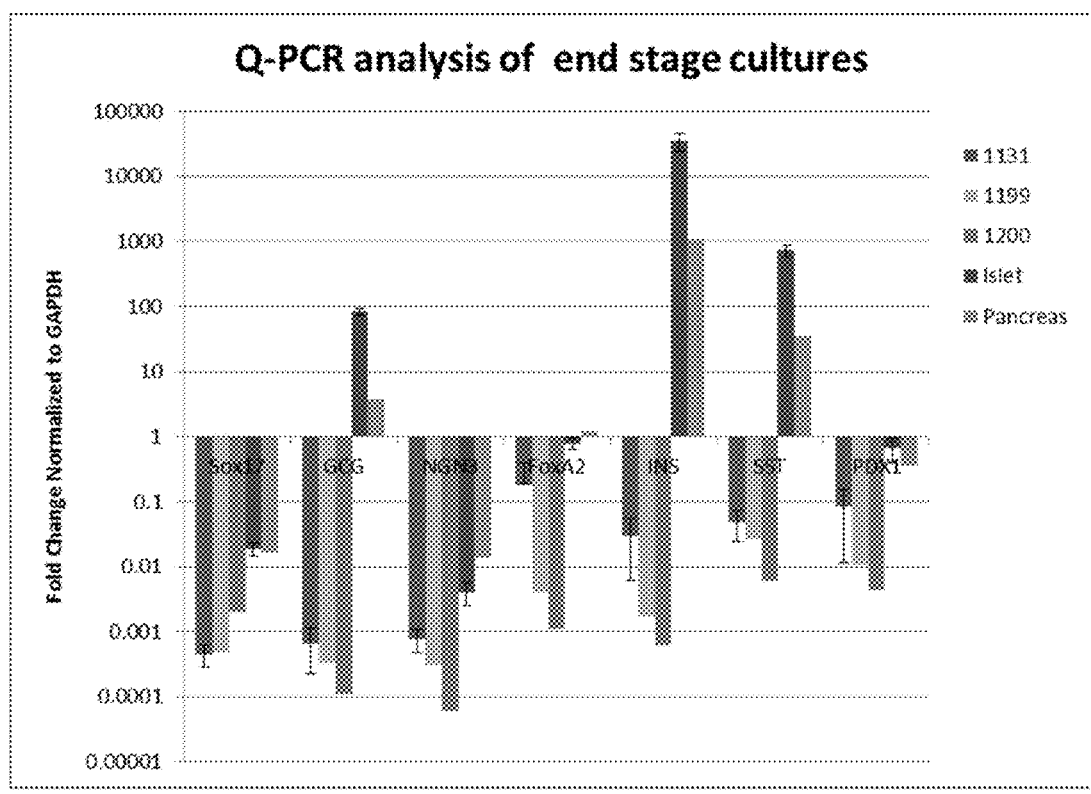
FIG. 12. Preliminary qPCR analysis of 15-day-old EPC-aggregates on day 20 of pancreatic differentiation. Experiment was performed under normoxic conditions.

To further assess the differentiation status of the aggregates, total RNA was isolated from whole pancreas, islets, and 20-day-old aggregates using an RNeasy Mini Kit (Qiagen) and treated with RNase-free DNase (Qiagen). RNA was reverse transcribed into cDNA using random hexamers and oligo(dT) with Superscript III Reverse Transcriptase (Applied Biosystems). qPCR was performed on the LightCycler 480 II (Roche) using Taqman probes and primers as described previously (Nostro et al., 2008) (FIG. 12). Expression levels were normalized to the housekeeping gene GAPDH.

Figure 13:
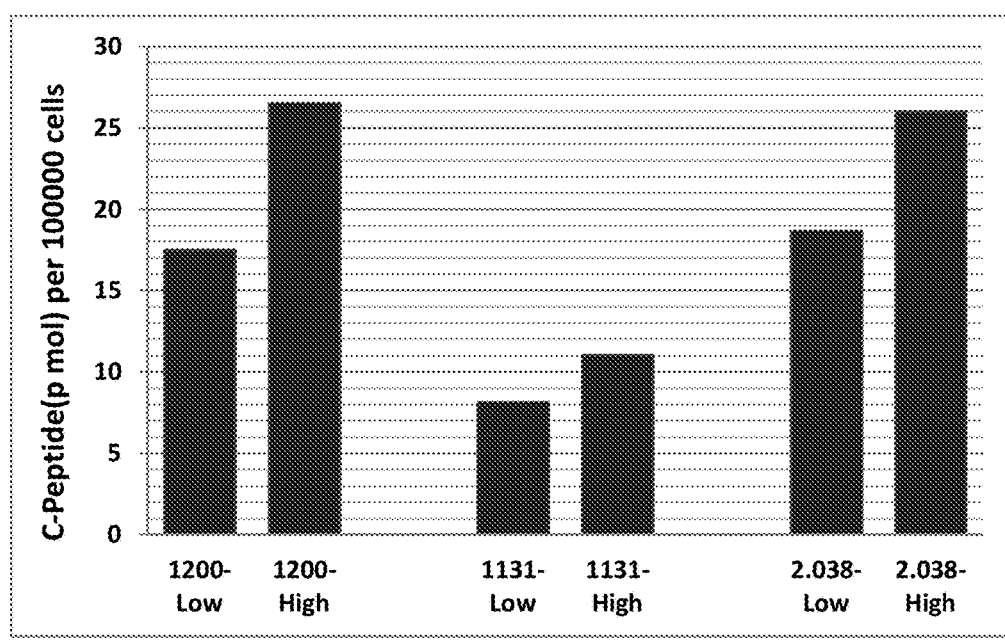
FIG. 13. Glucose-stimulated C-peptide release of 15-day-old EPC-aggregates placed in pancreatic differentiation for 25 days. The C-peptide released was normalized to 100,000 cells. Positive control cadaveric human islets: 146 pmol of C-peptide released at low glucose and 257 pmol of C-peptide released at high glucose.

C-peptide release assays were performed as previously described (D'Amour et al., 2006) using a Mercodia Ultrasensitive C-peptide ELISA kit (Mercodia). Briefly, aggregates that were beyond day 25 in the beta cell differentiation protocol from each iPSC clone were placed in a millicell PCF insert within a 24 well plate. The aggregates were equilibrated in 1 ml KRBH medium for one hour at 37° C. and 5% $CO_2$, 20% $O_2$. The aggregates were next placed in a second well containing 1 ml KRBH medium supplemented with 2.8 mM glucose and the incubation continued for one hour at 37° C. and 5% $CO_2$, 20% $O_2$. Finally, the aggregates were placed in 1 ml KRBH medium supplemented with 28 mM glucose and the incubation continued for one hour at 37° C. and 5% $CO_2$, 20% $O_2$. Extreme care was taken to drain the aggregates of all residual fluid between well transfers. The supernatant left behind was collected and stored at −20° C. About 30 human adult islets were also used as positive controls for this assay. After the iPSC-derived β-cells and cadaveric adult islets were stimulated with D-glucose at 2.8 mM (Basal) or 28 mM (Glucose), the aggregates were digested with TryPLE and the total viable cell count per sample was determined. C-peptide secretion was normalized based on the total viable cell number taken for each sample (FIG. 13). The primary human islets were purchased from University of Wisconsin Madison islet core division.

Figure 23:
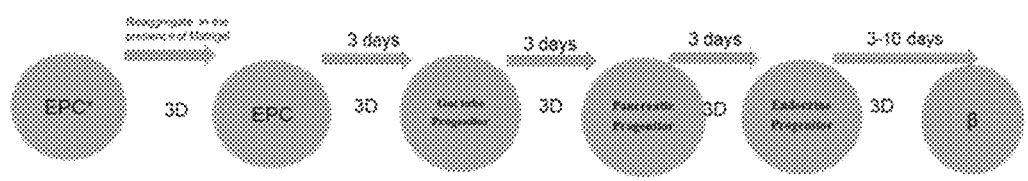
FIG. 23. Scheme for generating beta cells from EPCs propagated as 3D aggregates without MEFs.

Example 11—Generating Beta Cells from EPCs Propagated as 3D Aggregates without MEFs 2.038 AT4 EPC cultures were harvested and individualized using 0.5% Trypsin solution. The resulting cell suspension was quenched, washed, and mixed with Matrigel (0.3 mg/ml). The aggregates were placed in EPC cycling media under hypoxic conditions at a cell density of 0.3 million cells per ml. The cells were fed with fresh EPC cycling media for the first five days and beta cell differentiation was initiated on day 6 post reaggregation using the protocol described by Nostro et al. (2011) further modified by Cheng et al. (2012a) in a 3D format. A scheme of the 3D approach is provided as FIG. 23. In this scheme, EPCs can be purified by MACs separation prior to initiation of beta cell differentiation.

Figure 24:
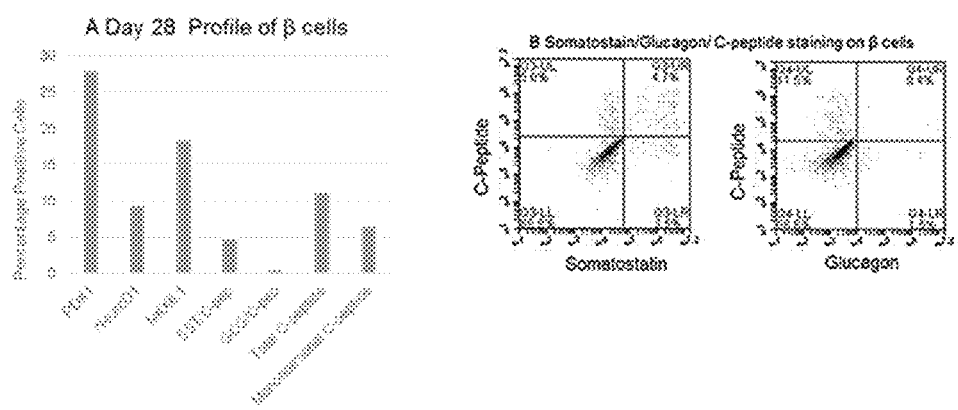
FIGS. 24A-B. Generating beta cells as 3D aggregates. Flow cytometric analysis of day 28 end-stage beta cells derived from 2.038AT4 cells. The cells were harvested, fixed using 4% paraformaldehyde, permeabilized using 0.1% saponin, and stained for the presence of PDX, NeuroD1, Nkx6.1, Somatostatin, Glucagon, and C-peptide by flow cytometry. The percentage positive cells are depicted in FIG. 24A. Dot plots generated post staining Somatostatin/C-peptide and Glucagon/C-peptide are depicted as FIG. 24B.

Day 28 end-stage beta cells derived from 2.038 AT4 cells were analyzed by flow cytometric analysis. The cells were harvested and fixed using 4% paraformaldehyde, permeabilized using 0.1% saponin, and stained for the presence of PDX, NeuroD1, Nkx6.1, Somatostatin, Glucagon, and C-peptide by flow cytometry. The percentage positive cells are depicted in FIG. 24A. Dot plots generated post-staining for Somatostatin/C-peptide and Glucagon/C-peptide are shown in FIG. 24B.

Figure 25:
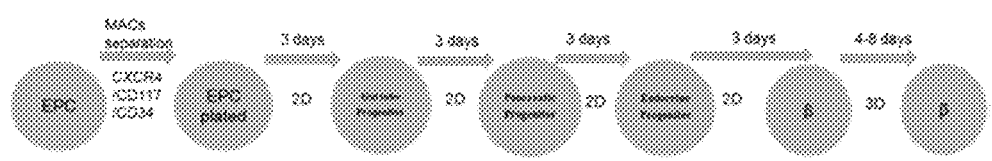
FIG. 25. Scheme for generating beta cells from EPCs propagated in 2D.

Example 12—Generating Beta Cells from EPCs Propagated as 3D Aggregates without MEFs EPCs generated in suspension culture from 2.038 cells were purified by MACS separation as described above and placed in differentiation medium for the generation of pancreatic cell types. For pancreatic differentiation of EP cells, a protocol described by Nostro et al. (2011) further modified by Cheng et al. (2012a) was utilized in a 2D format. A scheme of the 2D approach is provided as FIG. 25.

EPC cultures were purified and plated on neat Matrigel in the presence of EPC cycling media for five days. Beta cell differentiation was initiated by placing the cells in SFD media containing Wnt3A (3 ng/ml), FGF-10 (50 ng/ml) and Dorsomorphin (0.75 µM) for three days to generate foregut/midgut endoderm cells. The cells were cultured in high glucose DMEM media containing GlutaMAX (1%), B27 without retinoic acid (1%), ascorbic acid (50 µg/ml), Pen/Strep (1%), KAAD-Cyclopamine (0.25 µM), trans-Retinoic acid (2 µM), Noggin (50 ng/ml), and FGF-10 (50 ng/ml) for three days to generate pancreatic endoderm cells. Following this step the cells were cultured in high glucose DMEM media containing GlutaMAX (1%), B27 without retinoic acid (1%), ascorbic acid (50 µg/ml), Pen/Strep (1%), SB431542 (6 µM), and Noggin (50 ng/ml) for three days. Next, the cells were cultured in the previous high glucose DMEM medium supplemented with a γSecretase inhibitor (DAPT at 2 µM) for one to two days. From this stage the cells were cultured in SFD media containing glucose (40 mM), nicotinamide (10 mM), SB431542 (6 µM), and Noggin (50 ng/ml) for one to two days. Finally, the cells were cultured in SFD medium containing SB431542 (5.4 µM), Noggin (50 ng/ml), insulin (800 pM, 0.47 µl/ml), and nicotinamide (10 mM) that was alternated every day between such medium with additional glucose added (40 mM) and no additional glucose added for the next 10 days. The presence of mono hormonal beta cells was detected between day 10-15 of differentiation in a 2D format.

Figure 26A:
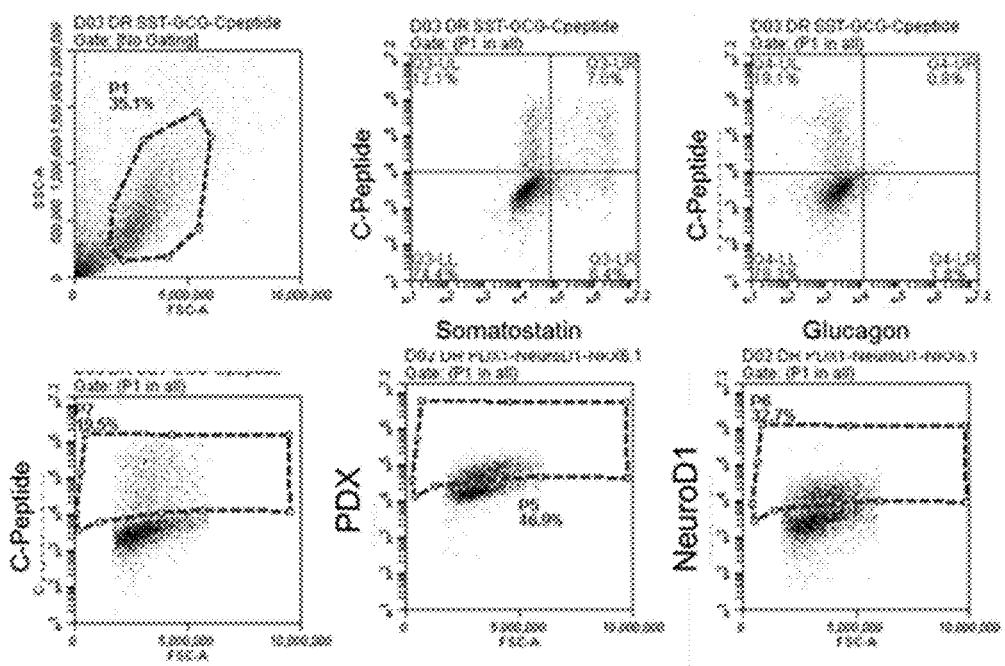
FIGS. 26A-B. Glucose responsiveness of end-stage beta cells generated from 2.038 cells.
Figure 26B:
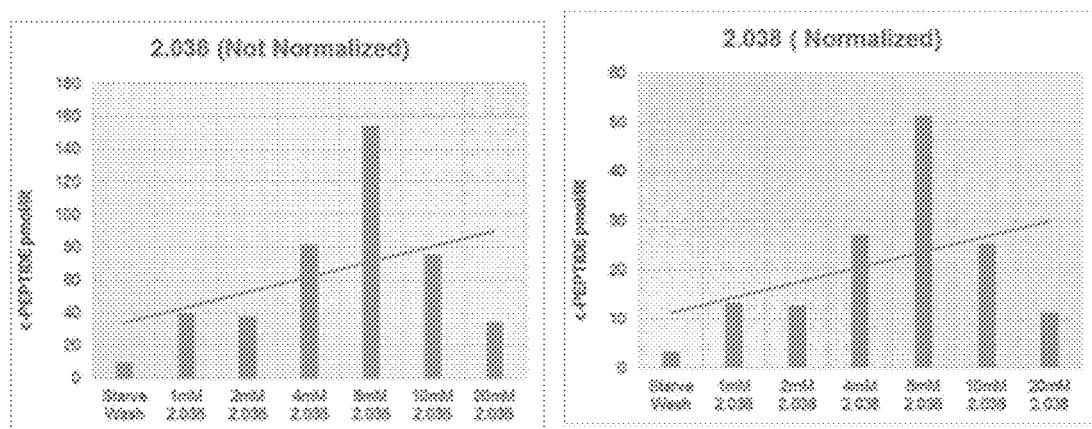

Beta cell cultures were harvested on day 15 of differentiation, fixed, and stained for quantitation of PDX/NeuroD1/C-Peptide/Glucagon/Somatostatin by intracellular flow cytometry (FIG. 26A). The end-stage cultures revealed the presence of 12% mono-hormonal cells. The end-stage cultures were positive for PDX and NeuroD1. The end-stage aggregates revealed responsiveness to glucose (FIG. 26B). The glucose response assay was performed as described and the data were normalized to cell number.

C-peptide release assays were performed as previously described (D'Amour et al., 2006) using a Mercodia Ultrasensitive C-peptide ELISA kit (Mercodia). Briefly, aggregates that were beyond day 25 in the beta cell differentiation protocol from each iPSC clone were placed in a millicell PCF insert within a 24 well plate. The aggregates were equilibrated in 1 ml KRBH medium for one hour at 37° C. and 5% $CO_2$, 20% $O_2$. The aggregates were next placed in a second well containing 0.5 ml KRBH medium supplemented with serially increasing levels of glucose from 1-20 mM. Each incubation lasted for 20 mins at 37° C. and 5% $CO_2$, 20% $O_2$. Extreme care was taken to drain the aggregates of all residual fluid between well transfers. The supernatant left behind was collected and stored at −20° C. At the end of the experiment the aggregates were digested with TryPLE and the total viable cell count per sample was determined to normalize the data. C-peptide secretion was normalized based on the total viable cell number taken for each sample.

Example 13—Generating Beta Cells from 2.038AT4 EPCs Propagating as 3D Aggregates without MEFs 2.038AT4.14EGN (also called 2.038AT4) cells were maintained in Essential 8 under hypoxic conditions during DE induction without CHIR using 2.5 ng/ml BMP4. DE were maintained in EPC cycling media without MEFs under hypoxic conditions. Media was supplemented with neomycin (100 ug/ml) and puromycin (600 ng/ml) for iPSC culture, DE culture, and EPC cycling. At P7, EPC were harvested and MACS purification was performed using CD34/CXCR4/CD117. Purified cells were plated on neat Matrigel in the presence of a Rock inhibitor.

Beta cell differentiation was initiated 5 days post re-aggregation according to the protocol described by Nostro et al. (2011) further modified by Cheng et al. (2012a) in a 2D format. Dox was added at different stages of the beta cell differentiation process. Dox (1.5 µg/ml) induction was performed between days 6-15 of beta cell differentiation, between days 8-15 of beta cell differentiation, or between days 10-15 of beta cell differentiation. The cells were harvested on day 15 of beta cell differentiation, fixed, and stained for quantification of PDX/NeuroD1/C-peptide/Glucagon/Somatostatin by intracellular flow cytometry. Analysis of emerging beta cells on day 15 revealed the presence of PDX (FIGS. 27A-D), NeuroD1 (FIGS. 27E-H), and Somatostatin/Glucagaon/C-peptide (FIGS. 27I-L). Beta cells on day 15 of differentiation revealed the presence of PDX, NeuroD1, and C-peptide positive cells, along with low Somatostatin positive cells and a lack of Glucagon positive cells. Addition of Dox between days 10-15 of the differentiation process revealed the highest levels of mono-hormonal C-peptide positive cells.

Figure 28:
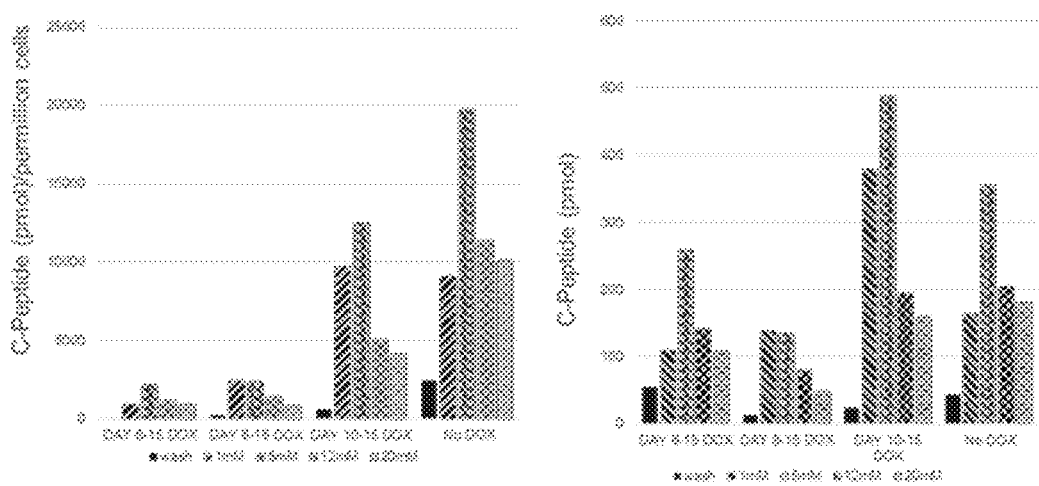
FIG. 28. Glucose responsiveness of end-stage beta cells generated from 2.038 AT4 cells. Dox was added at different stages of the beta cell differentiation process. Normalized and non-normalized C-peptide release assay results are shown. Normalization was based on the total viable cell number taken for each sample.

Example 14—Glucose Responsive End-Stage Beta Cells Derived from 2.038AT4 Cells C-peptide release assays were performed as described in Example 12. Beta cell cultures induced with Dox induction between days 10-15 generated a response to between 1-5 mM glucose (FIG. 28). The cell number was greater in Dox induced cultures compared to the uninduced conditions.

The cells were harvested on day 15 of beta cell differentiation, fixed, and stained for quantification of PDX/NeuroD1/C-Peptide/Glucagon/Somatostatin by intracellular flow cytometry. The beta cells were placed in end-stage media for an extended analysis of end-stage beta cell cultures. The cultures revealed the presence of monohormonal cells for up to 4 weeks in culture (FIG. 29).

The experiment was performed again with the addition of Dox (1.5 µg/ml) between day 10-15 of beta cell differentiation. The cells were harvested on day 15 of beta cell differentiation and assayed for PDX/NeuroD1/C-Peptide/Glucagon/Somatostatin expression levels by intracellular flow cytometry. The cells revealed 25%-30% PDX/NeuroD1 expression. The total C-Peptide levels were around 10% of which 5% of cells appeared monohormonal. Glucagon expression was not recorded. C-peptide release assays were performed as described above. The results revealed a dose-dependent response between 1-15 mM glucose. Both the Dox induced and un-induced beta cell cultures were capable of eliciting a dose-dependent response to glucose (FIG. 30).

Example 15—qPCR Analysis of End-Stage Cultures

EPCs were harvested every 4-5 days using 0.5% Trypsin-EDTA for 10-20 minutes at 37° C. Cells were vigorously pipetted to create a single-cell suspension. RNA was isolated using the RNeasy Plus Mini Kit from Qiagen (Catalog #74136) according to the manufacturer's directions. RNA quantification was performed using the Nanodrop 2000. RNA was reverse transcribed with the ImProm-II RT System from Promega (Catalog # A3800) according to manufacturer's directions. rt-qPCR was performed using TaqMan Gene Expression Master Mix (Catalog #4369016) and TaqMan probes (Catalog #4331182; INS: Hs02741908_m1; GCG: Hs01031536_m1; SST: Hs00356144_m1; Neurogenin3: Hs01875204_s1; NKX6.1: Hs00232355_m1; PDX1: Hs00236830_m1; NeuroD1: Hs01922995_s1; GAPDH: Hs99999905_m1) with technical triplicates and run on the Roche LightCycler for 45 cycles (FIG. 31). Undifferentiated iPSCs of the same genetic background were used as negative controls. Whole pancreas RNA (Ambion Catalog # AM7954) and human islets provided by the UW Islet Core were used as positive controls. Undifferentiated iPSCs of the same genetic background were used as negative controls. Fold induction was calculated by DeltaCp with normalization to GAPDH.

Example 16—qPCR Analysis of iPSC/DE/EPC/beta Cells for ERG and GFI Expression The levels of ERG (FIG. 32A) and GFI (FIG. 32B) transcripts at different stages of the process were quantified from 2.038 and 2.038AT4 cells. Dox induction of 2.038AT4 cells was only applied at the beta cell differentiation stage. Cells from 2.038AT4 were always cultured in media containing neomycin (100 µg/mL) and puromycin (600 ng/mL) regardless of stage of differentiation. RNA was isolated from undifferentiated iPSC, DE, EPC, and beta cell cultures derived from 2.038 cells and 2.038AT4 cells using the RNeasy Plus Mini Kit from Qiagen (Catalog #74136) according to the manufacturer's directions. RNA quantification was performed using the Nanodrop 2000. RNA was reverse transcribed with the ImProm-II RT System from Promega (Catalog # A3800) according to manufacturer's directions. rt-qPCR was performed using TaqMan Gene Expression Master Mix (Catalog #4369016) and TaqMan probes (ERG: Hs01554629_m1; GFI1: Hs00382207_m1; GAPDH: Hs99999905_m1) with technical triplicates and run on the Roche LightCycler for 45 cycles. Fold induction was calculated by DeltaCp with normalization to GAPDH. Undifferentiated iPSCs of the same genetic background were used as negative controls. Whole pancreas RNA (Ambion Catalog # AM7954) and human islets provided by the UW Islet Core were used as positive controls.

2.038AT4 iPSCs revealed the presence of ERG/GFI transcripts under Dox uninduced selection conditions and the levels were maintained throughout EPC cycling. There was a slight increase in the level of transcripts by Dox induction during beta cell differentiation. The parental 2.038 EPC cultures revealed upregulated levels of ERG during EPC cycling and beta cell differentiation. Without being bound by theory, these data indicate a role of ERG and GFI in promoting survival and maintenance of EPC cultures during cycling. The Dox induced cultures have a higher cell number than uninduced conditions, hence these transcription factors may help to preserve beta cells derived from EPCs.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,030,015
U.S. Pat. No. 5,460,964
U.S. Pat. No. 5,478,838
U.S. Pat. No. 5,486,359
U.S. Pat. No. 5,635,387
U.S. Pat. No. 5,677,136
U.S. Pat. No. 5,681,599
U.S. Pat. No. 5,716,827
U.S. Pat. No. 5,736,396
U.S. Pat. No. 5,750,397
U.S. Pat. No. 5,759,793
U.S. Pat. No. 5,811,094
U.S. Pat. No. 5,827,735
U.S. Pat. No. 5,827,740
U.S. Pat. No. 5,837,539
U.S. Pat. No. 5,837,670
U.S. Pat. No. 5,843,780
U.S. Pat. No. 6,833,269
U.S. Pat. No. 6,991,897
U.S. Pat. No. 7,015,037
U.S. Pat. No. 7,399,632
U.S. Pat. No. 7,410,798
U.S. Pat. No. 7,410,773
U.S. Pat. No. 7,422,736
U.S. Appln. Ser. 61/058,858
U.S. Appln. Ser. 61/172,079
U.S. Appln. Ser. 61/184,546
U.S. Patent Publn. 2003/0087919
U.S. Patent Publn. 2003/0125344
U.S. Patent Publn. 2003/0211603
U.S. Patent Publn. 2004/0002507
U.S. Patent Publn. 2004/0002508
U.S. Patent Publn. 2004/0014755
U.S. Patent Publn. 2005/0192304
U.S. Patent Publn. 2005/0209261
U.S. Patent Publn. 2007/0116680
U.S. Patent Publn. 2007/0238170
U.S. Patent Publn. 2008/0171385
International Patent Publn. 2005/123902
European Patent EP0412700
PCT Publn. WO 2003/042405
PCT Appln. WO 2008/006583
PCT Appln. WO 2008/094597
PCT Publn. PCT 2005/080554
PCT Publn. WO 01/088100
PCT Publn. WO 98/30679
PCT Publn. WO 97/37009
PCT Publn. WO 2002/076976
PCT Publn. WO 2003/059913
PCT Publn. WO 2003/062225
PCT Publn. WO 2003/062227
PCT Publn. WO 2004/039796
PCT Publn. WO 97/37009
A practical approach, 1987.
Alison et al., *Hepatol.*, 29:678-683, 1998.
Amit et al., *Dev. Bio.*, 227:271-278, 2000.
Andrews et al., In: *Teratocarcinomas and Embryonic Stem Cells*, Robertson (Ed.), IRL Press, 207-246, 1987.
Animal Cell Culture, 1987.
*Animal Cells: culture and media*, D. C. Darling, S. J. Morgan John Wiley and Sons, Ltd., 1994.
Bennett et al., *J. Biol. Chem.*, 277:34, 2002.
Bertrand et al., *J. Mol. Biol.*, 333:393-407, 2003.
Bhardwaj et al., *Nature Immunol.*, 2:172-180, 2001.
Bhatia et al., *J. Exp. Med.*, 189:1139-1148, 1999.
Boyer et al., *Cell*, 122(6):947-956, 2005.
Brunton et al., *J. Med. Chem.*, 51:1108-1110, 2008.
Byrne et al., *Nature*, 450(7169):497-502, 2007.
Cassiede et al., *J. Bone Miner. Res.*, 11(9):1264-1273, 1996.
*Cells: a laboratory manual* (vol. 1), D. L. Spector, R. D. Goldman, L. A. Leinwand (eds.), Cold Spring Harbor Laboratory Press, 1998.
Chadwick, *Blood*, 102:906, 2003.
Chambers et al., *Cell*, 113(5):643-655, 2003.
Chen et al., *Nature Methods*, 8:424-429, 2011.
Cheng et al., Self-renewing endodermal progenitor lines generated from human pluripotent stem cells, *Cell Stem Cell*, 10:371-384, 2012a.
Cheng et al., Monolayer endoderm differentiation from human ESCs (Jun. 10, 2012b), StemBook, ed. The Stem Cell Research Community, StemBook, doi/10.3824/stembook.1.64.1, on the world wide web at stembook.org.
Cheng et al., Endodermal stem cell population derived from pluripotent stem cells, *Curr. Opin. Biol.*, 2013. Chin et al., *Molecular Brain Res.*, 137(1-2):193-201, 2005.
Cheng et al., *J. of Clin. Invest.*, 120:2171-2183, 2010.
*Culture of Animal Cells: a manual of basic techniques* (3.sup.rd edition), R. I. Freshney (ed.), Wiley-Liss, Inc., 1994.
*Current Protocols in Molecular Biology and Short Protocols in Molecular Biology*, 1987; 1995.
*Current Protocols in Stem Cell Biology*, Bhatia et al. (Ed.), John Wiley and Sons, Inc., 2007.
DaCosta et al., *Molec. Pharmacol.*, 65(3):744-752, 2004.
D'Amour et al., Production of pancreatic hormone expressing endocrine cells from human embryonic stem cells, *Nat. Biotechnol.*, 24:1392-1401, 2006.
Davidson and Zon, Turning mesoderm into blood: the formation of hematopoietic stem cells during embryogenesis, *Curr. Top. Dev. Biol.*, 50:45-60, 2000.
Davies et al., *Biochem J.*, 351:95-105, 2000.
de Gouville et al., *Drug News Perspective*, 19(2):85-90, 2006.

Downey et al., *J. Biol. Chem.*, 271(35):21005-21011, 1996.
Embryonic Stem Cell Differentiation in vitro, 1993.
Evans et al., *Theriogenology*, 33:125-129, 1990.
Evans and Kaufman, *Nature*, 292:154-156, 1981.
Fernandes et al., *Nature Cell Biology*, 6:1082-1093, 2004.
Frame et al., *Biochemical J.*, 359:1-16, 2001.
Gellibert, et al., *J. Med. Chem.*, 49(7):2210-2221, 2006.
Gene Targeting, A Practical Approach, 1993.
Gould et al., *Intl. J. Neuropsychopharmacology*, 7:387-390, 2004.
Gould et al., *Pharmacological Res.*, 48:49-53, 2003.
Gouon-Evans et al., BMP-4 is required for hepatic specification of mouse embryonic stem cell-derived definitive endoderm, *Nat. Biotechnol.*, 24:1402-1411, 2006.
Gronthos, *Blood*, 84(12):4164-4173, 1994.
*Guide to Techniques in Mouse Development, Methods Enzymol.*, Vol. 225, P. M. Wassarman, M. L. DePamphilis (eds.), 1993.
Harb et al., *PLoS One*, 3(8):e3001, 2008.
Hill et al., *Exp. Hematol.*, 24(8):936-943, 1996.
Hochereau-de Reviers and Perreau, *Reprod. Nutr. Dev.*, 33:475-493, 1993.
Huber et al., Cooperative effects of growth factors involved in the induction of hematopoietic mesoderm, *Blood*, 92:4128-4137, 1998.
Inman et al., *Molec. Pharmacol.*, 62(1):65-74, 2002.
*In vitro Methods in Pharmaceutical Research*, J. V. Castell and M. J. Gomez-Lechon (eds.), Academic Press, 1997.
Jainchill et al., *J. Virol.*, 4(5):549-53, 1969.
Jaiswal et al., *J. Cell Biochem.*, 64(2):295-312, 1997.
Johnstone et al., *Exp. Cell. Res.*, 238(1):265-272, 1998.
Keller et al., *Curr. Opin. Cell Biol.*, 7(6):862-9, 1995.
Kim et al., *Xenobiotica*, 38(3):325-339, 2008.
King, The use of animal models in diabetes research, *British J. of Pharm.*, 166:877-894, 2012.
Klimanskaya et al., *Lancet*, 365(9471):1636-41, 2005.
Kobberup et al., *Developmental Dynamics*, 236:3100-3110, 2007.
Kodama et al., *J. Cell Physiol.*, 112(1):89-95, 1982.
Kuzuya et al., *Arterioscl. Thromb. Vascular Biol.*, 21:765, 2001.
Lengner et al., *Cell*, 141:872-883, 2010.
Li et al., *Nature*, 405:689-694, 2000.
Ludwig et al., *Nat. Biotechnol.*, 24(2):185-187, 2006b.
Ludwig et al., *Nat. Methods*, 3(8):637-46, 2006a.
Makino et al., *J. Clin. Invest.*, 103(5):697-705, 1999.
Marshall et al., Polarized expression of bone morphogenetic protein-4 in the human aorta-gonad-mesonephros region, *Blood*, 96:1591-1593, 2000.
Martin et al., *Nature Immunology*, 6:111-184, 2005.
Martin, *Proc. Natl. Acad. Sci. USA*, 78(12):7634-8, 1981.
McLendon et al., *FASEB J.*, 14:2383-2386, 2000.
Moore and Piedrahita, *In Vitro Cell Biol. Anim.*, 33:62-71, 1997.
Moore and Piedrahita, *Mol. Reprod. Dev.*, 45:139-144, 1996.
Noble et al., *Proc. Natl. Acad. Science, USA*, 102:6990-6995, 2005.
Nostro et al., Wnt, activin, and BMP signaling regulate distinct stages in the developmental pathway from embryonic stem cells to blood. *Cell Stem Cell*, 2:60-71, 2008.
Nostro et al., Stage-specific signaling through TGFbeta family members and WNT regulates patterning and pancreatic specification of human pluripotent stem cells, *Development*, 138:861-871, 2011.
Piedrahita et al., *Theriogenology*, 34:879-901, 1990.
Piedrahita et al., *Biol. Reprod.*, 58:1321-1329, 1998.
Pinnix et al., *J. Biol. Chem.*, 276:481-487, 2000.
Potten, *Philos. Trans. R Soc. Lond. B Biol. Sci.*, 353:821-830, 1998.
Rathjen et al., Properties and uses of Embryonic Stem Cells: Prospects for Application to Human Biology and Gene Therapy, *Reprod. Fertil. Dev.*, 10:31-47, 1998.
Reubinoff et al., *Nat. Biotechnol.*, 18:399-404, 2000.
Ring et al., *Diabetes*, 52:588-595, 2003.
Roth et al., *J. Med. Chem.*, 53:7287-7295, 2010.
Schaffer et al., *Gene*, 302(1-2):73-81, 2003.
Shearmen et al., *Biochemistry*, 39:8698-8704, 2000.
Shiroi et al., Identification of insulin-producing cells derived from embryonic stem cells by zinc-chelating dithizone, *Stem Cells*, 20:284-292, 2002.
Shroyer et al., *Genes Dev.*, 19:2412-2417, 2005.
Smith, In: *Origins and Properties of Mouse Embryonic Stem Cells, Annu. Rev. Cell. Dev. Biol.*, 2000.
Solinas et al., *J. Med. Chem.*, 55:1559-1571, 2012.
Srinivasan and Ramarao, Animal models in type 2 diabetes research: An overview, *Indian J. Med. Res.*, 125:451-472, 2007.
Strojek et al., *Theriogenology*, 33:901-903, 1990.
Suzuki et al., *Cancer Res.*, 67(5):2351-2359, 2007.
Takahashi et al., *J. Biol. Chem.*, 278:18664-18670, 2003.
Takahashi et al., *Cell*, 126:663-676, 2006.
Takahashi et al., *Cell*, 131:861-872, 2007.
Takahashi and Yamanaka, *Cell*, 126:663-676, 2006.
Thomson et al., *Proc. Natl. Acad. Sci. U.S.A.*, 92:7844-7848, 1995.
Thomson et al., *Science*, 282:1145, 1998.
Thomson and Marshall, *Curr. Top. Dev. Biol.*, 38:133-165, 1998.
Thomson and Odorico, *J. Trends. Biotechnol.*, 18:53-57, 2000.
Tojo et al., *Cancer Sci.*, 96:791-800, 2005.
Wagman, *Current Pharmaceutical Design*, 10:1105-1137, 2004.
Watanabe et al., *Nat. Neurosci.*, 8(3):288-96, 2005.
Watt, *Philos. Trans. R. Soc. Lond. B. Biol. Sci.*, 353:831, 1997.
Wheeler, *Reprod. Pert. Dev.*, 6:563-568, 1994.
Wianny et al., *Biol. Reprod.*, 57:756-764, 1997.
Winkler et al., *Org. Lett.*, 11:2824-2827, 2009.
Wolfe et al., *J. Med. Chem.*, 41:6, 1998.
Xu et al., *Nat. Biotechnol.*, 19:971-974, 2001.
Yang and Anderson, *Theriogenology*, 38:315-335, 1992.
Ying et al., *Cell*, 115:281-292, 2003.
Ying, *Nature*, 453:519-23, 2008.
Yoo et al., *J. Bone Joint Sure. Am.*, 80(12):1745-1757, 1998.
Yu et al., *Science*, 318:1917-1920, 2007.
Yu et al., *Science*, 324:797-801, 2009.
Yu and Thompson, *Genes Dev.*, 22(15):1987-1997, 2008.

What is claimed is:

1. A method of producing human self-renewing endoderm progenitor cells comprising:
   a) culturing undifferentiated human induced pluripotent stem cells (iPS cells) in a defined, serum-free, feeder cell and feeder cell conditioned media free, medium comprising Activin A or Nodal; and
   b) culturing the iPS cells of step a) in defined, serum-free, feeder-cell free medium, the media comprising Activin A, BMP4, VEGF and FGF-2 to produce definitive endoderm (DE) cells, said cells characterized as express both CXCR4 and CD117; and
   c) washing the DE cells of step b); and
   d) culturing the washed DE cells of step a) with BMP4, VEGF, FGF2, and EGF in defined, serum-free, feeder-cell free medium to selectively promote the growth of self-renewing endoderm progenitor cells (EPC cells), wherein the EPC cells are characterized as express CD34 and HNF4α.

2. The method of claim 1, further comprising e) culturing the endoderm progenitor cells with islet beta cell promoting growth factors to effect the formation of mono-hormonal pancreatic islet beta cells.

3. The method of claim 1, wherein the serum-free medium in step a) comprises Activin A.

4. The method of claim 1, wherein the culturing in step a) is carried out as an adherent culture.

5. The method of claim 1, wherein the cells from step a) comprise a population of definitive endoderm cells and endoderm progenitor cells.

6. The method of claim 1, wherein the culture of step b) further comprises TGFβ.

7. The method of claim 1, wherein the endoderm progenitor cells express CXCR4, CD34, and CD117.

8. The method of claim 7, wherein the endoderm progenitor cells further express at least one of Sox17, FoxA1, FoxA2, and CD31.

9. The method of claim 1, wherein the culturing occurs under hypoxic conditions.

10. The method of claim 9, wherein the pluripotent stem cells are maintained under hypoxic conditions prior to step a).

11. The method of claim 2, wherein the islet beta cell promoting growth factors comprise an inhibitor of AMP-activated protein kinase (AMPK), a BMP antagonist, a hedgehog inhibitor, a gamma-secretase inhibitor, an ALK5 inhibitor, retinoic acid, FGF10, B27, and Wnt3A or a GSK3 inhibitor.

12. The method of claim 2, further comprising:
i) culturing the endoderm progenitor cells with a BMP antagonist, Wnt3A, and FGF10 to effect the formation of foregut endoderm cells;
ii) culturing the foregut endoderm cells with B27, a BMP antagonist, a Hedgehog inhibitor, retinoic acid, and FGF10 to effect the formation of pancreatic endoderm cells;
iii) culturing the pancreatic endoderm cells with B27, a BMP antagonist, a gamma-secretase inhibitor, and an ALK5 inhibitor to effect the formation of endocrine precursor cells; and
iv) culturing said endocrine precursor cells with a BMP antagonist, an ALK5 inhibitor, insulin, glucose, and nicotinamide to effect the formation of mono-hormonal pancreatic islet beta cells.

13. The method of claim 12, wherein the cells comprise an inducible expression cassette encoding Erg1 and wherein step iv) further comprises inducing the cells to express Erg1.

14. The method of claim 12, wherein the cells comprise an inducible expression cassette encoding Gfi1 and wherein step iv) further comprises inducing the cells to express Gfi1.

15. The method of claim 12, wherein the mono-hormonal pancreatic islet beta cells are cultured for one to four weeks.

16. The method of claim 15, wherein the mono-hormonal pancreatic islet beta cells are cultured in a suspension culture.

17. The method of claim 2, wherein the culturing occurs under hypoxic conditions.

18. The method of claim 2, wherein the culture is free of MEF feeder cells and MEF-conditioned medium.

19. The method of claim 2, wherein the mono-hormonal pancreatic islet beta cells express PDX-1, insulin, and C-peptide, but not glucagon.

20. The method of claim 19, wherein the mono-hormonal pancreatic islet beta cells do not express somatostatin.

21. A method of producing human self-renewing endoderm progenitor cell aggregates comprising:
a) culturing human pluripotent stem cells in defined, feeder-free, serum-free medium comprising Activin A or Nodal, and BMP4 and one or both of VEGF and FGF-2, to effect the induction of endoderm cells; and
b) culturing the endoderm cells in a culture with BMP4, VEGF, FGF2, and EGF or homologs thereof in serum-free medium to effect the formation of self-renewing endoderm progenitor cell (EPC) aggregates.

22. The method of claim 21, wherein the culture of step b) further comprises Activin A.

23. The method of claim 21, wherein the culture of step b) further comprises TGFβ.

24. A method of producing human self-renewing endoderm progenitor cells comprising:
a) culturing human induced pluripotent stem (iPS) cells in a defined, feeder-free, serum-free medium comprising Activin A, BMP4 and one or both of VEGF and FGF-2; and
b) culturing the resultant cells from step a) in a culture with Activin A, BMP4, VEGF, FGF2, and EGF in defined, feeder-free, serum-free medium to selectively promote the growth of self-renewing endoderm progenitor cells (EPCs).

25. The method of claim 24, wherein the culture of step b) further comprises TGFβ.

26. The method of claim 1, wherein the human pluripotent stem cells cultured in step a) are mouse pluripotent stem cells.

27. The method of claim 1, wherein the human pluripotent stem cells cultured in step a) are human pluripotent stem cells.

28. The method of claim 21, wherein the human pluripotent stem cells cultured in step a) are mouse pluripotent stem cells.

29. The method of claim 21, wherein the human pluripotent stem cells cultured in step a) are human pluripotent stem cells.

30. The method of claim 1, wherein the culturing step b) is carried out in a suspension culture.

31. The method of claim 21, wherein the culturing step b) is carried out in a suspension culture.

32. The method of claim 24, wherein the culturing step b) is carried out in a suspension culture.

* * * * *

UNITED STATES PATENT AND TRADEMARK OFFICE
CERTIFICATE OF CORRECTION

PATENT NO. : 10,266,807 B2
APPLICATION NO. : 14/244396
DATED : April 23, 2019
INVENTOR(S) : Deepika Rajesh et al.

It is certified that error appears in the above-identified patent and that said Letters Patent is hereby corrected as shown below:

In Claim 1, Column 46, Line 62, delete "characterized as".

In Claim 1, Column 47, Line 2, delete "are characterized as".

Signed and Sealed this
Thirtieth Day of July, 2019

Andrei Iancu
*Director of the United States Patent and Trademark Office*

UNITED STATES PATENT AND TRADEMARK OFFICE
CERTIFICATE OF CORRECTION

PATENT NO. : 10,266,807 B2
APPLICATION NO. : 14/244396
DATED : April 23, 2019
INVENTOR(S) : Rajesh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 298 days.

Signed and Sealed this
Fourth Day of August, 2020

Andrei Iancu
*Director of the United States Patent and Trademark Office*